United States Patent
Pasquale et al.

(10) Patent No.: US 10,322,161 B2
(45) Date of Patent: Jun. 18, 2019

(54) EPHA4 CYCLIC PEPTIDE ANTAGONISTS FOR NEUROPROTECTION AND NEURAL REPAIR

(71) Applicants: Sanford Burnham Prebys Medical Discovery Institute, La Jolla, CA (US); The Scripps Research Institute, La Jolla, CA (US)

(72) Inventors: Elena B. Pasquale, San Diego, CA (US); Philip Dawson, San Diego, CA (US); Erika Olson, San Diego, CA (US); Stefan J. Riedl, San Diego, CA (US)

(73) Assignees: Sanford Burnham Prebys Medical Discovery Institute, La Jolla, CA (US); The Scripps Research Institute, La Jolla, CA (US)

( * ) Notice: Subject to any disclaimer, the term of this patent is extended or adjusted under 35 U.S.C. 154(b) by 325 days.

(21) Appl. No.: 15/326,442

(22) PCT Filed: Jul. 15, 2015

(86) PCT No.: PCT/US2015/040649
§ 371 (c)(1),
(2) Date: Jan. 13, 2017

(87) PCT Pub. No.: WO2016/011201
PCT Pub. Date: Jan. 21, 2016

(65) Prior Publication Data
US 2019/0038704 A1    Feb. 7, 2019

Related U.S. Application Data

(60) Provisional application No. 62/025,002, filed on Jul. 15, 2014.

(51) Int. Cl.
| | |
|---|---|
| *A61K 38/12* | (2006.01) |
| *C07K 7/08* | (2006.01) |
| *C07K 5/12* | (2006.01) |
| *A61P 25/28* | (2006.01) |
| *C07K 7/64* | (2006.01) |

(52) U.S. Cl.
CPC ............. *A61K 38/12* (2013.01); *A61P 25/28* (2018.01); *C07K 5/12* (2013.01); *C07K 7/08* (2013.01); *C07K 7/64* (2013.01)

(58) Field of Classification Search
CPC ........ A61K 38/00; A61K 47/64; A61K 38/10; C07K 16/2863; C07K 7/64; C07K 16/2866
See application file for complete search history.

(56) References Cited

U.S. PATENT DOCUMENTS

2004/0180823 A1    9/2004    Pasquale et al.
2008/0254023 A1    10/2008    Bartlett et al.

OTHER PUBLICATIONS

Betts et al. Bioinformatics for Geneticists. Ch14, Amino Acid Properties and Consequences of Substitutions, pp. 289-316. Edited by Michael R. Barnes and Ian C. Gray. Copyright 2003 John Wiley & Sons, Ltd. ISBNs: 0-470-84393-4 (HB); 0-470-84394-2 (PB). (Year: 2003).*
Carnegie, Structure and Properties of a Homologue of Gluthione, Biochem. J. 1963, vol. 89; pp. 471-478.
PCT/US2015/040649 International Search Report and Written Opinion, dated Dec. 29, 2015.
Olson, et al., "Modifications of a Nanomolar Cyclic Peptide Antagonist for the EphA4 Receptor to Achieve High Plasma Stability," ACS Med Chem Lett., Jun. 25, 2016, vol. 7, No. 9, pp. 841-846, Especially abstract.
PCT/US2016/042669, International Search Report and Written Opinion, dated Dec. 28, 2016.

* cited by examiner

*Primary Examiner* — Marcela M Cordero Garcia
*Assistant Examiner* — Jia-Hai Lee
(74) *Attorney, Agent, or Firm* — Entralta P.C.; Jeffrey M. McQuiston; Peter D. Weinstein

(57) ABSTRACT

The present specification discloses APY cyclic peptides having EphA4 antagonistic activity, pharmaceutical compositions containing such EphA4 antagonists, and methods and uses of treating an EphA4-based disease, disorder or pathology in an individual using such APY cyclic peptides or pharmaceutical compositions.

20 Claims, 4 Drawing Sheets
Specification includes a Sequence Listing.

A

B

C

D

E

EPHA4 CYCLIC PEPTIDE ANTAGONISTS FOR NEUROPROTECTION AND NEURAL REPAIR

CROSS-REFERENCES TO RELATED APPLICATIONS

This patent application is a 35 U.S.C. § 371 U.S. national stage entry of International Patent Application PCT/US2015/040649, filed Jul. 15, 2015, which claims the right of priority pursuant to 35 U.S.C. § 119(e) and is entitled to the benefit of the filing date of U.S. Provisional Patent Application 62/025,002, filed on Jul. 15, 2014, the content of each of which is hereby expressly incorporated by reference in its entirety.

GOVERNMENT LICENSE RIGHTS

This invention was made with government support under 5P01CA138390 awarded by the National Institutes of Health; under R01GM098871 awarded by the National Institutes of Health; under R01NS087070 awarded by the National Institutes of Health; under P30CA030199 awarded by the National Institutes of Health. The government has certain rights in the invention.

REFERENCE TO SEQUENCE LISTING

Submitted as part of this patent application is a Sequence Listing file in ASCII format, submitted under 37 C.F.R. § 1.821, named U.S. Ser. No. 15/326,442 having a file size of 48,070 bytes, generated on Jan. 13, 2017 and filed via EFS-Web, is provided in lieu of a paper copy, the content of which is hereby expressly incorporated by reference into the specification in its entirety

BACKGROUND

The Ephrin (Eph) receptors are a large family of receptor tyrosine kinases with many functions in physiology and disease. They bind their activating ligands, the ephrins, mainly through a high-affinity binding pocket located in the N-terminal ephrin-binding domain. Each of the five ephrin-A ligands can bind to most of the nine EphA receptors and each of the three ephrin-B ligands can bind to the five EphB receptors. A cysteine-rich region and two fibronectin type III domains connect the ephrin-binding domain to the transmembrane segment. The cytoplasmic portion of the Eph receptors includes a juxtamembrane segment, the kinase domain, a sterile-alpha-motif (SAM) domain and a C-terminal PDZ domain-binding motif. Interaction between Eph receptors and ephrin ligands, which are attached to the cell surface through a GPI-anchor (ephrin-As) or a transmembrane domain (ephrin-Bs), typically occurs at sites of cell-cell contact. Ephrin binding promotes activation of the receptor's kinase domain, triggering "forward" signals. Ephrin ligands engaged with Eph receptors can also affect the cells in which they are expressed by mediating "reverse" signals.

Ephrin type-A receptor 4 (EphA4) signaling can be activated by all ephrin ligands, including the five GPI-linked ephrin-As and the three transmembrane ephrin-Bs. Highly expressed in the nervous system, EphA4 tyrosine kinase activity and downstream signaling leads to inhibition of axon growth and retraction of synaptic structures known as dendritic spines. The repulsive effects of EphA4 in neurons help guide the growth of developing axons towards their synaptic targets and may contribute to inhibition of axon regeneration following injury. In addition, EphA4 interaction with the ephrin-A3 ligand expressed in astrocytes stimulates "reverse" signals through the ephrin that limit the uptake of the extracellular neurotransmitter glutamate, thus modulating synaptic transmission. EphA4 is also highly expressed in adult hippocampal neurons, where it controls synaptic morphology and plasticity. Furthermore, EphA4 appears to contribute to the maintenance of brain neural stem cells in an undifferentiated state. This is in contrast to muscle, where EphA4 may contribute to myoblast differentiation.

Dysregulation of EphA4 activity and/or function has been implicated in the pathophysiology of neurodegenerative disorders, the promotion of neurotoxicity, the inhibition of nerve differentiation and regeneration, and in the progression of cancer. For example, low EphA4 expression and loss-of-function mutations are linked to late onset and prolonged survival in amyotrophic lateral sclerosis (ALS), a fatal diseases that still lack any means for effective therapeutic intervention. Even partial EphA4 gene inactivation has shown beneficial effects in animal models of ALS, making EphA4 inhibition an attractive strategy for counteracting neurodegeneration. In addition, EphA4 was identified as a possible inhibitor of nerve regeneration after spinal cord injury. Experiments in mice suggest a role for EphA4 in the behavioral responses to cocaine administration. Further evidence also supports the involvement of EphA4 in the pathogenesis of spinal cord injury and other neurological diseases such as Alzheimer's disease, multiple sclerosis, stroke and traumatic brain injury. These pathological roles of EphA4 in the diseased nervous system are regarded as being linked to its increased expression and activation by ephrin ligands or Aβ-oligomers in the Alzheimer's brain, leading to abnormal inhibition of axon growth, synaptic function and neuronal survival. Furthermore, EpHA4 signaling prevents the generation of cochlear sensory hair cells suggesting that inhibition of EpHA4 activity could be an effective therapy in the treatment of hearing loss. Finally, increasing evidence also implicates EphA4 in various types of cancer, including glioblastoma, gastric cancer, pancreatic cancer, prostate cancer and breast cancer. For example, EphA4 downregulation studies have suggested a role for EphA4 in leukemia, prostate cancer, pancreatic cancer and gastric cancer cell growth and in liver cancer metastasis. High EphA4 expression has also been correlated with shorter survival in breast and gastric cancer patients, although the opposite correlation was found in lung cancer patients. EphA4 is also highly upregulated in Sezary syndrome, a leukemic variant of cutaneous T-cell lymphomas. Finally, EphA4 can enhance the oncogenic effects of fibroblast growth factor receptor 1 in glioblastoma cells. Hence, inhibiting EphA4-ephrin interaction could be useful for promoting axon regeneration and neural repair, providing neuroprotection and regulating synaptic plasticity in the nervous system as well as inhibiting the progression of cancer.

The two main strategies to block ephrin-induced EphA4 receptor signaling are inhibition of EphA4 kinase activity using kinase inhibitors and inhibition of ephrin binding to the EphA4 ligand binding domain using antagonists. Kinase inhibitors are hampered by low selectivity because they typically target multiple kinases due to the high conservation of the ATP binding pocket. As such, it is very difficult to identify kinase inhibitors selective for EphA4. In contrast, the ephrin-binding pocket in the extracellular EphA4 ligand binding domain has unique features that can be exploited for more selective antagonist targeting. However, the ephrin-binding pocket is very broad (exceeding 900 Å$^2$) and shallow for high affinity binding of small molecules, and small molecule EphA4 antagonists found to date are not very potent and exhibit problematic features that make them unsuitable for therapeutic applications. On the other hand, peptide antagonists have been identified that are highly selective for the ephrin-binding pocket of EphA4. The most potent peptide antagonist identified to date was the linear dodecapeptide KYLPYWPVLSSL (KYL; SEQ ID NO: 1) which was shown to specifically inhibit EphA4 signaling in culture systems and animal models. The KYL peptide significantly dampened ALS pathogenesis in the classic rat SOD1 G93A ALS model. In addition, recent data have shown that KYL peptide can inhibit the toxic effects of Aβ oligomers in in vitro and in vivo mouse models of Alzheimer's disease. The KYL peptide was also shown to promote axon sprouting and recovery of limb function in a rat model of spinal cord injury. Thus, the KYL peptide clearly demonstrated the therapeutic potential of EphA4 antagonistic agents. However, with a $K_D$ value of about 800-1000 nM, the linear KYL peptide lacks desired features, and as such, is not ideally suited as a platform for therapeutic development. In addition, both a phage display screen of a cyclic nonapeptide library and an NMR-based screen for smaller EphA4 peptidomimetic antagonists failed to yield peptides more potent than KYL.

Therefore there is still a need to identify EphA4 peptide antagonists that possess the required potency and stability in biological systems to make them suitable therapeutic agents in the treatment of neurodegenerative disorders, neurotoxicity, nerve regeneration and cancer.

SUMMARY

Aspects of the present specification disclose an EphA4 receptor antagonist. An EphA4 receptor antagonist can comprise a cyclic peptide comprising, consisting essentially of, or consisting of the sequence $X_1$-$X_2$-$X_3$-$C_4$-$X_5$-$X_6$-$X_7$-β$A_8$-$X_9$-W-$X_{11}$-$C_{12}$ (SEQ ID NO: 3), or $X_2$-$X_3$-$C_4$-$X_5$-$X_6$-$X_7$-β$A_8$-$X_9$-W-$X_{11}$-$C_{12}$ (SEQ ID NO: 4), or $X_3$-$C_4$-$X_5$-$X_6$-$X_7$-β$A_8$-$X_9$-W-$X_{11}$-$C_{12}$ (SEQ ID NO: 5), wherein $X_1$ is independently βA, DAla (D-A), A, E, G, Q, D, L, S, F, or Y; $X_2$ is independently P, A, G, Ahx, Ava, γAbu, βA or Sar; $X_3$ is independently Y, F, W, V, L, H or I; $X_5$ is independently V or L; $X_6$ is independently Y, F, W or H; $X_7$ is independently any amino acid; $X_9$ is independently any amino acid; and $X_{11}$ is independently any amino acid; wherein $C_4$ and $C_{12}$ form a disulfide bridge; wherein $C_{12}$ is optionally amidated and wherein the amino-terminus may optionally be acetylated. The length of the cyclic peptide may be 10 to 16 amino acids in length or more.

Other aspects of the present specification disclose a pharmaceutical composition comprising one or more EphA4 receptor antagonists disclosed herein. A pharmaceutical composition disclosed can further comprises one or more pharmaceutical acceptable carriers.

Other aspects of the present specification disclose a method of treating an EphA4-based disease, disorder or pathology. The disclosed method can comprise administering an EphA4 receptor antagonist disclosed herein or a pharmaceutical composition disclosed herein to an individual in need thereof. Administration of an EphA4 receptor antagonist disclosed herein or a pharmaceutical composition disclosed herein reduces one or more symptoms associated with the EphA4-based disease, disorder or pathology. An EphA4-based disease, disorder or pathology includes, without limitation, a neurodegenerative disease, a hearing loss, a promotion of nerve regeneration, a promotion of neuroprotection, or a cancer.

Other aspects of the present specification disclose a method of treating a neurodegenerative disease. The disclosed method can comprise administering an EphA4 receptor antagonist disclosed herein or a pharmaceutical composition disclosed herein to an individual in need thereof. Administration of an EphA4 receptor antagonist disclosed herein or a pharmaceutical composition disclosed herein reduces one or more symptoms associated with the neurodegenerative disease.

Other aspects of the present specification disclose a method of treating a hearing loss. The disclosed method can comprise administering an EphA4 receptor antagonist disclosed herein or a pharmaceutical composition disclosed herein to an individual in need thereof. Administration of an EphA4 receptor antagonist disclosed herein or a pharmaceutical composition disclosed herein reduces one or more symptoms associated with the hearing loss.

Other aspects of the present specification disclose a method of promoting nerve regeneration. The disclosed method can comprise administering an EphA4 receptor antagonist disclosed herein or a pharmaceutical composition disclosed herein to an individual in need thereof. Administration of an EphA4 receptor antagonist disclosed herein or a pharmaceutical composition disclosed herein stimulates of facilitates neuronal differentiation and/or growth, thereby promoting nerve regeneration.

Other aspects of the present specification disclose a method of promoting neuroprotection. The disclosed method can comprise administering an EphA4 receptor antagonist disclosed herein or a pharmaceutical composition disclosed herein to an individual in need thereof. Administration of an EphA4 receptor antagonist disclosed herein or a pharmaceutical composition disclosed herein protects neurons or nerve tissue from damage, thereby promoting neuroprotection.

Other aspects of the present specification disclose a method of treating a cancer. The disclosed method can comprise administering an EphA4 receptor antagonist disclosed herein or a pharmaceutical composition disclosed herein to an individual in need thereof. Administration of an EphA4 receptor antagonist disclosed herein or a pharmaceutical composition disclosed herein reduces one or more symptoms associated with the cancer.

Other aspects of the present specification disclose a use of an EphA4 receptor antagonist disclosed herein in the manufacture of a medicament for treating an EphA4-based disease, disorder or pathology. Other aspects of the present specification disclose a use of an EphA4 receptor antagonist disclosed herein in the manufacture of a medicament for treating a neurodegenerative disease. Other aspects of the present specification disclose a use of an EphA4 receptor antagonist disclosed herein in the manufacture of a medicament for treating a hearing loss. Other aspects of the present specification disclose a use of an EphA4 receptor antagonist disclosed herein in the manufacture of a medicament for treating a cancer.

Other aspects of the present specification disclose a use of an EphA4 receptor antagonist disclosed herein or a pharmaceutical composition disclosed herein in the treatment of an EphA4-based disease, disorder or pathology. Other aspects of the present specification disclose a use of an EphA4 receptor antagonist disclosed herein or a pharmaceutical composition disclosed herein in the treatment of a neurodegenerative disease. Other aspects of the present specification disclose a use of an EphA4 receptor antagonist disclosed herein or a pharmaceutical composition disclosed herein in the treatment of a hearing loss. Other aspects of the present specification disclose a use of an EphA4 receptor antagonist disclosed herein or a pharmaceutical composition disclosed herein in the treatment of a cancer.

Other aspects of the present specification disclose a use of an EphA4 receptor antagonist disclosed herein in the manufacture of a medicament for promoting nerve regeneration. Other aspects of the present specification disclose a use of an EphA4 receptor antagonist disclosed herein in the manufacture of a medicament for promoting neuroprotection.

Other aspects of the present specification disclose a use of an EphA4 receptor antagonist disclosed herein or a pharmaceutical composition disclosed herein in the promotion of nerve regeneration. Other aspects of the present specification disclose a use of an EphA4 receptor antagonist disclosed herein or a pharmaceutical composition disclosed herein in the promotion of neuroprotection.

DETAILED DESCRIPTION

Figure 1:
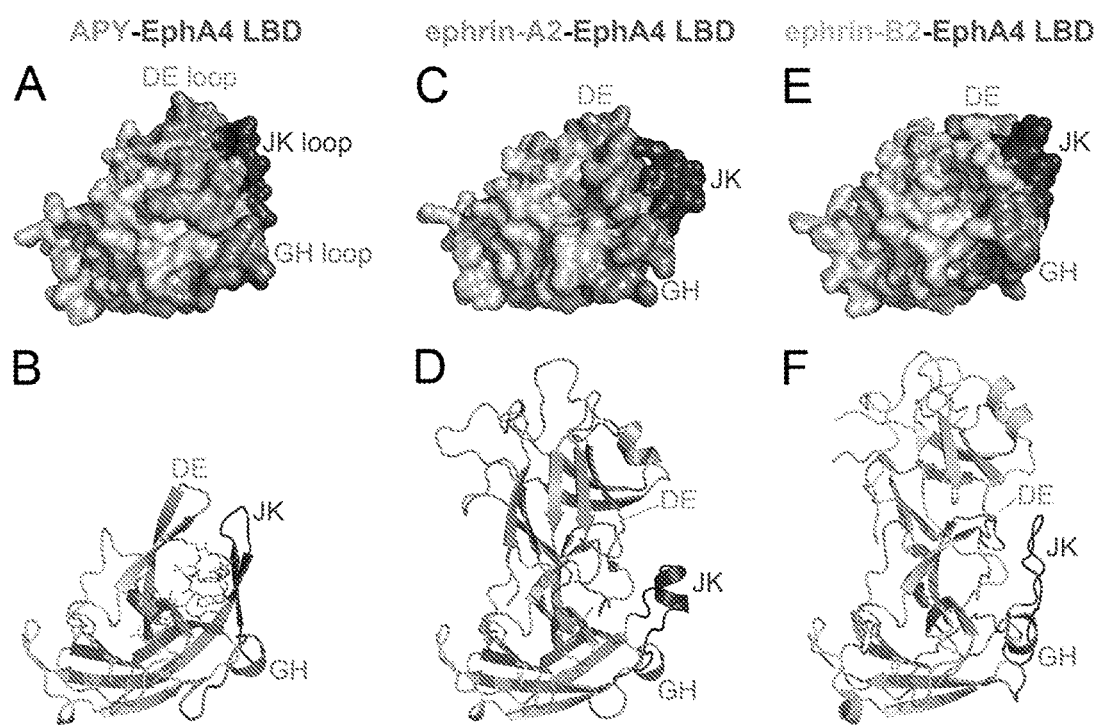
FIG. 1A shows crystal structures of the EphA4 ligand binding domain (grey) in complex with APY (orange) shown as surface representation.
FIG. 1B shows crystal structures of the EphA4 ligand binding domain (grey) in complex with APY (orange sticks) shown as ribbon representation.
FIG. 1C shows crystal structures of the EphA4 ligand binding domain (grey) in complex with part of the GH loop of ephrin-A2 (green, PDB 2W03) shown as surface representation.
FIG. 1D shows crystal structures of the EphA4 ligand binding domain (grey) in complex with the ephrin-A2 receptor-binding domain (green) shown as ribbon representation; (E) the EphA4 ligand binding domain (grey) in complex with part of the GH loop of ephrin-B2 (cyan, PDB 2W02) shown as surface representation.
FIG. 1F shows crystal structures of the EphA4 ligand binding domain (grey) in complex with the ephrin-B2 receptor-binding domain (cyan) shown as ribbon representation. The DE, GH and JK loops lining the ephrin-binding pocket in the EphA4 ligand binding domain are shown in darker shades of grey.

EphA4 is a particularly promiscuous receptor that can bind both ephrin-A and ephrin-B ligands. The difficulties in obtaining submicromolar EphA4 antagonists are likely due to the nature of the ephrin-binding pocket of EphA4 to accommodate the binding of multiple ligands. For example, ephrin-binding pocket of EphA4 is very broad (exceeding an estimated 900 Å$^2$), lacks sufficient hot spot regions and is highly dynamic, being able to assume multiple conformations. These features reduce the potential free energy gain for the binding of small molecules and flexible linear peptide ligands. In contrast to linear peptides, cyclic peptides are more structured in their unbound form, which can improve binding affinity and pharmacokinetic properties. Furthermore, cyclic peptides are able to better occupy a wide cavity such as the ephrin-binding pocket of EphA4 due to their circular conformation.

Towards this end, the cyclic peptide APYCVYRGSWSC (APY; SEQ ID NO: 2) was optimized to identify peptide that have high potency and selectivity for EphA4 as well a good physiological stability. The APY peptide was selected, in part, because it has an intramolecular disulfide bond, is only marginally less potent towards EphA4 than KYL, and selectively inhibits EphA4 but not other Eph receptors. The crystal structure of APY bound to the EphA4 ligand binding domain was solved in order to reveal mechanism of APY-mediated antagonism. This structural analysis enabled rational design of an improved APY cyclic peptide derivatives. The crystal structure of one of these derivatives reveal features contributing to its increased potency. Secondary phage display screens were also conducted to discriminate the importance of different peptide residues. Using this information further APY cyclic peptide derivatives were created that exhibited better potency and stability. The more potent APY cyclic peptide derivatives disclosed herein can serve as therapeutic agents for targeting EphA4 in neurodegenerative disorders, neurotoxicity, nerve regeneration and cancer.

Aspects of the present specification disclose, in part, an EphA4 receptor antagonist. An EphA4 receptor antagonist disclosed herein (also referred to as an EphA4 antagonist) is a cyclic peptide that selectively reduce or inhibit EphA4 receptor signaling activity and/or reduce or inhibit any other functionality of an EphA4 receptor. In aspects of this embodiment, an EphA4 receptor antagonist comprising a cyclic peptide completely inhibits EphA4 receptor signaling activity and/or other functionality of an EphA4 receptor. In aspects of this embodiment, an EphA4 receptor antagonist comprising a cyclic peptide may selectively reduce or inhibit EphA4 receptor signaling activity and/or other functionality of an EphA4 receptor by, e.g., about 10%, about 20%, about 30%, about 40%, about 50%, about 60%, about 70%, about 80%, about 60%, or about 100%. In other aspects of this embodiment, an EphA4 receptor antagonist comprising a cyclic peptide may selectively reduce or inhibit EphA4 receptor signaling activity and/or other functionality of an EphA4 receptor by, e.g., at least 10%, at least 20%, at least 30%, at least 40%, at least 50%, at least 60%, at least 70%, at least 80%, at least 60%, or at least 100%. In yet other aspects of this embodiment, an EphA4 receptor antagonist comprising a cyclic peptide may selectively reduce or inhibit EphA4 receptor signaling activity and/or other functionality of an EphA4 receptor by, e.g., at most 10%, at most 20%, at most 30%, at most 40%, at most 50%, at most 60%, at most 70%, at most 80%, at most 60%, or at most 100%. In still another aspect of this embodiment, an EphA4 receptor antagonist comprising a cyclic peptide may reduce or inhibit EphA4 receptor signaling activity and/or other functionality of an EphA4 receptor by, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100%.

Aspects of the present specification disclose, in part, a cyclic peptide. Cyclic peptides disclosed herein are peptides derived from APY (SEQ ID NO: 2), a 12 amino acid peptide with a disulfide bridge between the two cysteines (Cys) at positions 4 and 12. All APY cyclic peptides disclosed herein contain a disulfide bridge, which helps impart the cyclic structure of the peptide. All APY cyclic peptides disclosed herein are useful as an EphA4 receptor antagonist. An APY cyclic peptide disclosed herein can be chemically synthesized using standard techniques such as liquid-phase synthesis or solid-phase synthesis including Fmoc and Boc.

In aspects of this embodiment, an APY cyclic peptide may have an amino acid length of, e.g., about 9 residues, about 10 residues, about 11 residues, about 12 residues, about 13 residues, about 14 residues or about 15 residues. In other aspects of this embodiment, an APY cyclic peptide may have an amino acid length of, e.g., at least 9 residues, at least 10 residues, at least 11 residues, at least 12 residues, at least 13 residues, at least 14 residues, at least 15 residues, at least 16 residues, at least 17 residues, at least 18 residues, at least 19 residues or at least 20 residues. In yet other aspects of this embodiment, an APY cyclic peptide may have an amino acid length of, e.g., at most 9 residues, at most 10 residues, at most 11 residues, at most 12 residues, at most 13 residues, at most 14 residues, at most 15 residues, at most 16 residues, at most 17 residues, at most 18 residues, at most 19 residues or at most 20 residues. In still other aspects of this embodiment, an APY cyclic peptide may have an amino acid length of, e.g., about 9 to about 10 residues, about 9 to about 11 residues, about 9 to about 12 residues, about 9 to about 13 residues, about 9 to about 14 residues, about 9 to about 15 residues, about 9 to about 16 residues, about 9 to about 17 residues, about 9 to about 18 residues, about 9 to about 19 residues, about 9 to about 20 residues, about 10 to about 11 residues, about 10 to about 12 residues, about 10 to about 13 residues, about 10 to about 14 residues, about 10 to about 15 residues, about 10 to about 16 residues, about 10 to about 17 residues, about 10 to about 18 residues, about 10 to about 19 residues, about 10 to about 20 residues, about 11 to about 12 residues, about 11 to about 13 residues, about 11 to about 14 residues, about 11 to about 15 residues, about 11 to about 16 residues, about 11 to about 17 residues, about 11 to about 18 residues, about 11 to about 19 residues, about 11 to about 20 residues, about 12 to about 13 residues, about 12 to about 14 residues, about 12 to about 15 residues, about 12 to about 16 residues, about 12 to about 17 residues, about 12 to about 18 residues, about 12 to about 19 residues, about 12 to about 20 residues, about 13 to about 14 residues, about 13 to about 15 residues, about 13 to about 16 residues, about 13 to about 17 residues, about 13 to about 18 residues, about 13 to about 19 residues, about 13 to about 20 residues, about 14 to about 15 residues, about 14 to about 16 residues, about 14 to about 17 residues, about 14 to about 18 residues, about 14 to about 19 residues, about 14 to about 20 residues, about 15 to about 16 residues, about 15 to about 17 residues, about 15 to about 18 residues, about 15 to about 19 residues, about 15 to about 20 residues, about 16 to about 17 residues, about 16 to about 18 residues, about 16 to about 19 residues, or about 16 to about 20 residues.

Aspects of the present specification disclose, in part, an APY cyclic peptide disclosed herein that is modified by amidation (am). Amidation is a chemical reaction that results in the addition of an amide functional group to the free carboxyl group of an amino acid. In C-terminal amidation, an amide group is added to the free carboxyl group of the C-terminal residue of a peptide. C-terminal amidation increases peptide stability because it eliminates a potential charge, thereby further protecting the peptide from rapid degradation by ubiquitous exopeptidases. In an aspect of this embodiment, an APY cyclic peptide disclosed herein is amidated by adding an amide group to the free carboxyl group of the C-terminal amino acid. In another aspect of this embodiment, an APY cyclic peptide disclosed herein is amidated at the cysteine located at position 12.

Aspects of the present specification disclose, in part, an APY cyclic peptide disclosed herein that is optionally modified by acetylation (ac). Acetylation is a chemical reaction that results in the addition of an acetyl functional group to the free amino group of an amino acid. In N-terminal acetylation, an acetyl group is added to the free amino group of the N-terminal residue of a peptide. N-terminal acetyl increases peptide stability because it eliminates a potential charge, thereby further protecting the peptide from rapid degradation by ubiquitous exopeptidases. In an aspect of this embodiment, an APY cyclic peptide disclosed herein is acetylated by adding an acetyl group to the free amino group of the N-terminal amino acid. In another aspect of this embodiment, an APY cyclic peptide disclosed herein is acetylated at position 1. In yet another aspect of this embodiment, an APY cyclic peptide disclosed herein is not acetylated at the free amino group of the N-terminal amino acid.

Aspects of the present specification disclose, in part, an APY cyclic peptide disclosed herein that is optionally modified at the amino terminus. Besides acetylation, an APY peptide disclosed herein may optionally be modified by other functional groups in order to increase peptide stability. In an aspect of this embodiment, an APY cyclic peptide disclosed herein may be modified at the N-terminus by carboxybenzyl (Cbz). In yet another aspect of this embodiment, an APY cyclic peptide disclosed herein is not modified at the N-terminus by carboxybenzyl (Cbz).

In an embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4) or $X_3$-$C_4$-$X_5$-$X_6$-$X_7$-$\beta A_8$-$X_9$-W-$X_{11}$-$C_{12}$ (SEQ ID NO: 5), wherein $X_1$ is independently βA, D-A, A, E, G, Q, D, L, S, F, or Y; $X_2$ is independently P, A, G, Ahx, Ava, γAbu, βA or Sar; $X_3$ is independently Y, F, W, V, L, H or I; $X_5$ is independently V or L; $X_6$ is independently Y, F, W or H; $X_7$ is independently any amino acid; $X_9$ is independently any amino acid; and $X_{11}$ is independently any amino acid. Residues $C_4$ and $C_{12}$ of an APY cyclic peptide disclosed herein form a disulfide bridge. In an aspect of this embodiment, residue $C_{12}$ is optionally amidated. In another aspect of this embodiment, the amino-terminal residue is optionally acetylated.

In aspects of this embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4) or $X_3$-$C_4$-$X_5$-$X_6$-$X_7$-$\beta A_8$-$X_9$-W-$X_{11}$-$C_{12}$ (SEQ ID NO: 5), wherein in any residue position combination thereof $X_1$ is independently βA, D-A, A, E, G or Q; $X_2$ is independently P or A; $X_3$ is independently Y, F, W, V, L or H; $X_5$ is independently V or L; $X_6$ is independently Y, F, W or H; $X_7$ is independently any amino acid except P; $X_9$ is independently any amino acid except P; and $X_{11}$ is independently any amino acid except P. In other aspects of this embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4) or $X_3$-$C_4$-$X_5$-$X_6$-$X_7$-$\beta A_8$-$X_9$-W-$X_{11}$-$C_{12}$ (SEQ ID NO: 5), wherein in any residue position combination thereof $X_1$ is independently βA, D-A, A, E, G or Q; $X_2$ is independently P or A; $X_3$ is independently Y, F, W, V, L or H; $X_5$ is independently V or L; $X_6$ is independently Y, F, W or H; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In yet other aspects of this embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4) or $X_3$-$C_4$-$X_5$-$X_6$-$X_7$-$\beta A_8$-$X_9$-W-$X_{11}$-$C_{12}$ (SEQ ID NO: 5), wherein in any residue position combination thereof $X_1$ is independently βA, D-A, A, E, G or Q; $X_2$ is independently P or A; $X_3$ is independently Y, F, W, V, L or H; $X_5$ is independently V or L; $X_6$ is independently Y, F, W or H; $X_7$ is independently R, T, N, D, S, or Q; $X_9$ is independently S, E, T, V, W, R, L, D, Y; and $X_{11}$ is independently S, E, L, N, T, K, V, I or H. In still other aspects of this embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4) or $X_3$-$C_4$-$X_5$-$X_6$-$X_7$-$\beta A_8$-$X_9$-W-$X_{11}$-$C_{12}$ (SEQ ID NO: 5), wherein in any residue position combination thereof $X_1$ is independently βA, D-A, A, E, G or Q; $X_2$ is independently P or A; $X_3$ is independently Y, F, W, V, L or H; $X_5$ is independently V or L; $X_6$ is independently Y, F, W or H; $X_7$ is independently R, T, or N; $X_9$ is independently S, E, T, V, D, Y; and $X_{11}$ is independently S, E, L, N, K, V, I or H. In other aspects of this embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4) or $X_3$-$C_4$-$X_5$-$X_6$-$X_7$-$\beta A_8$-$X_9$-W-$X_{11}$-$C_{12}$ (SEQ ID NO: 5), wherein in any residue position combination thereof $X_1$ is independently βA, D-A, A or E; $X_2$ is independently P or A; $X_3$ is independently Y, F, W, V, L or H; $X_5$ is independently V or L; $X_6$ is independently Y, F, W or H; $X_7$ is independently R, T, or N; $X_9$ is independently S, E, T or V; and $X_{11}$ is independently S, E, L or N.

In aspects of this embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4) or $X_3$-$C_4$-$X_5$-$X_6$-$X_7$-$\beta A_8$-$X_9$-W-$X_{11}$-$C_{12}$ (SEQ ID NO: 5), wherein in any residue position combination thereof $X_1$ is independently βA, D-A, A or E; $X_2$ is independently P or A; $X_3$ is independently Y, F, W, V, L or H; $X_5$ is independently V or L; $X_6$ is independently Y, F, W or H; $X_7$ is independently any amino acid except P; $X_9$ is independently any amino acid except P; and $X_{11}$ is independently any amino acid except P. In other aspects of this embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4) or $X_3$-$C_4$-$X_5$-$X_6$-$X_7$-$\beta A_8$-$X_9$-W-$X_{11}$-$C_{12}$ (SEQ ID NO: 5), wherein in any residue position combination thereof $X_1$ is independently βA, D-A, A or E; $X_2$ is independently P or A; $X_3$ is independently Y, F, W, V, L or H; $X_5$ is independently V or L; $X_6$ is independently Y, F, W or H; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In yet other aspects of this embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4) or $X_3$-$C_4$-$X_5$-$X_6$-$X_7$-$\beta A_8$-$X_9$-W-$X_{11}$-$C_{12}$ (SEQ ID NO: 5), wherein in any residue position combination thereof $X_1$ is independently βA, D-A, A or E; $X_2$ is independently P or A; $X_3$ is independently Y, F, W, V, L or H; $X_5$ is independently V or L; $X_6$ is independently Y, F, W or H; $X_7$ is independently R, T, N, D, S, or Q; $X_9$ is independently S, E, T, V, W, R, L, D, Y; and $X_{11}$ is independently S, E, L, N, T, K, V, I or H. In still other aspects of this embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4) or $X_3$-$C_4$-$X_5$-$X_6$-$X_7$-$\beta A_8$-$X_9$-W-$X_{11}$-$C_{12}$ (SEQ ID NO: 5), wherein in any residue position combination thereof $X_1$ is independently βA, D-A, A or E; $X_2$ is independently P or A; $X_3$ is independently Y, F, W, V, L or H; $X_5$ is independently V or L; $X_6$ is independently Y, F, W or H; $X_7$ is independently R, T, N, D, S, or Q; $X_9$ is independently S, E, T, V, D, Y; and $X_{11}$ is independently S, E, L, N, K, V, I or H. In other aspects of this embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4) or $X_3$-$C_4$-$X_5$-$X_6$-$X_7$-$\beta A_8$-$X_9$-W-$X_{11}$-$C_{12}$ (SEQ ID NO: 5), wherein in any residue position combination thereof $X_1$ is independently βA, D-A, A or E; $X_2$ is independently P or A; $X_3$ is independently Y, F, W, V, L or H; $X_5$ is independently V or L; $X_6$ is independently Y, F, W or H; $X_7$ is independently R, T, or N; $X_9$ is independently S, E, T or V; and $X_{11}$ is independently S, E, L or N.

In aspects of this embodiment, an APY cyclic peptide has the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-β$A_8$-$X_9$-W-$X_{11}$-$C_{12}$ (SEQ ID NO: 4) or $X_3$-$C_4$-$X_5$-$X_6$-$X_7$-β$A_8$-$X_9$-W-$X_{11}$-$C_{12}$ (SEQ ID NO: 5), wherein $X_1$ is independently βA, D-A, A or E; $X_2$ is independently P or A; $X_3$ is independently Y, F or W; $X_5$ is independently V or L; $X_6$ is independently Y, F or W; $X_7$ is independently any amino acid except P; $X_9$ is independently any amino acid except P; and $X_{11}$ is independently any amino acid except P. In other aspects of this embodiment, an APY cyclic peptide has the sequence $X_1$-$X_2$-$X_3$-$C_4$-$X_5$-$X_6$-$X_7$-β$A_8$-$X_9$-W-$X_{11}$-$C_{12}$ (SEQ ID NO: 3), $X_2$-$X_3$-$C_4$-$X_5$-$X_6$-$X_7$-β$A_8$-$X_9$-W-$X_{11}$-$C_{12}$ (SEQ ID NO: 4) or $X_3$-$C_4$-$X_5$-$X_6$-$X_7$-β$A_8$-$X_9$-W-$X_{11}$-$C_{12}$ (SEQ ID NO: 5), wherein $X_1$ is independently βA, D-A, A or E; $X_2$ is independently P or A; $X_3$ is independently Y, F or W; $X_5$ is independently V or L; $X_6$ is independently Y, F or W; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In yet other aspects of this embodiment, an APY cyclic peptide has the sequence $X_1$-$X_2$-$X_3$-$C_4$-$X_5$-$X_6$-$X_7$-β$A_8$-$X_9$-W-$X_{11}$-$C_{12}$ (SEQ ID NO: 3), $X_2$-$X_3$-$C_4$-$X_5$-$X_6$-$X_7$-β$A_8$-$X_9$-W-$X_{11}$-$C_{12}$ (SEQ ID NO: 4) or $X_3$-$C_4$-$X_5$-$X_6$-$X_7$-β$A_8$-$X_9$-W-$X_{11}$-$C_{12}$ (SEQ ID NO: 5), wherein $X_1$ is independently βA, D-A, A or E; $X_2$ is independently P or A; $X_3$ is independently Y, F or W; $X_5$ is independently V or L; $X_6$ is independently Y, F or W; $X_7$ is independently R, T, N, D, S, or Q; $X_9$ is independently S, E, T, V, W, R, L, D, Y; and $X_{11}$ is independently S, E, L, N, T, K, V, I or H. In still other aspects of this embodiment, an APY cyclic peptide has the sequence $X_1$-$X_2$-$X_3$-$C_4$-$X_5$-$X_6$-$X_7$-β$A_8$-$X_9$-W-$X_{11}$-$C_{12}$ (SEQ ID NO: 3), $X_2$-$X_3$-$C_4$-$X_5$-$X_6$-$X_7$-β$A_8$-$X_9$-W-$X_{11}$-$C_{12}$ (SEQ ID NO: 4) or $X_3$-$C_4$-$X_5$-$X_6$-$X_7$-β$A_8$-$X_9$-W-$X_{11}$-$C_{12}$ (SEQ ID NO: 5), wherein $X_1$ is independently βA, D-A, A or E; $X_2$ is independently P or A; $X_3$ is independently Y, F or W; $X_5$ is independently V or L; $X_6$ is independently Y, F or W; $X_7$ is independently R, T, N, D, S, or Q; $X_9$ is independently S, E, T, V, D, Y; and $X_{11}$ is independently S, E, L, N, K, V, I or H. In other aspects of this embodiment, an APY cyclic peptide has the sequence $X_1$-$X_2$-$X_3$-$C_4$-$X_5$-$X_6$-$X_7$-β$A_8$-$X_9$-W-$X_{11}$-$C_{12}$ (SEQ ID NO: 3), $X_2$-$X_3$-$C_4$-$X_5$-$X_6$-$X_7$-β$A_8$-$X_9$-W-$X_{11}$-$C_{12}$ (SEQ ID NO: 4) or $X_3$-$C_4$-$X_5$-$X_6$-$X_7$-β$A_8$-$X_9$-W-$X_{11}$-$C_{12}$ (SEQ ID NO: 5), wherein $X_1$ is independently βA, D-A, A or E; $X_2$ is independently P or A; $X_3$ is independently Y, F or W; $X_5$ is independently V or L; $X_6$ is independently Y, F or W; $X_7$ is independently R, T, or N; $X_9$ is independently S, E, T or V; and $X_{11}$ is independently S, E, L or N.

In another embodiment, an APY cyclic peptide has the sequence $X_1$-$P_2$-$X_3$-$C_4$-$X_5$-$X_6$-$X_7$-β$A_8$-$X_9$-$W_{10}$-$X_{11}$-$C_{12}$ (SEQ ID NO: 6), $X_1$-$P_2$-$X_3$-$C_4$-$X_5$-$X_6$-$X_7$-β$A_8$-$X_9$-$W_{10}$-$X_{11}$-$C_{12}$ (SEQ ID NO: 7) or $X_1$-$P_2$-$X_3$-$C_4$-$X_5$-$X_6$-$X_7$-β$A_8$-$X_9$-$W_{10}$-$X_{11}$-$C_{12}$ (SEQ ID NO: 8), wherein $X_1$ is independently βA, D-A, A, E, G or Q; $X_3$ is independently Y, F, W, V, L or H; $X_5$ is independently V or L; $X_6$ is independently Y, F, W or H; $X_7$ is independently any amino acid except P; $X_9$ is independently any amino acid except P; and $X_{11}$ is independently any amino acid except P. Residues $C_4$ and $C_{12}$ of an APY cyclic peptide disclosed herein form a disulfide bridge. In an aspect of this embodiment, residue $C_{12}$ is optionally amidated. In another aspect of this embodiment, the amino-terminal residue is optionally acetylated.

In aspects of this embodiment, an APY cyclic peptide has the sequence $X_1$-$P_2$-$X_3$-$C_4$-$X_5$-$X_6$-$X_7$-β$A_8$-$X_9$-$W_{10}$-$X_{11}$-$C_{12}$ (SEQ ID NO: 6), $P_2$-$X_3$-$C_4$-$X_5$-$X_6$-$X_7$-β$A_8$-$X_9$-$W_{10}$-$X_{11}$-$C_{12}$ (SEQ ID NO: 7) or $X_3$-$C_4$-$X_5$-$X_6$-$X_7$-β$A_8$-$X_9$-$W_{10}$-$X_{11}$-$C_{12}$ (SEQ ID NO: 8), wherein $X_1$ is independently βA, D-A, A, E, G or Q; $X_3$ is independently Y, F, W, V, L or H; $X_5$ is independently V or L; $X_6$ is independently Y, F, W or H; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$P_2$-$X_3$-$C_4$-$X_5$-$X_6$-$X_7$-β$A_8$-$X_9$-$W_{10}$-$X_{11}$-$C_{12}$ (SEQ ID NO: 6), $P_2$-$X_3$-$C_4$-$X_5$-$X_6$-$X_7$-β$A_8$-$X_9$-$W_{10}$-$X_{11}$-$C_{12}$ (SEQ ID NO: 7) or $X_3$-$C_4$-$X_5$-$X_6$-$X_7$-β$A_8$-$X_9$-$W_{10}$-$X_{11}$-$C_{12}$ (SEQ ID NO: 8), wherein $X_1$ is independently βA, D-A, A, E, G or Q; $X_3$ is independently Y, F, W, V, L or H; $X_5$ is independently V or L; $X_6$ is independently Y, F, W or H; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$X_3$-$C_4$-$X_5$-$X_6$-$X_7$-β$A_8$-$X_9$-$W_{10}$-$X_{11}$-$C_{12}$ (SEQ ID NO: 6), $P_2$-$X_3$-$C_4$-$X_5$-$X_6$-$X_7$-β$A_8$-$X_9$-$W_{10}$-$X_{11}$-$C_{12}$ (SEQ ID NO: 7) or $X_3$-$C_4$-$X_5$-$X_6$-$X_7$-β$A_8$-$X_9$-$W_{10}$-$X_{11}$-$C_{12}$ (SEQ ID NO: 8), wherein $X_1$ is independently βA, D-A, A, E, G or Q; $X_3$ is independently Y, F, W, V, L or H; $X_5$ is independently V or L; $X_6$ is independently Y, F, W or H; $X_7$ is independently R, T, N, D, S, or Q; $X_9$ is independently S, E, T, V, D, Y; and $X_{11}$ is independently S, E, L, N, K, V, I or H. In still other aspects of this embodiment, an APY cyclic peptide has the sequence $X_1$-$P_2$-$X_3$-$C_4$-$X_5$-$X_6$-$X_7$-β$A_8$-$X_9$-$W_{10}$-$X_{11}$-$C_{12}$ (SEQ ID NO: 6), $P_2$-$X_3$-$C_4$-$X_5$-$X_6$-$X_7$-β$A_8$-$X_9$-$W_{10}$-$X_{11}$-$C_{12}$ (SEQ ID NO: 7) or $X_3$-$C_4$-$X_5$-$X_6$-$X_7$-β$A_8$-$X_9$-$W_{10}$-$X_{11}$-$C_{12}$ (SEQ ID NO: 8), wherein $X_1$ is independently βA, D-A, A, E, G or Q; $X_3$ is independently Y, F, W, V, L or H; $X_5$ is independently V or L; $X_6$ is independently Y, F, W or H; $X_7$ is independently R, T, or N; $X_9$ is independently S, E, T or V; and $X_{11}$ is independently S, E, L or N.

In aspects of this embodiment, an APY cyclic peptide has the sequence $X_1$-$P_2$-$X_3$-$C_4$-$X_5$-$X_6$-$X_7$-β$A_8$-$X_9$-$W_{10}$-$X_{11}$-$C_{12}$ (SEQ ID NO: 6), $P_2$-$X_3$-$C_4$-$X_5$-$X_6$-$X_7$-β$A_8$-$X_9$-$W_{10}$-$X_{11}$-$C_{12}$ (SEQ ID NO: 7) or $X_3$-$C_4$-$X_5$-$X_6$-$X_7$-β$A_8$-$X_9$-$W_{10}$-$X_{11}$-$C_{12}$ (SEQ ID NO: 8), wherein $X_1$ is independently βA, D-A, A or E; $X_3$ is independently Y, F or W; $X_5$ is independently V or L; $X_6$ is independently Y, F or W; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$P_2$-$X_3$-$C_4$-$X_5$-$X_6$-$X_7$-β$A_8$-$X_9$-$W_{10}$-$X_{11}$-$C_{12}$ (SEQ ID NO: 6), $P_2$-$X_3$-$C_4$-$X_5$-$X_6$-$X_7$-β$A_8$-$X_9$-$W_{10}$-$X_{11}$-$C_{12}$ (SEQ ID NO: 7) or $X_3$-$C_4$-$X_5$-$X_6$-$X_7$-β$A_8$-$X_9$-$W_{10}$-$X_{11}$-$C_{12}$ (SEQ ID NO: 8), wherein $X_1$ is independently βA, D-A, A or E; $X_3$ is independently Y, F or W; $X_5$ is independently Y, F or W; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$X_3$-$C_4$-$X_5$-$X_6$-$X_7$-β$A_8$-$X_9$-$W_{10}$-$X_{11}$-$C_{12}$ (SEQ ID NO: 6), $P_2$-$X_3$-$C_4$-$X_5$-$X_6$-$X_7$-β$A_8$-$X_9$-$W_{10}$-$X_{11}$-$C_{12}$ (SEQ ID NO: 7) or $X_3$-$C_4$-$X_5$-$X_6$-$X_7$-β$A_8$-$X_9$-$W_{10}$-$X_{11}$-$C_{12}$ (SEQ ID NO: 8), wherein $X_1$ is independently βA, D-A, A or E; $X_3$ is independently Y, F or W; $X_5$ is independently V or L; $X_6$ is independently Y, F or W; $X_7$ is independently R, T, or N; $X_9$ is independently S, E, T or V; and $X_{11}$ is independently S, E, L or N.

In another embodiment, an APY cyclic peptide has the sequence $X_1$-$X_2$-$X_3$-$C_4$-$V_5$-$X_6$-$X_7$-$\beta A_8$-$X_9$-$W_{10}$-$X_{11}$-$C_{12}$ (SEQ ID NO: 9), $X_2$-$X_3$-$C_4$-$V_5$-$X_6$-$X_7$-$\beta A_8$-$X_9$-$W_{10}$-$X_{11}$-$C_{12}$ (SEQ ID NO: 10) or $X_3$-$C_4$-$V_5$-$X_6$-$X_7$-$\beta A_8$-$X_9$-$W_{10}$-$X_{11}$-$C_{12}$ (SEQ ID NO: 11), wherein $X_1$ is independently $\beta A$, D-A, A, E, G or Q; $X_2$ is independently P, A, G, Ahx, Ava, γAbu, βA or Sar; $X_3$ is independently Y, F, W, V, L or H; $X_6$ is independently Y, F, W or H; $X_7$ is independently any amino acid except P; $X_9$ is independently any amino acid except P; and $X_{11}$ is independently any amino acid except P. Residues $C_4$ and $C_{12}$ of an APY cyclic peptide disclosed herein form a disulfide bridge. In an aspect of this embodiment, residue $C_{12}$ is optionally amidated. In another aspect of this embodiment, the amino-terminal residue is optionally acetylated.

In aspects of this embodiment, an APY cyclic peptide has the sequence $X_1$-$X_2$-$X_3$-$C_4$-$V_5$-$X_6$-$X_7$-$\beta A_8$-$X_9$-$W_{10}$-$X_{11}$-$C_{12}$ (SEQ ID NO: 9), $X_2$-$X_3$-$C_4$-$V_5$-$X_6$-$X_7$-$\beta A_8$-$X_9$-$W_{10}$-$X_{11}$-$C_{12}$ (SEQ ID NO: 10) or $X_3$-$C_4$-$V_5$-$X_6$-$X_7$-$\beta A_8$-$X_9$-$W_{10}$-$X_{11}$-$C_{12}$ (SEQ ID NO: 11), wherein $X_1$ is independently $\beta A$, D-A, A, E, G or Q; $X_2$ is independently P or A; $X_3$ is independently Y, F, W, V, L or H; $X_6$ is independently Y, F, W or H; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$X_2$-$X_3$-$C_4$-$V_5$-$X_6$-$X_7$-$\beta A_8$-$X_9$-$W_{10}$-$X_{11}$-$C_{12}$ (SEQ ID NO: 9), $X_2$-$X_3$-$C_4$-$V_5$-$X_6$-$X_7$-$\beta A_8$-$X_9$-$W_{10}$-$X_{11}$-$C_{12}$ (SEQ ID NO: 10) or $X_3$-$C_4$-$V_5$-$X_6$-$X_7$-$\beta A_8$-$X_9$-$W_{10}$-$X_{11}$-$C_{12}$ (SEQ ID NO: 11), wherein $X_1$ is independently $\beta A$, D-A, A, E, G or Q; $X_2$ is independently P or A; $X_3$ is independently Y, F, W, V, L or H; $X_6$ is independently Y, F, W or H; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$X_2$-$X_3$-$C_4$-$V_5$-$X_6$-$X_7$-$\beta A_8$-$X_9$-$W_{10}$-$X_{11}$-$C_{12}$ (SEQ ID NO: 9), $X_2$-$X_3$-$C_4$-$V_5$-$X_6$-$X_7$-$\beta A_8$-$X_9$-$W_{10}$-$X_{11}$-$C_{12}$ (SEQ ID NO: 10) or $X_3$-$C_4$-$V_5$-$X_6$-$X_7$-$\beta A_8$-$X_9$-$W_{10}$-$X_{11}$-$C_{12}$ (SEQ ID NO: 11), wherein $X_1$ is independently $\beta A$, D-A, A, E, G or Q; $X_2$ is independently P or A; $X_3$ is independently Y, F, W, V, L or H; $X_6$ is independently Y, F, W or H; $X_7$ is independently R, T, N, D, S, or Q; $X_9$ is independently S, E, T, V, D, Y; and $X_{11}$ is independently S, E, L, N, K, V, I or H. In still other aspects of this embodiment, an APY cyclic peptide has the sequence $X_1$-$X_2$-$X_3$-$C_4$-$V_5$-$X_6$-$X_7$-$\beta A_8$-$X_9$-$W_{10}$-$X_{11}$-$C_{12}$ (SEQ ID NO: 9), $X_2$-$X_3$-$C_4$-$V_5$-$X_6$-$X_7$-$\beta A_8$-$X_9$-$W_{10}$-$X_{11}$-$C_{12}$ (SEQ ID NO: 10) or $X_3$-$C_4$-$V_5$-$X_6$-$X_7$-$\beta A_8$-$X_9$-$W_{10}$-$X_{11}$-$C_{12}$ (SEQ ID NO: 11), wherein $X_1$ is independently $\beta A$, D-A, A or E; $X_2$ is independently P or A; $X_3$ is independently Y, F or W; $X_6$ is independently Y, F or W; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$X_2$-$X_3$-$C_4$-$V_5$-$X_6$-$X_7$-$\beta A_8$-$X_9$-$W_{10}$-$X_{11}$-$C_{12}$ (SEQ ID NO: 9), $X_2$-$X_3$-$C_4$-$V_5$-$X_6$-$X_7$-$\beta A_8$-$X_9$-$W_{10}$-$X_{11}$-$C_{12}$ (SEQ ID NO: 10) or $X_3$-$C_4$-$V_5$-$X_6$-$X_7$-$\beta A_8$-$X_9$-$W_{10}$-$X_{11}$-$C_{12}$ (SEQ ID NO: 11), wherein $X_1$ is independently $\beta A$, D-A, A or E; $X_2$ is independently P or A; $X_3$ is independently Y, F or W; $X_6$ is independently Y, F or W; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$X_2$-$X_3$-$C_4$-$V_5$-$X_6$-$X_7$-$\beta A_8$-$X_9$-$W_{10}$-$X_{11}$-$C_{12}$ (SEQ ID NO: 9), $X_2$-$X_3$-$C_4$-$V_5$-$X_6$-$X_7$-$\beta A_8$-$X_9$-$W_{10}$-$X_{11}$-$C_{12}$ (SEQ ID NO: 10) or $X_3$-$C_4$-$V_5$-$X_6$-$X_7$-$\beta A_8$-$X_9$-$W_{10}$-$X_{11}$-$C_{12}$ (SEQ ID NO: 11), wherein $X_1$ is independently $\beta A$, D-A, A or E; $X_2$ is independently P or A; $X_3$ is independently Y, F or W; $X_6$ is independently Y, F or W; $X_7$ is independently R, T, N, D, S, or Q; $X_9$ is independently S, E, T, V, D, Y; and $X_{11}$ is independently S, E, L, N, K, V, I or H. In still other aspects of this embodiment, an APY cyclic peptide has the sequence $X_1$-$X_2$-$X_3$-$C_4$-$V_5$-$X_6$-$X_7$-$\beta A_8$-$X_9$-$W_{10}$-$X_{11}$-$C_{12}$ (SEQ ID NO: 9), $X_2$-$X_3$-$C_4$-$V_5$-$X_6$-$X_7$-$\beta A_8$-$X_9$-$W_{10}$-$X_{11}$-$C_{12}$ (SEQ ID NO: 10) or $X_3$-$C_4$-$V_5$-$X_6$-$X_7$-$\beta A_8$-$X_9$-$W_{10}$-$X_{11}$-$C_{12}$ (SEQ ID NO: 11), wherein $X_1$ is independently $\beta A$, D-A, A or E; $X_2$ is independently P or A; $X_3$ is independently Y, F or W; $X_6$ is independently Y, F or W; $X_7$ is independently R, T, or N; $X_9$ is independently S, E, T or V; and $X_{11}$ is independently S, E, L or N.

In another embodiment, an APY cyclic peptide has the sequence $X_1$-$P_2$-$X_3$-$C_4$-$V_5$-$X_6$-$X_7$-$\beta A_8$-$X_9$-$W_{10}$-$X_{11}$-$C_{12}$ (SEQ ID NO: 12), $P_2$-$X_3$-$C_4$-$V_5$-$X_6$-$X_7$-$\beta A_8$-$X_9$-$W_{10}$-$X_{11}$-$C_{12}$ (SEQ ID NO: 13) or $X_3$-$C_4$-$V_5$-$X_6$-$X_7$-$\beta A_8$-$X_9$-$W_{10}$-$X_{11}$-$C_{12}$ (SEQ ID NO: 14), wherein $X_1$ is independently $\beta A$, D-A, A, E, G or Q; $X_3$ is independently Y, F, W, V, L or H; $X_6$ is independently Y, F, W or H; $X_7$ is independently any amino acid except P; $X_9$ is independently any amino acid except P; and $X_{11}$ is independently any amino acid except P. Residues $C_4$ and $C_{12}$ of an APY cyclic peptide disclosed herein form a disulfide bridge. In an aspect of this embodiment, residue $C_{12}$ is optionally amidated. In another aspect of this embodiment, the amino-terminal residue is optionally acetylated.

In aspects of this embodiment, an APY cyclic peptide has the sequence $X_1$-$P_2$-$X_3$-$C_4$-$V_5$-$X_6$-$X_7$-$\beta A_8$-$X_9$-$W_{10}$-$X_{11}$-$C_{12}$ (SEQ ID NO: 12), $P_2$-$X_3$-$C_4$-$V_5$-$X_6$-$X_7$-$\beta A_8$-$X_9$-$W_{10}$-$X_{11}$-$C_{12}$ (SEQ ID NO: 13) or $X_3$-$C_4$-$V_5$-$X_6$-$X_7$-$\beta A_8$-$X_9$-$W_{10}$-$X_{11}$-$C_{12}$ (SEQ ID NO: 14), wherein $X_1$ is independently $\beta A$, D-A, A, E, G or Q; $X_3$ is independently Y, F, W, V, L or H; $X_6$ is independently Y, F, W or H; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$P_2$-$X_3$-$C_4$-$V_5$-$X_6$-$X_7$-$\beta A_8$-$X_9$-$W_{10}$-$X_{11}$-$C_{12}$ (SEQ ID NO: 12), $P_2$-$X_3$-$C_4$-$V_5$-$X_6$-$X_7$-$\beta A_8$-$X_9$-$W_{10}$-$X_{11}$-$C_{12}$ (SEQ ID NO: 13) or $X_3$-$C_4$-$V_5$-$X_6$-$X_7$-$\beta A_8$-$X_9$-$W_{10}$-$X_{11}$-$C_{12}$ (SEQ ID NO: 14), wherein $X_1$ is independently $\beta A$, D-A, A, E, G or Q; $X_3$ is independently Y, F, W, V, L or H; $X_6$ is independently Y, F, W or H; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$X_3$-$C_4$-$V_5$-$X_6$-$X_7$-$\beta A_8$-$X_9$-$W_{10}$-$X_{11}$-$C_{12}$ (SEQ ID NO: 12), $P_2$-$X_3$-$C_4$-$V_5$-$X_6$-$X_7$-$\beta A_8$-$X_9$-$W_{10}$-$X_{11}$-$C_{12}$ (SEQ ID NO: 13) or $X_3$-$C_4$-$V_5$-$X_6$-$X_7$-$\beta A_8$-$X_9$-$W_{10}$-$X_{11}$-$C_{12}$ (SEQ ID NO: 14), wherein $X_1$ is independently $\beta A$, D-A, A, E, G or Q; $X_3$ is independently Y, F, W, V, L or H; $X_6$ is independently Y, F, W or H; $X_7$ is independently R, T, N, D, S, or Q; $X_9$ is independently S, E, T, V, D, Y; and $X_{11}$ is independently S, E, L, N, K, V, I or H. In still other aspects of this embodiment, an APY cyclic peptide has the sequence $X_1$-$P_2$-$X_3$-$C_4$-$V_5$-$X_6$-$X_7$-$\beta A_8$-$X_9$-$W_{10}$-$X_{11}$-$C_{12}$ (SEQ ID NO: 12), $P_2$-$X_3$-$C_4$-$V_5$-$X_6$-$X_7$-$\beta A_8$-$X_9$-$W_{10}$-$X_{11}$-$C_{12}$ (SEQ ID NO: 13) or $X_3$-$C_4$-$V_5$-$X_6$-$X_7$-$\beta A_8$-$X_9$-$W_{10}$-$X_{11}$-$C_{12}$ (SEQ ID NO: 14), wherein $X_1$ is independently βA, D-A, A, E, G or Q; $X_3$ is independently Y, F, W, V, L or H; $X_6$ is independently Y, F, W or H; $X_7$ is independently R, T, or N; $X_9$ is independently S, E, T or V; and $X_{11}$ is independently S, E, L or N.

In aspects of this embodiment, an APY cyclic peptide has the sequence $X_1$-$P_2$-$X_3$-$C_4$-$V_5$-$X_6$-$X_7$-$\beta A_8$-$X_9$-$W_{10}$-$X_{11}$-$C_{12}$ (SEQ ID NO: 12), $P_2$-$X_3$-$C_4$-$V_5$-$X_6$-$X_7$-$\beta A_8$-$X_9$-$W_{10}$-$X_{11}$-$C_{12}$ (SEQ ID NO: 13) or $X_3$-$C_4$-$V_5$-$X_6$-$X_7$-$\beta A_8$-$X_9$-$W_{10}$-$X_{11}$-$C_{12}$ (SEQ ID NO: 14), wherein $X_1$ is independently βA, D-A, A or E; $X_3$ is independently Y, F or W; $X_6$ is independently Y, F or W; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$P_2$-$X_3$-$C_4$-$V_5$-$X_6$-$X_7$-$\beta A_8$-$X_9$-$W_{10}$-$X_{11}$-$C_{12}$ (SEQ ID NO: 12), $P_2$-$X_3$-$C_4$-$V_5$-$X_6$-$X_7$-$\beta A_8$-$X_9$-$W_{10}$-$X_{11}$-$C_{12}$ (SEQ ID NO: 13) or $X_3$-$C_4$-$V_5$-$X_6$-$X_7$-$\beta A_8$-$X_9$-$W_{10}$-$X_{11}$-$C_{12}$ (SEQ ID NO: 14), wherein $X_1$ is independently βA, D-A, A or E; $X_3$ is independently Y, F or W; $X_6$ is independently Y, F or W; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$X_3$-$C_4$-$V_5$-$X_6$-$X_7$-$\beta A_8$-$X_9$-$W_{10}$-$X_{11}$-$C_{12}$ (SEQ ID NO: 12), $P_2$-$X_3$-$C_4$-$V_5$-$X_6$-$X_7$-$\beta A_8$-$X_9$-$W_{10}$-$X_{11}$-$C_{12}$ (SEQ ID NO: 13) or $X_3$-$C_4$-$V_5$-$X_6$-$X_7$-$\beta A_8$-$X_9$-$W_{10}$-$X_{11}$-$C_{12}$ (SEQ ID NO: 14), wherein $X_1$ is independently βA, D-A, A or E; $X_3$ is independently Y, F or W; $X_6$ is independently Y, F or W; $X_7$ is independently R, T, N, D, S, or Q; $X_9$ is independently S, E, T, V, D, Y; and $X_{11}$ is independently S, E, L, N, K, V, I or H. In still other aspects of this embodiment, an APY cyclic peptide has the sequence $X_1$-$P_2$-$X_3$-$C_4$-$V_5$-$X_6$-$X_7$-$\beta A_8$-$X_9$-$W_{10}$-$X_{11}$-$C_{12}$ (SEQ ID NO: 12), $P_2$-$X_3$-$C_4$-$V_5$-$X_6$-$X_7$-$\beta A_8$-$X_9$-$W_{10}$-$X_{11}$-$C_{12}$ (SEQ ID NO: 13) or $X_3$-$C_4$-$V_5$-$X_6$-$X_7$-$\beta A_8$-$X_9$-$W_{10}$-$X_{11}$-$C_{12}$ (SEQ ID NO: 14), wherein $X_1$ is independently βA, D-A, A or E; $X_3$ is independently Y, F or W; $X_6$ is independently Y, F or W; $X_7$ is independently R, T, or N; $X_9$ is independently S, E, T or V; and $X_{11}$ is independently S, E, L or N.

In another embodiment, an APY cyclic peptide has the sequence $X_1$-$P_2$-$Y_3$-$C_4$-$V_5$-$X_6$-$X_7$-$\beta A_8$-$X_9$-$W_{10}$-$X_{11}$-$C_{12}$ (SEQ ID NO: 15), $P_2$-$Y_3$-$C_4$-$V_5$-$X_6$-$X_7$-$\beta A_8$-$X_9$-$W_{10}$-$X_{11}$-$C_{12}$ (SEQ ID NO: 16), $Y_3$-$C_4$-$V_5$-$X_6$-$X_7$-$\beta A_8$-$X_9$-$W_{10}$-$X_{11}$-$C_{12}$ (SEQ ID NO: 17), wherein $X_1$ is independently βA, D-A, A, E, G or Q; $X_6$ is independently Y, F, W or H; $X_7$ is independently any amino acid except P; $X_9$ is independently any amino acid except P; and $X_{11}$ is independently any amino acid except P. Residues $C_4$ and $C_{12}$ of an APY cyclic peptide disclosed herein form a disulfide bridge. In an aspect of this embodiment, residue $C_{12}$ is optionally amidated. In another aspect of this embodiment, the amino-terminal residue is optionally acetylated.

In aspects of this embodiment, an APY cyclic peptide has the sequence $X_1$-$P_2$-$Y_3$-$C_4$-$V_5$-$X_6$-$X_7$-$\beta A_8$-$X_9$-$W_{10}$-$X_{11}$-$C_{12}$ (SEQ ID NO: 15), $P_2$-$Y_3$-$C_4$-$V_5$-$X_6$-$X_7$-$\beta A_8$-$X_9$-$W_{10}$-$X_{11}$-$C_{12}$ (SEQ ID NO: 16), $Y_3$-$C_4$-$V_5$-$X_6$-$X_7$-$\beta A_8$-$X_9$-$W_{10}$-$X_{11}$-$C_{12}$ (SEQ ID NO: 17), wherein $X_1$ is independently βA, D-A, A, E, G or Q; $X_6$ is independently Y, F, W or H; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$P_2$-$Y_3$-$C_4$-$V_5$-$X_6$-$X_7$-$\beta A_8$-$X_9$-$W_{10}$-$X_{11}$-$C_{12}$ (SEQ ID NO: 15), $P_2$-$Y_3$-$C_4$-$V_5$-$X_6$-$X_7$-$\beta A_8$-$X_9$-$W_{10}$-$X_{11}$-$C_{12}$ (SEQ ID NO: 16), $Y_3$-$C_4$-$V_5$-$X_6$-$X_7$-$\beta A_8$-$X_9$-$W_{10}$-$X_{11}$-$C_{12}$ (SEQ ID NO: 17), wherein $X_1$ is independently βA, D-A, A, E, G or Q; $X_6$ is independently Y, F, W or H; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$Y_3$-$C_4$-$V_5$-$X_6$-$X_7$-$\beta A_8$-$X_9$-$W_{10}$-$X_{11}$-$C_{12}$ (SEQ ID NO: 15), $P_2$-$Y_3$-$C_4$-$V_5$-$X_6$-$X_7$-$\beta A_8$-$X_9$-$W_{10}$-$X_{11}$-$C_{12}$ (SEQ ID NO: 16), $Y_3$-$C_4$-$V_5$-$X_6$-$X_7$-$\beta A_8$-$X_9$-$W_{10}$-$X_{11}$-$C_{12}$ (SEQ ID NO: 17), wherein $X_1$ is independently βA, D-A, A, E, G or Q; $X_6$ is independently Y, F, W or H; $X_7$ is independently R, T, N, D, S, or Q; $X_9$ is independently S, E, T, V, D, Y; and $X_{11}$ is independently S, E, L, N, K, V, I or H. In still other aspects of this embodiment, an APY cyclic peptide has the sequence $X_1$-$P_2$-$Y_3$-$C_4$-$V_5$-$X_6$-$X_7$-$\beta A_8$-$X_9$-$W_{10}$-$X_{11}$-$C_{12}$ (SEQ ID NO: 15), $P_2$-$Y_3$-$C_4$-$V_5$-$X_6$-$X_7$-$\beta A_8$-$X_9$-$W_{10}$-$X_{11}$-$C_{12}$ (SEQ ID NO: 16), $Y_3$-$C_4$-$V_5$-$X_6$-$X_7$-$\beta A_8$-$X_9$-$W_{10}$-$X_{11}$-$C_{12}$ (SEQ ID NO: 17), wherein $X_1$ is independently βA, D-A, A, E, G or Q; $X_6$ is independently Y, F, W or H; $X_7$ is independently R, T, or N; $X_9$ is independently S, E, T or V; and $X_{11}$ is independently S, E, L or N.

In aspects of this embodiment, an APY cyclic peptide has the sequence $X_1$-$P_2$-$Y_3$-$C_4$-$V_5$-$X_6$-$X_7$-$\beta A_8$-$X_9$-$W_{10}$-$X_{11}$-$C_{12}$ (SEQ ID NO: 15), $P_2$-$Y_3$-$C_4$-$V_5$-$X_6$-$X_7$-$\beta A_8$-$X_9$-$W_{10}$-$X_{11}$-$C_{12}$ (SEQ ID NO: 16), $Y_3$-$C_4$-$V_5$-$X_6$-$X_7$-$\beta A_8$-$X_9$-$W_{10}$-$X_{11}$-$C_{12}$ (SEQ ID NO: 17), wherein $X_1$ is independently βA, D-A, A or E; $X_6$ is independently Y, F or W; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$P_2$-$Y_3$-$C_4$-$V_6$-$X_6$-$X_7$-$\beta A_8$-$X_9$-$W_{10}$-$X_{11}$-$C_{12}$ (SEQ ID NO: 15), $P_2$-$Y_3$-$C_4$-$V_6$-$X_6$-$X_7$-$\beta A_8$-$X_9$-$W_{10}$-$X_{11}$-$C_{12}$ (SEQ ID NO: 16), $Y_3$-$C_4$-$V_6$-$X_6$-$X_7$-$\beta A_8$-$X_9$-$W_{10}$-$X_{11}$-$C_{12}$ (SEQ ID NO: 17), wherein $X_1$ is independently βA, D-A, A or E; $X_6$ is independently Y, F or W; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$Y_3$-$C_4$-$V_6$-$X_6$-$X_7$-$\beta A_8$-$X_9$-$W_{10}$-$X_{11}$-$C_{12}$ (SEQ ID NO: 15), $P_2$-$Y_3$-$C_4$-$V_6$-$X_6$-$X_7$-$\beta A_8$-$X_9$-$W_{10}$-$X_{11}$-$C_{12}$ (SEQ ID NO: 16), $Y_3$-$C_4$-$V_6$-$X_6$-$X_7$-$\beta A_8$-$X_9$-$W_{10}$-$X_{11}$-$C_{12}$ (SEQ ID NO: 17), wherein $X_1$ is independently βA, D-A, A or E; $X_6$ is independently Y, F or W; $X_7$ is independently R, T, N, D, S, or Q; $X_9$ is independently S, E, T, V, D, Y; and $X_{11}$ is independently S, E, L, N, K, V, I or H. In still other aspects of this embodiment, an APY cyclic peptide has the sequence $X_1$-$P_2$-$Y_3$-$C_4$-$V_6$-$X_6$-$X_7$-$\beta A_8$-$X_9$-$W_{10}$-$X_{11}$-$C_{12}$ (SEQ ID NO: 15), $P_2$-$Y_3$-$C_4$-$V_6$-$X_6$-$X_7$-$\beta A_8$-$X_9$-$W_{10}$-$X_{11}$-$C_{12}$ (SEQ ID NO: 16), $Y_3$-$C_4$-$V_6$-$X_6$-$X_7$-$\beta A_8$-$X_9$-$W_{10}$-$X_{11}$-$C_{12}$ (SEQ ID NO: 17), wherein $X_1$ is independently βA, D-A, A or E; $X_6$ is independently Y, F or W; $X_7$ is independently R, T, or N; $X_9$ is independently S, E, T or V; and $X_{11}$ is independently S, E, L or N.

In another embodiment, an APY cyclic peptide has the sequence $X_1$-$P_2$-$X_3$-$C_4$-$V_5$-$Y_6$-$X_7$-$\beta A_8$-$X_9$-$W_{10}$-$X_{11}$-$C_{12}$ (SEQ ID NO: 18), $P_2$-$X_3$-$C_4$-$V_5$-$Y_6$-$X_7$-$\beta A_8$-$X_9$-$W_{10}$-$X_{11}$-$C_{12}$ (SEQ ID NO: 19) or $X_3$-$C_4$-$V_5$-$Y_6$-$X_7$-$\beta A_8$-$X_9$-$W_{10}$-$X_{11}$-$C_{12}$ (SEQ ID NO: 20), wherein $X_1$ is independently βA, D-A, A, E, G or Q; $X_3$ is independently Y, F, W, V, L or H;

$X_7$ is independently any amino acid except P; $X_9$ is independently any amino acid except P; and $X_{11}$ is independently any amino acid except P. Residues $C_4$ and $C_{12}$ of an APY cyclic peptide disclosed herein form a disulfide bridge. In an aspect of this embodiment, residue $C_{12}$ is optionally amidated. In another aspect of this embodiment, the amino-terminal residue is optionally acetylated.

In aspects of this embodiment, an APY cyclic peptide has the sequence $X_1$-$P_2$-$X_3$-$C_4$-$V_5$-$Y_6$-$X_7$-$\beta A_8$-$X_9$-$W_{10}$-$X_{11}$-$C_{12}$ (SEQ ID NO: 18), $P_2$-$X_3$-$C_4$-$V_5$-$Y_6$-$X_7$-$\beta A_8$-$X_9$-$W_{10}$-$X_{11}$-$C_{12}$ (SEQ ID NO: 19) or $X_3$-$C_4$-$V_5$-$Y_6$-$X_7$-$\beta A_8$-$X_9$-$W_{10}$-$X_{11}$-$C_{12}$ (SEQ ID NO: 20), wherein $X_1$ is independently $\beta A$, D-A, A, E, G or Q; $X_3$ is independently Y, F, W, V, L or H; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$P_2$-$X_3$-$C_4$-$V_5$-$Y_6$-$X_7$-$\beta A_8$-$X_9$-$W_{10}$-$X_{11}$-$C_{12}$ (SEQ ID NO: 18), $P_2$-$X_3$-$C_4$-$V_5$-$Y_6$-$X_7$-$\beta A_8$-$X_9$-$W_{10}$-$X_{11}$-$C_{12}$ (SEQ ID NO: 19) or $X_3$-$C_4$-$V_5$-$Y_6$-$X_7$-$\beta A_8$-$X_9$-$W_{10}$-$X_{11}$-$C_{12}$ (SEQ ID NO: 20), wherein $X_1$ is independently $\beta A$, D-A, A, E, G or Q; $X_3$ is independently Y, F, W, V, L or H; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$X_3$-$C_4$-$V_5$-$Y_6$-$X_7$-$\beta A_8$-$X_9$-$W_{10}$-$X_{11}$-$C_{12}$ (SEQ ID NO: 18), $P_2$-$X_3$-$C_4$-$V_5$-$Y_6$-$X_7$-$\beta A_8$-$X_9$-$W_{10}$-$X_{11}$-$C_{12}$ (SEQ ID NO: 19) or $X_3$-$C_4$-$V_5$-$Y_6$-$X_7$-$\beta A_8$-$X_9$-$W_{10}$-$X_{11}$-$C_{12}$ (SEQ ID NO: 20), wherein $X_1$ is independently $\beta A$, D-A, A, E, G or Q; $X_3$ is independently Y, F, W, V, L or H; $X_7$ is independently R, T, N, D, S, or Q; $X_9$ is independently S, E, T, V, D, Y; and $X_{11}$ is independently S, E, L, N, K, V, I or H. In still other aspects of this embodiment, an APY cyclic peptide has the sequence $X_1$-$P_2$-$X_3$-$C_4$-$V_5$-$Y_6$-$X_7$-$\beta A_8$-$X_9$-$W_{10}$-$X_{11}$-$C_{12}$ (SEQ ID NO: 18), $P_2$-$X_3$-$C_4$-$V_5$-$Y_6$-$X_7$-$\beta A_8$-$X_9$-$W_{10}$-$X_{11}$-$C_{12}$ (SEQ ID NO: 19) or $X_3$-$C_4$-$V_5$-$Y_6$-$X_7$-$\beta A_8$-$X_9$-$W_{10}$-$X_{11}$-$C_{12}$ (SEQ ID NO: 20), wherein $X_1$ is independently $\beta A$, D-A, A, E, G or Q; $X_3$ is independently Y, F, W, V, L or H; $X_7$ is independently R, T, or N; $X_9$ is independently S, E, T or V; and $X_{11}$ is independently S, E, L or N.

In aspects of this embodiment, an APY cyclic peptide has the sequence $X_1$-$P_2$-$X_3$-$C_4$-$V_5$-$Y_6$-$X_7$-$\beta A_8$-$X_9$-$W_{10}$-$X_{11}$-$C_{12}$ (SEQ ID NO: 18), $P_2$-$X_3$-$C_4$-$V_5$-$Y_6$-$X_7$-$\beta A_8$-$X_9$-$W_{10}$-$X_{11}$-$C_{12}$ (SEQ ID NO: 19) or $X_3$-$C_4$-$V_5$-$Y_6$-$X_7$-$\beta A_8$-$X_9$-$W_{10}$-$X_{11}$-$C_{12}$ (SEQ ID NO: 20), wherein $X_1$ is independently $\beta A$, D-A, A or E; $X_3$ is independently Y, F or W; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$P_2$-$X_3$-$C_4$-$V_5$-$Y_6$-$X_7$-$\beta A_8$-$X_9$-$W_{10}$-$X_{11}$-$C_{12}$ (SEQ ID NO: 18), $P_2$-$X_3$-$C_4$-$V_5$-$Y_6$-$X_7$-$\beta A_8$-$X_9$-$W_{10}$-$X_{11}$-$C_{12}$ (SEQ ID NO: 19) or $X_3$-$C_4$-$V_5$-$Y_6$-$X_7$-$\beta A_8$-$X_9$-$W_{10}$-$X_{11}$-$C_{12}$ (SEQ ID NO: 20), wherein $X_1$ is independently $\beta A$, D-A, A or E; $X_3$ is independently Y, F or W; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$X_3$-$C_4$-$V_5$-$Y_6$-$X_7$-$\beta A_8$-$X_9$-$W_{10}$-$X_{11}$-$C_{12}$ (SEQ ID NO: 18), $P_2$-$X_3$-$C_4$-$V_5$-$Y_6$-$X_7$-$\beta A_8$-$X_9$-$W_{10}$-$X_{11}$-$C_{12}$ (SEQ ID NO: 19) or $X_3$-$C_4$-$V_5$-$Y_6$-$X_7$-$\beta A_8$-$X_9$-$W_{10}$-$X_{11}$-$C_{12}$ (SEQ ID NO: 20), wherein $X_1$ is independently $\beta A$, D-A, A or E; $X_3$ is independently Y, F or W; $X_7$ is independently R, T, N, D, S, or Q; $X_9$ is independently S, E, T, V, D, Y; and $X_{11}$ is independently S, E, L, N, K, V, I or H. In still other aspects of this embodiment, an APY cyclic peptide has the sequence $X_1$-$P_2$-$X_3$-$C_4$-$V_5$-$Y_6$-$X_7$-$\beta A_8$-$X_9$-$W_{10}$-$X_{11}$-$C_{12}$ (SEQ ID NO: 18), $P_2$-$X_3$-$C_4$-$V_5$-$Y_6$-$X_7$-$\beta A_8$-$X_9$-$W_{10}$-$X_{11}$-$C_{12}$ (SEQ ID NO: 19) or $X_3$-$C_4$-$V_5$-$Y_6$-$X_7$-$\beta A_8$-$X_9$-$W_{10}$-$X_{11}$-$C_{12}$ (SEQ ID NO: 20), wherein $X_1$ is independently $\beta A$, D-A, A or E; $X_3$ is independently Y, F or W; $X_7$ is independently R, T, or N; $X_9$ is independently S, E, T or V; and $X_{11}$ is independently S, E, L or N.

In another embodiment, an APY cyclic peptide has the sequence $X_1$-$P_2$-$Y_3$-$C_4$-$V_5$-$Y_6$-$X_7$-$\beta A_8$-$X_9$-$W_{10}$-$X_{11}$-$C_{12}$ (SEQ ID NO: 21), $P_2$-$Y_3$-$C_4$-$V_5$-$Y_6$-$X_7$-$\beta A_8$-$X_9$-$W_{10}$-$X_{11}$-$C_{12}$ (SEQ ID NO: 22) or $Y_3$-$C_4$-$V_5$-$Y_6$-$X_7$-$\beta A_8$-$X_9$-$W_{10}$-$X_{11}$-$C_{12}$ (SEQ ID NO: 23), wherein $X_1$ is independently $\beta A$, D-A, A, E, G or Q; $X_7$ is independently any amino acid except P; $X_9$ is independently any amino acid except P; and $X_{11}$ is independently any amino acid except P. Residues $C_4$ and $C_{12}$ of an APY cyclic peptide disclosed herein form a disulfide bridge. In an aspect of this embodiment, residue $C_{12}$ is optionally amidated. In another aspect of this embodiment, the amino-terminal residue is optionally acetylated.

In aspects of this embodiment, an APY cyclic peptide has the sequence $X_1$-$P_2$-$Y_3$-$C_4$-$V_5$-$Y_6$-$X_7$-$\beta A_8$-$X_9$-$W_{10}$-$X_{11}$-$C_{12}$ (SEQ ID NO: 21), $P_2$-$Y_3$-$C_4$-$V_5$-$Y_6$-$X_7$-$\beta A_8$-$X_9$-$W_{10}$-$X_{11}$-$C_{12}$ (SEQ ID NO: 22) or $Y_3$-$C_4$-$V_5$-$Y_6$-$X_7$-$\beta A_8$-$X_9$-$W_{10}$-$X_{11}$-$C_{12}$ (SEQ ID NO: 23), wherein $X_1$ is independently $\beta A$, D-A, A, E, G or Q; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$P_2$-$Y_3$-$C_4$-$V_5$-$Y_6$-$X_7$-$\beta A_8$-$X_9$-$W_{10}$-$X_{11}$-$C_{12}$ (SEQ ID NO: 21), $P_2$-$Y_3$-$C_4$-$V_5$-$Y_6$-$X_7$-$\beta A_8$-$X_9$-$W_{10}$-$X_{11}$-$C_{12}$ (SEQ ID NO: 22) or $Y_3$-$C_4$-$V_5$-$Y_6$-$X_7$-$\beta A_8$-$X_9$-$W_{10}$-$X_{11}$-$C_{12}$ (SEQ ID NO: 23), wherein $X_1$ is independently $\beta A$, D-A, A, E, G or Q; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$Y_3$-$C_4$-$V_5$-$Y_6$-$X_7$-$\beta A_8$-$X_9$-$W_{10}$-$X_{11}$-$C_{12}$ (SEQ ID NO: 21), $P_2$-$Y_3$-$C_4$-$V_5$-$Y_6$-$X_7$-$\beta A_8$-$X_9$-$W_{10}$-$X_{11}$-$C_{12}$ (SEQ ID NO: 22) or $Y_3$-$C_4$-$V_5$-$Y_6$-$X_7$-$\beta A_8$-$X_9$-$W_{10}$-$X_{11}$-$C_{12}$ (SEQ ID NO: 23), wherein $X_1$ is independently $\beta A$, D-A, A, E, G or Q; $X_7$ is independently R, T, N, D, S, or Q; $X_9$ is independently S, E, T, V, D, Y; and $X_{11}$ is independently S, E, L, N, K, V, I or H. In still other aspects of this embodiment, an APY cyclic peptide has the sequence $X_1$-$P_2$-$Y_3$-$C_4$-$V_5$-$Y_6$-$X_7$-$\beta A_8$-$X_9$-$W_{10}$-$X_{11}$-$C_{12}$ (SEQ ID NO: 21), $P_2$-$Y_3$-$C_4$-$V_5$-$Y_6$-$X_7$-$\beta A_8$-$X_9$-$W_{10}$-$X_{11}$-$C_{12}$ (SEQ ID NO: 22) or $Y_3$-$C_4$-$V_5$-$Y_6$-$X_7$-$\beta A_8$-$X_9$-$W_{10}$-$X_{11}$-$C_{12}$ (SEQ ID NO: 23), wherein $X_1$ is independently $\beta A$, D-A, A, E, G or Q; $X_7$ is independently R, T, or N; $X_9$ is independently S, E, T or V; and $X_{11}$ is independently S, E, L or N.

In aspects of this embodiment, an APY cyclic peptide has the sequence $X_1$-$P_2$-$Y_3$-$C_4$-$V_5$-$Y_6$-$X_7$-$\beta A_8$-$X_9$-$W_{10}$-$X_{11}$-$C_{12}$ (SEQ ID NO: 21), $P_2$-$Y_3$-$C_4$-$V_5$-$Y_6$-$X_7$-$\beta A_8$-$X_9$-$W_{10}$-$X_{11}$-$C_{12}$ (SEQ ID NO: 22) or $Y_3$-$C_4$-$V_5$-$Y_6$-$X_7$-$\beta A_8$-$X_9$-$W_{10}$-$X_{11}$-$C_{12}$ (SEQ ID NO: 23), wherein $X_1$ is independently $\beta A$, D-A, A or E; $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$P_2$-$Y_3$-$C_4$-$V_5$-$Y_6$-$X_7$-$\beta A_8$-$X_9$-$W_{10}$-$X_{11}$-$C_{12}$ (SEQ ID NO: 21), $P_2$-$Y_3$-$C_4$-$V_5$-$Y_6$-$X_7$-$\beta A_8$-$X_9$-$W_{10}$-$X_{11}$-$C_{12}$ (SEQ ID NO: 22) or $Y_3$-$C_4$-$V_5$-$Y_6$-$X_7$-$\beta A_8$-$X_9$-$W_{10}$-$X_{11}$-$C_{12}$ (SEQ ID NO: 23), wherein $X_1$ is independently $\beta A$, D-A, A or E; $X_7$ is independently R, T, N, D, S, or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$Y_3$-$C_4$-$V_5$-$Y_6$-$X_7$-$\beta A_8$-$X_9$-$W_{10}$-$X_{11}$-$C_{12}$ (SEQ ID NO: 21), $P_2$-$Y_3$-$C_4$-$V_5$-$Y_6$-$X_7$-$\beta A_8$-$X_9$-$W_{10}$-$X_{11}$-$C_{12}$ (SEQ ID NO: 22) or $Y_3$-$C_4$-$V_5$-$Y_6$-$X_7$-$\beta A_8$-$X_9$-$W_{10}$-$X_{11}$-$C_{12}$ (SEQ ID NO: 23), wherein $X_1$ is independently $\beta$A, D-A, A or E; $X_7$ is independently R, T, N, D, S, or Q; $X_9$ is independently S, E, T, V, D, Y; and $X_{11}$ is independently S, E, L, N, K, V, I or H. In still other aspects of this embodiment, an APY cyclic peptide has the sequence $X_1$-$P_2$-$Y_3$-$C_4$-$V_5$-$Y_6$-$X_7$-$\beta A_8$-$X_9$-$W_{10}$-$X_{11}$-$C_{12}$ (SEQ ID NO: 21), $P_2$-$Y_3$-$C_4$-$V_5$-$Y_6$-$X_7$-$\beta A_8$-$X_9$-$W_{10}$-$X_{11}$-$C_{12}$ (SEQ ID NO: 22) or $Y_3$-$C_4$-$V_5$-$Y_6$-$X_7$-$\beta A_8$-$X_9$-$W_{10}$-$X_{11}$-$C_{12}$ (SEQ ID NO: 23), wherein $X_1$ is independently $\beta$A, D-A, A or E; $X_7$ is independently R, T, or N; $X_9$ is independently S, E, T or V; and $X_{11}$ is independently S, E, L or N.

In another embodiment, an APY cyclic peptide has the sequence $X_1$-$P_2$-$Y_3$-$C_4$-$V_5$-$Y_6$-$R_7$-$\beta A_8$-$X_9$-$W_{10}$-$X_{11}$-$C_{12}$ (SEQ ID NO: 24), $P_2$-$Y_3$-$C_4$-$V_5$-$Y_6$-$R_7$-$\beta A_8$-$X_9$-$W_{10}$-$X_{11}$-$C_{12}$ (SEQ ID NO: 25) or $Y_3$-$C_4$-$V_5$-$Y_6$-$R_7$-$\beta A_8$-$X_9$-$W_{10}$-$X_{11}$-$C_{12}$ (SEQ ID NO: 26), wherein $X_1$ is independently $\beta$A, D-A, A, E, G or Q; $X_9$ is independently any amino acid except P; and $X_{11}$ is independently any amino acid except P. Residues $C_4$ and $C_{12}$ of an APY cyclic peptide disclosed herein form a disulfide bridge. In an aspect of this embodiment, residue $C_{12}$ is optionally amidated. In another aspect of this embodiment, the amino-terminal residue is optionally acetylated.

In aspects of this embodiment, an APY cyclic peptide has the sequence $X_1$-$P_2$-$Y_3$-$C_4$-$V_5$-$Y_6$-$R_7$-$\beta A_8$-$X_9$-$W_{10}$-$X_{11}$-$C_{12}$ (SEQ ID NO: 24), $P_2$-$Y_3$-$C_4$-$V_5$-$Y_6$-$R_7$-$\beta A_8$-$X_9$-$W_{10}$-$X_{11}$-$C_{12}$ (SEQ ID NO: 25) or $Y_3$-$C_4$-$V_5$-$Y_6$-$R_7$-$\beta A_8$-$X_9$-$W_{10}$-$X_{11}$-$C_{12}$ (SEQ ID NO: 26), wherein $X_1$ is independently $\beta$A, D-A, A, E, G or Q; $X_9$ is independently S, E, T, V, D, Y, Q, V, W, R, N, L, K or H; and $X_{11}$ is independently S, E, L, N, V, I, H, K, M, D, W, T or G. In other aspects of this embodiment, an APY cyclic peptide has the sequence $X_1$-$P_2$-$Y_3$-$C_4$-$V_5$-$Y_6$-$R_7\beta A_8$-$X_9$-$W_{10}$-$X_{11}$-$C_{12}$ (SEQ ID NO: 24), $P_2$-$Y_3$-$C_4$-$V_5$-$Y_6$-$R_7\beta A_8$-$X_9$-$W_{10}$-$X_{11}$-$C_{12}$ (SEQ ID NO: 25) or $Y_3$-$C_4$-$V_5$-$Y_6$-$R_7$-$\beta A_8$-$X_9$-$W_{10}$-$X_{11}$-$C_{12}$ (SEQ ID NO: 26), wherein $X_1$ is independently $\beta$A, D-A, A, E, G or Q; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$Y_3$-$C_4$-$V_5$-$Y_6$-$R_7$-$\beta A_8$-$X_9$-$W_{10}$-$X_{11}$-$C_{12}$ (SEQ ID NO: 24), $P_2$-$Y_3$-$C_4$-$V_5$-$Y_6$-$R_7$-$\beta A_8$-$X_9$-$W_{10}$-$X_{11}$-$C_{12}$ (SEQ ID NO: 25) or $Y_3$-$C_4$-$V_5$-$Y_6$-$R_7$-$\beta A_8$-$X_9$-$W_{10}$-$X_{11}$-$C_{12}$ (SEQ ID NO: 26), wherein $X_1$ is independently $\beta$A, D-A, A, E, G or Q; $X_9$ is independently S, E, T, V, D, Y; and $X_{11}$ is independently S, E, L, N, K, V, I or H. In still other aspects of this embodiment, an APY cyclic peptide has the sequence $X_1$-$P_2$-$Y_3$-$C_4$-$V_5$-$Y_6$-$R_7$-$\beta A_8$-$X_9$-$W_{10}$-$X_{11}$-$C_{12}$ (SEQ ID NO: 24), $P_2$-$Y_3$-$C_4$-$V_5$-$Y_6$-$R_7$-$\beta A_8$-$X_9$-$W_{10}$-$X_{11}$-$C_{12}$ (SEQ ID NO: 25) or $Y_3$-$C_4$-$V_5$-$Y_6$-$R_7$-$\beta A_8$-$X_9$-$W_{10}$-$X_{11}$-$C_{12}$ (SEQ ID NO: 26), wherein $X_1$ is independently $\beta$A, D-A, A, E, G or Q; $X_9$ is independently S, E, T or V; and $X_{11}$ is independently S, E, L or N.

In aspects of this embodiment, an APY cyclic peptide has the sequence $X_1$-$P_2$-$Y_3$-$C_4$-$V_5$-$Y_6$-$R_7$-$\beta A_8$-$X_9$-$W_{10}$-$X_{11}$-$C_{12}$ (SEQ ID NO: 24), $P_2$-$Y_3$-$C_4$-$V_5$-$Y_6$-$R_7$-$\beta A_8$-$X_9$-$W_{10}$-$X_{11}$-$C_{12}$ (SEQ ID NO: 25) or $Y_3$-$C_4$-$V_5$-$Y_6$-$R_7$-$\beta A_8$-$X_9$-$W_{10}$-$X_{11}$-$C_{12}$ (SEQ ID NO: 26), wherein $X_1$ is independently $\beta$A, D-A, A or E; $X_9$ is independently S, E, T, V, W, R, L, D, Y; and $X_{11}$ is independently S, E, L, N, T, K, V, I or H. In yet other aspects of this embodiment, an APY cyclic peptide has the sequence $X_1$-$P_2$-$Y_3$-$C_4$-$V_5$-$Y_6$-$R_7$-$\beta A_8$-$X_9$-$W_{10}$-$X_{11}$-$C_{12}$ (SEQ ID NO: 24), $P_2$-$Y_3$-$C_4$-$V_5$-$Y_6$-$R_7$-$\beta A_8$-$X_9$-$W_{10}$-$X_{11}$-$C_{12}$ (SEQ ID NO: 25) or $Y_3$-$C_4$-$V_5$-$Y_6$-$R_7$-$\beta A_8$-$X_9$-$W_{10}$-$X_{11}$-$C_{12}$ (SEQ ID NO: 26), wherein $X_1$ is independently $\beta$A, D-A, A or E; $X_9$ is independently S, E, T, V, D, Y; and $X_{11}$ is independently S, E, L, N, K, V, I or H. In still other aspects of this embodiment, an APY cyclic peptide has the sequence $X_1$-$P_2$-$Y_3$-$C_4$-$V_5$-$Y_6$-$R_7$-$\beta A_8$-$X_9$-$W_{10}$-$X_{11}$-$C_{12}$ (SEQ ID NO: 24), $P_2$-$Y_3$-$C_4$-$V_5$-$Y_6$-$R_7$- $\beta A_8$-$X_9$-$W_{10}$-$X_{11}$-$C_{12}$ (SEQ ID NO: 25) or $Y_3$-$C_4$-$V_5$-$Y_6$-$R_7$-$\beta A_8$-$X_9$-$W_{10}$-$X_{11}$-$C_{12}$ (SEQ ID NO: 26), wherein $X_1$ is independently $\beta$A, D-A, A or E; $X_9$ is independently S, E, T or V; and $X_{11}$ is independently S, E, L or N.

In another embodiment, an APY cyclic peptide has the sequence APYCVYR$\beta$ASWSC (SEQ ID NO: 35), APYCVYR$\beta$ASWSC-am (SEQ ID NO: 36), APYCVYK$\beta$ASWSC-am (SEQ ID NO: 45), $\beta$APYCVYR$\beta$ASWSC (SEQ ID NO: 46), $\beta$APYCVYR$\beta$ASWSC-am (SEQ ID NO: 47), $\beta$APYCVYK$\beta$ASWSC-am (SEQ ID NO: 48), $\beta$APYCVYR$\beta$AEWEC (SEQ ID NO: 49), $\beta$APYCVYR$\beta$AEWEC-am (SEQ ID NO: 50), D-APYCVYR$\beta$ASWSC (SEQ ID NO: 51), D-APYCVYR$\beta$ASWSC-am (SEQ ID NO: 52), APYCVWR$\beta$ASWSC (SEQ ID NO: 53), APYCVYT$\beta$AEWLC (SEQ ID NO: 54), APYCVYN$\beta$ATWNC (SEQ ID NO: 55), APYCVYR$\beta$AVWEC (SEQ ID NO: 56), APVCVWR$\beta$ASWSC (SEQ ID NO: 57), APLCVWR$\beta$ASWSC (SEQ ID NO: 58), APLCVYR$\beta$ASWSC (SEQ ID NO: 59), APWCVFR$\beta$ASWSC (SEQ ID NO: 60), APHCVFR$\beta$ASWSC (SEQ ID NO: 61), APFCLYT$\beta$ADWVC (SEQ ID NO: 62), APYCVYD$\beta$ATWIC (SEQ ID NO: 63), APYCVYS$\beta$ATWHC (SEQ ID NO: 64), APYCVYD$\beta$ASWNC (SEQ ID NO: 65), APYCVYQ$\beta$AYWKC (SEQ ID NO: 66), APYCVYR$\beta$ASWSC (SEQ ID NO: 67), EPYCVYR$\beta$ASWSC (SEQ ID NO: 68), APLCVYR$\beta$ASWSC (SEQ ID NO: 69), Ahx-YCVYR$\beta$ASWSC-am (SEQ ID NO: 119), Ava-YCVYR$\beta$ASWSC-am (SEQ ID NO: 120), $\gamma$Abu-YCVYR$\beta$ASWSC-am (SEQ ID NO: 121), $\beta$A-YCVYR$\beta$ASWSC-am (SEQ ID NO: 122), GYCVYR$\beta$ASWSC-am (SEQ ID NO: 123) or Sar1-Y-$\beta$Ala8.am (SEQ ID NO: 124). In aspects of this embodiment, an APY cyclic peptide has the sequence APYCVYR$\beta$ASWSC-am (SEQ ID NO: 36), APYCVYK$\beta$ASWSC-am (SEQ ID NO: 45), $\beta$APYCVYR$\beta$ASWSC (SEQ ID NO: 46), $\beta$APYCVYR$\beta$ASWSC-am (SEQ ID NO: 47), $\beta$APYCVYR$\beta$AEWEC-am (SEQ ID NO: 50), D-APYCVYR$\beta$ASWSC-am (SEQ ID NO: 52), APYCVWR$\beta$ASWSC (SEQ ID NO: 53), APYCVYT$\beta$AEWLC (SEQ ID NO: 54), APYCVYN$\beta$ATWNC (SEQ ID NO: 55) or APYCVYR$\beta$AVWEC (SEQ ID NO: 56). In other aspects of this embodiment, an APY cyclic peptide has the sequence APYCVYR$\beta$ASWSC-am (SEQ ID NO: 36), βAPYCVYRβASWSC-am (SEQ ID NO: 47) or βAPYCVYRβAEWEC-am (SEQ ID NO: 50).

Aspects of the present specification disclose, in part, an EphA4 antagonist, like an APY cyclic peptide disclosed herein, that selectively binds to the ephrin-binding pocket in the EphA4 ligand binding domain. Selective binding includes binding properties such as, e.g., binding affinity and binding specificity. Binding affinity refers to the length of time an EphA4 antagonist, like an APY cyclic peptide disclosed herein, resides at the ephrin-binding pocket in the EphA4 ligand binding domain, and can be viewed as the strength with which an EphA4 antagonist binds to the ephrin-binding pocket. Binding affinity can be described by EphA4 antagonist's equilibrium dissociation constant ($K_D$), which is defined as the ratio Kd/Ka at equilibrium. Where Ka is the EphA4 antagonist's association rate constant and kd is the EphA4 antagonist's dissociation rate constant. Binding affinity is determined by both the association and the dissociation and alone neither high association or low dissociation can ensure high affinity. The association rate constant (Ka), or on-rate constant (Kon), measures the number of binding events per unit time, or the propensity of the EphA4 antagonist and the ephrin-binding pocket in the EphA4 ligand binding domain to associate reversibly into its ligand-receptor complex. The association rate constant is expressed in M−1 s−1, and is symbolized as follows: [Ligand]×[Receptor]×Kon. The larger the association rate constant, the more rapidly the EphA4 antagonist binds to the ephrin-binding pocket in the EphA4 ligand binding domain, or the higher the binding affinity between an EphA4 antagonist and EphA4. The dissociation rate constant (Kd), or off-rate constant (Koff), measures the number of dissociation events per unit time propensity of an ligand-receptor complex to separate (dissociate) reversibly into its component molecules, namely the EphA4 antagonist and EphA4. The dissociation rate constant is expressed in s−1, and is symbolized as follows: [Ligand+Receptor]×Koff. The smaller the dissociation rate constant, the more tightly bound the EphA4 antagonist is to the ephrin-binding pocket in the EphA4 ligand binding domain, or the higher the binding affinity between an EphA4 antagonist and EphA4. The equilibrium dissociation constant ($K_D$) measures the rate at which new ligand-receptor complexes formed equals the rate at which ligand-receptor complexes dissociate at equilibrium. The equilibrium dissociation constant is expressed in M, and is defined as Koff/Kon=[Receptor]×[Ligand]/[Receptor+Ligand], where [Receptor] is the molar concentration of the receptor, [Ligand] is the molar concentration of the ligand, and [Receptor+Ligand] is the of molar concentration of the ligand-receptor complex, where all concentrations are of such components when the system is at equilibrium. The smaller the equilibrium dissociation constant, the more tightly bound the EphA4 antagonist is to the ephrin-binding pocket in the EphA4 ligand binding domain, or the higher the binding affinity between an EphA4 antagonist and EphA4.

Thus, in an embodiment, the binding affinity of an EphA4 antagonist, like an APY cyclic peptide disclosed herein, may have an association rate constant for an EpHA4 receptor of, e.g., less than $1\times10^5$ M$^{-1}$ s$^{-1}$, $5\times10^5$ M$^{-1}$ s$^{-1}$, less than $1\times10^6$ M$^{-1}$ s$^{-1}$, less than $5\times10^6$ M$^{-1}$ s$^{-1}$, less than $1\times10^7$ M$^{-1}$ s$^{-1}$, less than $5\times10^7$ M$^{-1}$ s$^{-1}$ or less than $1\times10^8$ M$^{-1}$ s$^{-1}$. In another embodiment, the binding affinity of an EphA4 antagonist, like an APY cyclic peptide disclosed herein, may an EphA4 antagonist, like an APY cyclic peptide disclosed herein, may have an association rate constant for an EpHA4 receptor of, e.g., more than $1\times10^5$ M$^{-1}$ s$^{-1}$, more than $5\times10^5$ M$^{-1}$ s$^{-1}$, more than $1\times10^6$ M$^{-1}$ s$^{-1}$, more than $5\times10^6$ M$^{-1}$ s$^{-1}$, more than $1\times10^7$ M$^{-1}$ s$^{-1}$, more than $5\times10^7$ M$^{-1}$ s$^{-1}$ or more than $1\times10^8$ M$^{-1}$ s$^{-1}$. In other aspects, the binding affinity of an EphA4 antagonist, like an APY cyclic peptide disclosed herein, may have an association rate constant for an EpHA4 receptor of between $1\times10^5$ M$^{-1}$ s$^{-1}$ to $1\times10^8$ M$^{-1}$ s$^{-1}$, $1\times10^6$ M$^{-1}$ s$^{-1}$ to $1\times10^8$ M$^{-1}$ s$^{-1}$, $1\times10^5$ M$^{-1}$ s$^{-1}$ to $1\times10^7$ M$^{-1}$ s$^{-1}$ or $1\times10^6$ M$^{-1}$ s$^{-1}$ to $1\times10^7$ M$^{-1}$ s$^{-1}$.

In another embodiment, the binding affinity of an EphA4 antagonist, like an APY cyclic peptide disclosed herein, may have an association rate constant for an ephrin receptor other than an EpHA4 receptor of, e.g., less than $1\times10^0$ M$^{-1}$ s$^{-1}$, $5\times10^0$ M$^{-1}$ s$^{-1}$, less than $1\times10^1$ M$^{-1}$ s$^{-1}$, less than $5\times10^1$ M$^{-1}$ s$^{-1}$, less than $1\times10^2$ M$^{-1}$ s$^{-1}$, less than $5\times10^2$ M$^{-1}$ s$^{-1}$, less than $1\times10^3$ M$^{-1}$ s$^{-1}$, less than $5\times10^3$ M$^{-1}$ s$^{-1}$ or less than $1\times10^4$ M$^{-1}$ s$^{-1}$. In another embodiment, the binding affinity of an EphA4 antagonist, like an APY cyclic peptide disclosed herein, may have an association rate constant for an ephrin receptor other than an EpHA4 receptor of, e.g., at most $1\times10^0$ M$^{-1}$ s$^{-1}$, at most $5\times10^0$ M$^{-1}$ s$^{-1}$, at most $1\times10^1$ M$^{-1}$ s$^{-1}$, at most $5\times10^1$ M$^{-1}$ s$^{-1}$, at most $1\times10^2$ M$^{-1}$ s$^{-1}$, at most $5\times10^2$ M$^{-1}$ s$^{-1}$, at most $1\times10^3$ M$^{-1}$ s$^{-1}$, at most $5\times10^3$ M$^{-1}$ s$^{-1}$ or at most $1\times10^4$ M$^{-1}$ s$^{-1}$.

In another embodiment, the binding affinity of an EphA4 antagonist, like an APY cyclic peptide disclosed herein, may have a disassociation rate constant for an EpHA4 receptor of, e.g., less than $1\times10^{-3}$ s$^{-1}$, $5\times10^{-3}$ s$^{-1}$, less than $1\times10^{-4}$ s$^{-1}$, less than $5\times10^{-4}$ s$^{-1}$ or less than $1\times10^{-5}$ s$^{-1}$. In other aspects of this embodiment, the binding affinity of an α-HIV antibody disclosed herein may have a disassociation rate constant for an EpHA4 receptor of, e.g., less than $1.0\times10^{-4}$ s$^{-1}$, less than $2.0\times10^{-4}$ s$^{-1}$, less than $3.0\times10^{-4}$ s$^{-1}$, less than $4.0\times10^{-4}$ s$^{-1}$, less than $5.0\times10^{-4}$ s$^{-1}$, less than $6.0\times10^{-4}$ s$^{-1}$, less than $7.0\times10^{-4}$ s$^{-1}$, less than $8.0\times10^{-4}$ s$^{-1}$ or less than $9.0\times10^{-4}$ s$^{-1}$. In another embodiment, the binding affinity an EphA4 antagonist, like an APY cyclic peptide disclosed herein, may have a disassociation rate constant for an EpHA4 receptor of, e.g., more than $1\times10^{-3}$ s$^{-1}$, more than $5\times10^{-3}$ s$^{-1}$, more than $1\times10^{-4}$ s$^{-1}$, more than $5\times10^{-4}$ s$^{-1}$ or more than $1\times10^{-5}$ s$^{-1}$. In other aspects of this embodiment, the binding affinity of an EphA4 antagonist, like an APY cyclic peptide disclosed herein, may have a disassociation rate constant for an EpHA4 receptor of, e.g., more than $1.0\times10^{-4}$ s$^{-1}$, more than $2.0\times10^{-4}$ s$^{-1}$, more than $3.0\times10^{-4}$ s$^{-1}$, more than $4.0\times10^{-4}$ s$^{-1}$, more than $5.0\times10^{-4}$ s$^{-1}$, more than $6.0\times10^{-4}$ s$^{-1}$, more than $7.0\times10^{-4}$ s$^{-1}$, more than $8.0\times10^{-4}$ s$^{-1}$ or more than $9.0\times10^{-4}$ s$^{-1}$. In other aspects, the binding affinity of an EphA4 antagonist, like an APY cyclic peptide disclosed herein, may have a disassociation rate constant for an EpHA4 receptor of between $1\times10^{-3}$ s$^{-1}$ to $1\times10^{-5}$ s$^{-1}$, $1\times10^{-3}$ s$^{-1}$ to $1\times10^{-4}$ s$^{-1}$ or $1\times10^{-4}$ s$^{-1}$ to $1\times10^{-5}$ s$^{-1}$.

In another embodiment, the binding affinity of a modified EphA4 antagonist, like an APY cyclic peptide disclosed herein, may have an equilibrium disassociation constant for an EpHA4 receptor of less than 500 nM. In an aspect of this embodiment, the binding affinity of a modified EphA4 antagonist, like an APY cyclic peptide disclosed herein, may have an equilibrium disassociation constant for an EpHA4 receptor of, e.g., less than 500 nM, less than 450 nM, less than 400 nM, less than 350 nM, less than 300 nM, less than 250 nM, less than 200 nM, less than 150 nM, less than 100 nM, less than 75 nM, less than 50 nM, less than 25 nM, less than 20 nM, less than 15 nM, less than 10 nM, less than 5 nM, less than 1 nM, less than 0.5 nM, or less than 0.1 nM. In an aspect of this embodiment, the binding affinity of a modified EphA4 antagonist, like an APY cyclic peptide disclosed herein, may have an equilibrium disassociation constant for an EphA4 receptor of, e.g., about 0.1 nM to about 10 nM, about 0.1 nM to about 25 nM, about 0.1 nM to about 75 nM, about 0.1 nM to about 100 nM, about 0.1 nM to about 125 nM, about 0.1 nM to about 150 nM, about 0.5 nM to about 10 nM, about 0.5 nM to about 25 nM, about 0.5 nM to about 75 nM, about 0.5 nM to about 100 nM, about 0.5 nM to about 125 nM, about 0.5 nM to about 150 nM, about 1 nM to about 10 nM, about 1 nM to about 25 nM, about 1 nM to about 75 nM, about 1 nM to about 100 nM, about 1 nM to about 125 nM, about 1 nM to about 150 nM, about 5 nM to about 10 nM, about 5 nM to about 25 nM, about 5 nM to about 75 nM, about 5 nM to about 100 nM, about 5 nM to about 125 nM, about 5 nM to about 150 nM, about 10 nM to about 25 nM, about 10 nM to about 50 nM, about 10 nM to about 75 nM, about 10 nM to about 100 nM, about 10 nM to about 125 nM, about 10 nM to about 150 nM, about 10 nM to about 175 nM or about 10 nM to about 200 nM.

Binding specificity is the ability of an EphA4 antagonist, like an APY cyclic peptide disclosed herein, to discriminate between a molecule containing the ephrin-binding pocket in the EphA4 ligand binding domain and a molecule that does not contain this ephrin-binding pocket. One way to measure binding specificity is to compare the Kon association rate of an EphA4 antagonist for a molecule containing the ephrin-binding pocket in the EphA4 ligand binding domain relative to the Kon association rate of the EphA4 antagonist for a molecule that does not contain this ephrin-binding pocket. For example, comparing the association rate constant (Ka) of an EphA4 antagonist, like an APY cyclic peptide disclosed herein, that selectively binds to the ephrin-binding pocket in the EphA4 ligand binding domain relative to an ephrin-binding pocket to an Eph receptor other than EphA4. In aspects of this embodiment, an EphA4 antagonist, like an APY cyclic peptide disclosed herein, may have an association rate constant (Ka) for an ephrin-binding pocket to an ephrin receptor other than an EphA4 receptor of, e.g., less than $1\times10^0$ $M^{-1}$ $s^{-1}$, less than $1\times10^1$ $M^{-1}$ $s^{-1}$, less than $1\times10^2$ $M^{-1}$ $s^{-1}$, less than $1\times10^3$ $M^{-1}$ $s^{-1}$ or less than $1\times10^4$ $M^{-1}$ $s^{-1}$. In other aspects of this embodiment, an EphA4 antagonist, like an APY cyclic peptide disclosed herein, have an association rate constant (Ka) for an ephrin-binding pocket to an ephrin receptor other than an EphA4 receptor of, e.g., at most $1\times10^0$ $M^{-1}$ $s^{-1}$, at most $1\times10^1$ $M^{-1}$ $s^{-1}$, at most $1\times10^2$ $M^{-1}$ $s^{-1}$, at most $1\times10^3$ $M^{-1}$ $s^{-1}$ or at most $1\times10^4$ $M^{-1}$ $s^{-1}$.

In other aspects of this embodiment, an EphA4 antagonist, like an APY cyclic peptide disclosed herein, may have an association rate constant (Ka) for the ephrin-binding pocket in the EphA4 ligand binding domain relative to an ephrin-binding pocket of an ephrin receptor other than an EphA4 receptor of, e.g., at least 2-fold more, at least 3-fold more, at least 4-fold more, at least 5-fold more, at least 6-fold more, at least 7-fold more, at least 8-fold more, or at least 9-fold more. In yet other aspects of this embodiment, an EphA4 antagonist, like an APY cyclic peptide disclosed herein, may have an association rate constant (Ka) for the ephrin-binding pocket in the EphA4 ligand binding domain relative to an ephrin-binding pocket of an ephrin receptor other than an EphA4 receptor of, e.g., at least 10-fold more, at least 20-fold more, at least 30-fold more, at least 40-fold more, at least 50-fold more, at least 60-fold more, at least 70-fold more, at least 80-fold more, at least 90-fold more, at least 100-fold more, at least 200-fold more, at least 300-fold more, at least 400-fold more, at least 500-fold more, at least 600-fold more, at least 700-fold more, at least 800-fold more, at least 900-fold more, at least 1,000-fold more, at least 1,200-fold more, at least 1,400-fold more, at least 1,600-fold more, at least 1,800-fold more, at least 2,000-fold more, at least 2,500-fold more, at least 5,000-fold more, at least 7,500-fold more or at least 10,000-fold more. In aspects of this embodiment, an ephrin-binding pocket of an ephrin receptor other than an EphA4 receptor includes an EphA2 receptor, an EphA3 receptor, an EphA5 receptor, an EphA6 receptor, an EphA7 receptor, an EphA8 receptor, an EphB1 receptor, an EphB2 receptor, an EphB3 receptor, an EphB4 receptor, an EphB6 receptor, or any combination thereof.

In other aspects of this embodiment, an EphA4 antagonist, like an APY cyclic peptide disclosed herein, may have an association rate constant (Ka) for the ephrin-binding pocket in the EphA4 ligand binding domain relative to an ephrin-binding pocket of an ephrin receptor other than an EphA4 receptor of, e.g., at most 1-fold more, at most 2-fold more, at most 3-fold more, at most 4-fold more, at most 5-fold more, at most 6-fold more, at most 7-fold more, at most 8-fold more, or at most 9-fold more. In yet other aspects of this embodiment, an EphA4 antagonist, like an APY cyclic peptide disclosed herein, may have an association rate constant (Ka) for the ephrin-binding pocket in the EphA4 ligand binding domain relative to an ephrin-binding pocket of an ephrin receptor other than an EphA4 receptor of, e.g., at most 10-fold more, at most 20-fold more, at most 30-fold more, at most 40-fold more, at most 50-fold more, at most 60-fold more, at most 70-fold more, at most 80-fold more, at most 90-fold more, at most 100-fold more, at most 200-fold more, at most 300-fold more, at most 400-fold more, at most 500-fold more, at most 600-fold more, at most 700-fold more, at most 800-fold more, at most 900-fold more, at most 1,000-fold more, at most 1,200-fold more, at most 1,400-fold more, at most 1,600-fold more, at most 1,800-fold more, at most 2,000-fold more, at most 2,500-fold more, at most 5,000-fold more, at most 7,500-fold more or at most 10,000-fold more. In aspects of this embodiment, an ephrin-binding pocket of an ephrin receptor other than an EphA4 receptor includes an EphA2 receptor, an EphA3 receptor, an EphA5 receptor, an EphA6 receptor, an EphA7 receptor, an EphA8 receptor, an EphB1 receptor, an EphB2 receptor, an EphB3 receptor, an EphB4 receptor, an EphB6 receptor, or any combination thereof.

The binding specificity of an EphA4 antagonist, like an APY cyclic peptide disclosed herein, may also be characterized as a ratio that such an EphA4 antagonist can discriminate the ephrin-binding pocket in the EphA4 ligand binding domain relative to an ephrin-binding pocket of an ephrin receptor other than an EphA4 receptor. In aspects of this embodiment, an EphA4 antagonist, like an APY cyclic peptide disclosed herein, may have a binding specificity ratio for the ephrin-binding pocket in the EphA4 ligand binding domain relative to an ephrin-binding pocket of an ephrin receptor other than an EphA4 receptor of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1. In aspects of this embodiment, an ephrin-binding pocket of an ephrin receptor other than an EphA4 receptor includes an EphA2 receptor, an EphA3 receptor, an EphA5 receptor, an EphA6 receptor, an EphA7 receptor, an EphA8 receptor, an EphB1 receptor, an EphB2 receptor, an EphB3 receptor, an EphB4 receptor, an EphB6 receptor, or any combination thereof.

Aspects of the present specification disclose, in part, an EphA4 antagonist, like an APY cyclic peptide disclosed herein, that exhibits physiological stability. Physiological stability includes properties such as, e.g., biological half-life and plasma half-life. A biological half-life is the time required for one half of the total amount of a particular substance in a biological system to be degraded or eliminated by biological processes such as, e.g., through the kidney, liver and excretion functions when the rate of removal is nearly exponential. Typically, a biological half-life is measured by assaying a pharmacologic and/or physiologic property of the substance. A plasma half-life is the time required for one half of the total concentration of a particular substance in a biological system to reach its steady-state value in blood plasma. The relationship between the biological and plasma half-lives of a substance can be complex, due to factors including accumulation in tissues, active metabolites, and receptor interactions.

In an embodiment, an EphA4 antagonist, like an APY cyclic peptide disclosed herein, may exhibit a therapeutically effective biological half-life. In aspects of this embodiment, an EphA4 antagonist, like an APY cyclic peptide disclosed herein, may exhibit a biological half-life of, e.g., about 12 hours, about 18 hours, about 24 hours, about 30 hours, about 36 hours, about 42 hours, about 48 hours, about 54 hours, about 60 hours, about 66 hours, about 72 hours, about 78 hours, about 84 hours, about 90 hours or about 96 hours. In other aspects of this embodiment, an EphA4 antagonist, like an APY cyclic peptide disclosed herein, may exhibit a biological half-life of, e.g., at least 12 hours, at least 18 hours, at least 24 hours, at least 30 hours, at least 36 hours, at least 42 hours, at least 48 hours, at least 54 hours, at least 60 hours, at least 66 hours, at least 72 hours, at least 78 hours, at least 84 hours, at least 90 hours or at least 96 hours. In yet other aspects of this embodiment, an EphA4 antagonist, like an APY cyclic peptide disclosed herein, may exhibit a biological half-life of, e.g., at most 12 hours, at most 18 hours, at most 24 hours, at most 30 hours, at most 36 hours, at most 42 hours, at most 48 hours, at most 54 hours, at most 60 hours, at most 66 hours, at most 72 hours, at most 78 hours, at most 84 hours, at most 90 hours or at most 96 hours. In still other aspects of this embodiment, an EphA4 antagonist, like an APY cyclic peptide disclosed herein, may exhibit a biological half-life of, e.g., about 12 hours to about 24 hours, about 12 hours to about 36 hours, about 12 hours to about 48 hours, about 12 hours to about 60 hours, about 12 hours to about 72 hours, about 12 hours to about 84 hours, about 12 hours to about 96 hours, about 24 hours to about 36 hours, about 24 hours to about 48 hours, about 24 hours to about 60 hours, about 24 hours to about 72 hours, about 24 hours to about 84 hours, about 24 hours to about 96 hours, about 36 hours to about 48 hours, about 36 hours to about 60 hours, about 36 hours to about 72 hours, about 36 hours to about 84 hours, about 36 hours to about 96 hours, about 48 hours to about 60 hours, about 48 hours to about 72 hours, about 48 hours to about 84 hours, about 48 hours to about 96 hours, about 60 hours to about 72 hours, about 60 hours to about 84 hours, about 60 hours to about 96 hours, about 72 hours to about 84 hours, about 72 hours to about 96 hours or about 84 hours to about 96 hours.

In another embodiment, an EphA4 antagonist, like an APY cyclic peptide disclosed herein, may exhibit a therapeutically effective plasma half-life. In aspects of this embodiment, an EphA4 antagonist, like an APY cyclic peptide disclosed herein, may exhibit a plasma half-life of, e.g., about 12 hours, about 18 hours, about 24 hours, about 30 hours, about 36 hours, about 42 hours, about 48 hours, about 54 hours, about 60 hours, about 66 hours, about 72 hours, about 78 hours, about 84 hours, about 90 hours or about 96 hours. In other aspects of this embodiment, an EphA4 antagonist, like an APY cyclic peptide disclosed herein, may exhibit a plasma half-life of, e.g., at least 12 hours, at least 18 hours, at least 24 hours, at least 30 hours, at least 36 hours, at least 42 hours, at least 48 hours, at least 54 hours, at least 60 hours, at least 66 hours, at least 72 hours, at least 78 hours, at least 84 hours, at least 90 hours or at least 96 hours. In yet other aspects of this embodiment, an EphA4 antagonist, like an APY cyclic peptide disclosed herein, may exhibit a plasma half-life of, e.g., at most 12 hours, at most 18 hours, at most 24 hours, at most 30 hours, at most 36 hours, at most 42 hours, at most 48 hours, at most 54 hours, at most 60 hours, at most 66 hours, at most 72 hours, at most 78 hours, at most 84 hours, at most 90 hours or at most 96 hours. In still other aspects of this embodiment, an EphA4 antagonist, like an APY cyclic peptide disclosed herein, may exhibit a plasma half-life of, e.g., about 12 hours to about 24 hours, about 12 hours to about 36 hours, about 12 hours to about 48 hours, about 12 hours to about 60 hours, about 12 hours to about 72 hours, about 12 hours to about 84 hours, about 12 hours to about 96 hours, about 24 hours to about 36 hours, about 24 hours to about 48 hours, about 24 hours to about 60 hours, about 24 hours to about 72 hours, about 24 hours to about 84 hours, about 24 hours to about 96 hours, about 36 hours to about 48 hours, about 36 hours to about 60 hours, about 36 hours to about 72 hours, about 36 hours to about 84 hours, about 36 hours to about 96 hours, about 48 hours to about 60 hours, about 48 hours to about 72 hours, about 48 hours to about 84 hours, about 48 hours to about 96 hours, about 60 hours to about 72 hours, about 60 hours to about 84 hours, about 60 hours to about 96 hours, about 72 hours to about 84 hours, about 72 hours to about 96 hours or about 84 hours to about 96 hours.

Aspects of the present specification disclose, in part, a pharmaceutical composition. As used herein, the term "pharmaceutical composition" is synonymous with "therapeutic composition" or "pharmaceutically acceptable therapeutic composition" and refers to a composition comprising a therapeutically effective concentration of an active ingredient, such as, e.g., an EphA4 antagonist, like an APY cyclic peptide disclosed herein. A pharmaceutical composition disclosed herein may comprise a single EphA4 antagonist, like an APY cyclic peptide disclosed herein. Alternatively, a pharmaceutical composition disclosed herein may comprise a plurality of EphA4 antagonists, like the APY cyclic peptides disclosed herein. In aspects of this embodiment, pharmaceutical composition disclosed herein may comprise about one, about two, about three, about four, or about five EphA4 antagonists, like the APY cyclic peptides disclosed herein. In other aspects of this embodiment, pharmaceutical composition disclosed herein may comprise one or more, two or more, three or more, four or more or five or more EphA4 antagonists, like the APY cyclic peptides disclosed herein. In yet other aspects of this embodiment, pharmaceutical composition disclosed herein may comprise at most one, at most two, at most three, at most four, or at most five EphA4 antagonists, like the APY cyclic peptides disclosed herein. In still other aspects of this embodiment, pharmaceutical composition disclosed herein may comprise about one to about two, about one to about three, about one to about four, about one to about five, about two to about three, about two to about four, about two to about five, about three to about four, about three to about five or about four to about five, EphA4 antagonists, like the APY cyclic peptides disclosed herein.

The amount of EphA4 antagonist, like an APY cyclic peptide disclosed herein, included in a pharmaceutical composition is an amount sufficient to elicit an appropriate therapeutic response in the individual. Typically, this amount is also one that does not cause significant adverse side effects. Such amount will vary depending on which specific EphA4 antagonist(s), like an APY cyclic peptide disclosed herein, are employed. An optimal amount for a particular pharmaceutical composition can be ascertained by standard studies involving observation of antibody titers and other responses in individuals.

Generally, an effective and safe amount of EphA4 antagonist, like an APY cyclic peptide disclosed herein, included in a pharmaceutical composition varies from about 1 ng to 1,000 µg. In aspects of this embodiment, an amount of an EphA4 antagonist, like an APY cyclic peptide disclosed herein, included in a therapeutic composition may be, e.g., about 1 ng, about 2 ng, about 3 ng, about 4 ng, about 5 ng, about 6 ng, about 7 ng, about 8 ng, about 9 ng, about 10 ng, about 15 ng, about 20 ng, about 25 ng, about 30 ng, about 35 ng, about 40 ng, about 45 ng, about 50 ng, about 55 ng, about 60 ng, about 65 ng, about 70 ng, about 75 ng, about 80 ng, about 85 ng, about 90 ng, about 95 ng, about 100 ng, about 110 ng, about 120 ng, about 130 ng, about 140 ng, about 150 ng, about 160 ng, about 170 ng, about 180 ng, about 190 ng, about 200 ng, about 210 ng, about 220 ng, about 230 ng, about 240 ng, about 250 ng, 260 ng, about 270 ng, about 280 ng, about 290 ng, about 300 ng, about 310 ng, about 320 ng, about 330 ng, about 340 ng, about 350 ng, 360 ng, about 370 ng, about 380 ng, about 390 ng, about 400 ng, about 410 ng, about 420 ng, about 430 ng, about 440 ng, about 450 ng, 460 ng, about 470 ng, about 480 ng, about 490 ng, about 500 ng, about 510 ng, about 520 ng, about 530 ng, about 540 ng, about 550 ng, 560 ng, about 570 ng, about 580 ng, about 590 ng, about 600 ng, about 610 ng, about 620 ng, about 630 ng, about 640 ng, about 650 ng, 660 ng, about 670 ng, about 680 ng, about 690 ng, about 700 ng, about 710 ng, about 720 ng, about 730 ng, about 740 ng, about 750 ng, 760 ng, about 770 ng, about 780 ng, about 790 ng, about 800 ng, about 810 ng, about 820 ng, about 830 ng, about 840 ng, about 850 ng, 860 ng, about 870 ng, about 880 ng, about 890 ng, about 900 ng, about 910 ng, about 920 ng, about 930 ng, about 940 ng, about 950 ng, 960 ng, about 970 ng, about 980 ng, about 990 ng, or about 1,000 ng.

In other aspects of this embodiment, an amount of an EphA4 antagonist, like an APY cyclic peptide disclosed herein, included in a pharmaceutical composition may be, e.g., at least 1 ng, at least 2 ng, at least 3 ng, at least 4 ng, at least 5 ng, at least 6 ng, at least 7 ng, at least 8 ng, at least 9 ng, at least 10 ng, at least 15 ng, at least 20 ng, at least 25 ng, at least 30 ng, at least 35 ng, at least 40 ng, at least 45 ng, at least 50 ng, at least 55 ng, at least 60 ng, at least 65 ng, at least 70 ng, at least 75 ng, at least 80 ng, at least 85 ng, at least 90 ng, at least 95 ng, at least 100 ng, at least 110 ng, at least 120 ng, at least 130 ng, at least 140 ng, at least 150 ng, at least 160 ng, at least 170 ng, at least 180 ng, at least 190 ng, at least 200 ng, at least 210 ng, at least 220 ng, at least 230 ng, at least 240 ng, at least 250 ng, 260 ng, at least 270 ng, at least 280 ng, at least 290 ng, at least 300 ng, at least 310 ng, at least 320 ng, at least 330 ng, at least 340 ng, at least 350 ng, 360 ng, at least 370 ng, at least 380 ng, at least 390 ng, at least 400 ng, at least 410 ng, at least 420 ng, at least 430 ng, at least 440 ng, at least 450 ng, 460 ng, at least 470 ng, at least 480 ng, at least 490 ng, at least 500 ng, at least 510 ng, at least 520 ng, at least 530 ng, at least 540 ng, at least 550 ng, 560 ng, at least 570 ng, at least 580 ng, at least 590 ng, at least 600 ng, at least 610 ng, at least 620 ng, at least 630 ng, at least 640 ng, at least 650 ng, 660 ng, at least 670 ng, at least 680 ng, at least 690 ng, at least 700 ng, at least 710 ng, at least 720 ng, at least 730 ng, at least 740 ng, at least 750 ng, 760 ng, at least 770 ng, at least 780 ng, at least 790 ng, at least 800 ng, at least 810 ng, at least 820 ng, at least 830 ng, at least 840 ng, at least 850 ng, 860 ng, at least 870 ng, at least 880 ng, at least 890 ng, at least 900 ng, at least 910 ng, at least 920 ng, at least 930 ng, at least 940 ng, at least 950 ng, 960 ng, at least 970 ng, at least 980 ng, at least 990 ng, or at least 1,000 ng.

In yet other aspects of this embodiment, an amount of an EphA4 antagonist, like an APY cyclic peptide disclosed herein, included in a pharmaceutical composition may be, e.g., at most 1 ng, at most 2 ng, at most 3 ng, at most 4 ng, at most 5 ng, at most 6 ng, at most 7 ng, at most 8 ng, at most 9 ng, at most 10 ng, at most 15 ng, at most 20 ng, at most 25 ng, at most 30 ng, at most 35 ng, at most 40 ng, at most 45 ng, at most 50 ng, at most 55 ng, at most 60 ng, at most 65 ng, at most 70 ng, at most 75 ng, at most 80 ng, at most 85 ng, at most 90 ng, at most 95 ng, at most 100 ng, at most 110 ng, at most 120 ng, at most 130 ng, at most 140 ng, at most 150 ng, at most 160 ng, at most 170 ng, at most 180 ng, at most 190 ng, at most 200 ng, at most 210 ng, at most 220 ng, at most 230 ng, at most 240 ng, at most 250 ng, 260 ng, at most 270 ng, at most 280 ng, at most 290 ng, at most 300 ng, at most 310 ng, at most 320 ng, at most 330 ng, at most 340 ng, at most 350 ng, 360 ng, at most 370 ng, at most 380 ng, at most 390 ng, at most 400 ng, at most 410 ng, at most 420 ng, at most 430 ng, at most 440 ng, at most 450 ng, 460 ng, at most 470 ng, at most 480 ng, at most 490 ng, at most 500 ng, at most 510 ng, at most 520 ng, at most 530 ng, at most 540 ng, at most 550 ng, 560 ng, at most 570 ng, at most 580 ng, at most 590 ng, at most 600 ng, at most 610 ng, at most 620 ng, at most 630 ng, at most 640 ng, at most 650 ng, 660 ng, at most 670 ng, at most 680 ng, at most 690 ng, at most 700 ng, at most 710 ng, at most 720 ng, at most 730 ng, at most 740 ng, at most 750 ng, 760 ng, at most 770 ng, at most 780 ng, at most 790 ng, at most 800 ng, at most 810 ng, at most 820 ng, at most 830 ng, at most 840 ng, at most 850 ng, 860 ng, at most 870 ng, at most 880 ng, at most 890 ng, at most 900 ng, at most 910 ng, at most 920 ng, at most 930 ng, at most 940 ng, at most 950 ng, 960 ng, at most 970 ng, at most 980 ng, at most 990 ng, or at most 1,000 ng.

In still other aspects of this embodiment, an amount of an EphA4 antagonist, like an APY cyclic peptide disclosed herein, included in a pharmaceutical composition may be in the range of, e.g., about 1 ng to about 10 ng, about 1 ng to about 20 ng, about 1 ng to about 30 ng, about 1 ng to about 40 ng, about 1 ng to about 50 ng, about 1 ng to about 60 ng, about 1 ng to about 70 ng, about 1 ng to about 80 ng, about 1 ng to about 90 ng, about 1 ng to about 100 ng, about 1 ng to about 110 ng, about 1 ng to about 120 ng, about 1 ng to about 130 ng, about 1 ng to about 140 ng, about 1 ng to about 150 ng, about 5 ng to about 10 ng, about 5 ng to about 20 ng, about 5 ng to about 30 ng, about 5 ng to about 40 ng, about 5 ng to about 50 ng, about 5 ng to about 60 ng, about 5 ng to about 70 ng, about 5 ng to about 80 ng, about 5 ng to about 90 ng, about 5 ng to about 100 ng, about 5 ng to about 110 ng, about 5 ng to about 120 ng, about 5 ng to about 130 ng, about 5 ng to about 140 ng, about 5 ng to about 150 ng, about 10 ng to about 20 ng, about 10 ng to about 30 ng, about 10 ng to about 40 ng, about 10 ng to about 50 ng, about 10 ng to about 60 ng, about 10 ng to about 70 ng, about 10 ng to about 80 ng, about 10 ng to about 90 ng, about 10 ng to about 100 ng, about 10 ng to about 110 ng, about 10 ng to about 120 ng, about 10 ng to about 130 ng, about 10 ng to about 140 ng, about 10 ng to about 150 ng, about 10 ng to about 175 ng, about 10 ng to about 200 ng, about 10 ng to about 225 ng, about 10 ng to about 250 ng, about 25 ng to about 50 ng, about 25 ng to about 75 ng, about 25 ng to about 100 ng, about 25 ng to about 125 ng, about 25 ng to about 150 ng, about 25 ng to about 175 ng, about 25 ng to about 200 ng, about 25 ng to about 225 ng, about 25 ng to about 250 ng, about 50 ng to about 75 ng, about 50 ng to about 100 ng, about 50 ng to about 125 ng, about 50 ng to about 150 ng, about 50 ng to about 175 ng, about 50 ng to about 200 ng, about 50 ng to about 225 ng, about 50 ng to about 250 ng, about 75 ng to about 100 ng, about 75 ng to about 125 ng, about 75 ng to about 150 ng, about 75 ng to about 175 ng, about 75 ng to about 200 ng, about 75 ng to about 225 ng, or about 75 ng to about 250 ng.

In still other aspects of this embodiment, an amount of an EphA4 antagonist, like an APY cyclic peptide disclosed herein, included in a pharmaceutical composition may be in the range of, e.g., about 100 ng to about 125 ng, about 100 ng to about 150 ng, about 100 ng to about 175 ng, about 100 ng to about 200 ng, about 100 ng to about 225 ng, about 100 ng to about 250 ng, about 100 ng to about 275 ng, about 100 ng to about 300 ng, about 100 ng to about 325 ng, about 100 ng to about 350 ng, about 100 ng to about 375 ng, about 100 ng to about 400 ng, about 100 ng to about 425 ng, about 100 ng to about 450 ng, about 100 ng to about 475 ng, about 100 ng to about 500 ng, about 100 ng to about 525 ng, about 100 ng to about 550 ng, about 100 ng to about 575 ng, about 100 ng to about 600 ng, about 125 ng to about 150 ng, about 125 ng to about 175 ng, about 125 ng to about 200 ng, about 125 ng to about 225 ng, about 125 ng to about 250 ng, about 125 ng to about 275 ng, about 125 ng to about 300 ng, about 125 ng to about 325 ng, about 125 ng to about 350 ng, about 125 ng to about 375 ng, about 125 ng to about 400 ng, about 125 ng to about 425 ng, about 125 ng to about 450 ng, about 125 ng to about 475 ng, about 125 ng to about 500 ng, about 125 ng to about 525 ng, about 125 ng to about 550 ng, about 125 ng to about 575 ng, about 125 ng to about 600 ng, about 150 ng to about 175 ng, about 150 ng to about 200 ng, about 150 ng to about 225 ng, about 150 ng to about 250 ng, about 150 ng to about 275 ng, about 150 ng to about 300 ng, about 150 ng to about 325 ng, about 150 ng to about 350 ng, about 150 ng to about 375 ng, about 150 ng to about 400 ng, about 150 ng to about 425 ng, about 150 ng to about 450 ng, about 150 ng to about 475 ng, about 150 ng to about 500 ng, about 150 ng to about 525 ng, about 150 ng to about 550 ng, about 150 ng to about 575 ng, about 150 ng to about 600 ng, about 200 ng to about 225 ng, about 200 ng to about 250 ng, about 200 ng to about 275 ng, about 200 ng to about 300 ng, about 200 ng to about 325 ng, about 200 ng to about 350 ng, about 200 ng to about 375 ng, about 200 ng to about 400 ng, about 200 ng to about 425 ng, about 200 ng to about 450 ng, about 200 ng to about 475 ng, about 200 ng to about 500 ng, about 200 ng to about 525 ng, about 200 ng to about 550 ng, about 200 ng to about 575 ng, about 200 ng to about 600 ng, about 200 ng to about 625 ng, about 200 ng to about 650 ng, about 200 ng to about 675 ng, about 200 ng to about 700 ng, about 200 ng to about 725 ng, about 200 ng to about 750 ng, about 200 ng to about 775 ng, about 200 ng to about 800 ng, about 200 ng to about 825 ng, about 200 ng to about 850 ng, about 200 ng to about 875 ng, about 200 ng to about 900 ng, about 200 ng to about 925 ng, about 200 ng to about 950 ng, about 200 ng to about 975 ng, or about 200 ng to about 1,000 ng.

In still other aspects of this embodiment, an amount of an EphA4 antagonist, like an APY cyclic peptide disclosed herein, included in a pharmaceutical composition may be in the range of, e.g., about 250 ng to about 275 ng, about 250 ng to about 300 ng, about 250 ng to about 325 ng, about 250 ng to about 350 ng, about 250 ng to about 375 ng, about 250 ng to about 400 ng, about 250 ng to about 425 ng, about 250 ng to about 450 ng, about 250 ng to about 475 ng, about 250 ng to about 500 ng, about 250 ng to about 525 ng, about 250 ng to about 550 ng, about 250 ng to about 575 ng, about 250 ng to about 600 ng, about 250 ng to about 625 ng, about 250 ng to about 650 ng, about 250 ng to about 675 ng, about 250 ng to about 700 ng, about 250 ng to about 725 ng, about 250 ng to about 750 ng, about 250 ng to about 775 ng, about 250 ng to about 800 ng, about 250 ng to about 825 ng, about 250 ng to about 850 ng, about 250 ng to about 875 ng, about 250 ng to about 900 ng, about 250 ng to about 925 ng, about 250 ng to about 950 ng, about 250 ng to about 975 ng, about 250 ng to about 1,000 ng, about 300 ng to about 325 ng, about 300 ng to about 350 ng, about 300 ng to about 375 ng, about 300 ng to about 400 ng, about 300 ng to about 425 ng, about 300 ng to about 450 ng, about 300 ng to about 475 ng, about 300 ng to about 500 ng, about 300 ng to about 525 ng, about 300 ng to about 550 ng, about 300 ng to about 575 ng, about 300 ng to about 600 ng, about 300 ng to about 625 ng, about 300 ng to about 650 ng, about 300 ng to about 675 ng, about 300 ng to about 700 ng, about 300 ng to about 725 ng, about 300 ng to about 750 ng, about 300 ng to about 775 ng, about 300 ng to about 800 ng, about 300 ng to about 825 ng, about 300 ng to about 850 ng, about 300 ng to about 875 ng, about 300 ng to about 900 ng, about 300 ng to about 925 ng, about 300 ng to about 950 ng, about 300 ng to about 975 ng, about 300 ng to about 1,000 ng, about 400 ng to about 425 ng, about 400 ng to about 450 ng, about 400 ng to about 475 ng, about 400 ng to about 500 ng, about 400 ng to about 525 ng, about 400 ng to about 550 ng, about 400 ng to about 575 ng, about 400 ng to about 600 ng, about 400 ng to about 625 ng, about 400 ng to about 650 ng, about 400 ng to about 675 ng, about 400 ng to about 700 ng, about 400 ng to about 725 ng, about 400 ng to about 750 ng, about 400 ng to about 775 ng, about 400 ng to about 800 ng, about 400 ng to about 825 ng, about 400 ng to about 850 ng, about 400 ng to about 875 ng, about 400 ng to about 900 ng, about 400 ng to about 925 ng, about 400 ng to about 950 ng, about 400 ng to about 975 ng, or about 400 ng to about 1,000 ng.

In still other aspects of this embodiment, an amount of an EphA4 antagonist, like an APY cyclic peptide disclosed herein, included in a pharmaceutical composition may be in the range of, e.g., about 500 ng to about 525 ng, about 500 ng to about 550 ng, about 500 ng to about 575 ng, about 500 ng to about 600 ng, about 500 ng to about 625 ng, about 500 ng to about 650 ng, about 500 ng to about 675 ng, about 500 ng to about 700 ng, about 500 ng to about 725 ng, about 500 ng to about 750 ng, about 500 ng to about 775 ng, about 500 ng to about 800 ng, about 500 ng to about 825 ng, about 500 ng to about 850 ng, about 500 ng to about 875 ng, about 500 ng to about 900 ng, about 500 ng to about 925 ng, about 500 ng to about 950 ng, about 500 ng to about 975 ng, about 500 ng to about 1,000 ng, about 600 ng to about 625 ng, about 600 ng to about 650 ng, about 600 ng to about 675 ng, about 600 ng to about 700 ng, about 600 ng to about 725 ng, about 600 ng to about 750 ng, about 600 ng to about 775 ng, about 600 ng to about 800 ng, about 600 ng to about 825 ng, about 600 ng to about 850 ng, about 600 ng to about 875 ng, about 600 ng to about 900 ng, about 600 ng to about 925 ng, about 600 ng to about 950 ng, about 600 ng to about 975 ng, about 600 ng to about 1,000 ng, about 700 ng to about 725 ng, about 700 ng to about 750 ng, about 700 ng to about 775 ng, about 700 ng to about 800 ng, about 700 ng to about 825 ng, about 700 ng to about 850 ng, about 700 ng to about 875 ng, about 700 ng to about 900 ng, about 700 ng to about 925 ng, about 700 ng to about 950 ng, about 700 ng to about 975 ng, about 700 ng to about 1,000 ng, about 800 ng to about 825 ng, about 800 ng to about 850 ng, about 800 ng to about 875 ng, about 800 ng to about 900 ng, about 800 ng to about 925 ng, about 800 ng to about 950 ng, about 800 ng to about 975 ng, or about 800 ng to about 1,000 ng.

In aspects of this embodiment, an amount of an EphA4 antagonist, like an APY cyclic peptide disclosed herein, included in a pharmaceutical composition may be, e.g., about 1 µg, about 2 µg, about 3 µg, about 4 µg, about 5 µg, about 6 µg, about 7 µg, about 8 µg, about 9 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, 260 µg, about 270 µg, about 280 µg, about 290 µg, about 300 µg, about 310 µg, about 320 µg, about 330 µg, about 340 µg, about 350 µg, 360 µg, about 370 µg, about 380 µg, about 390 µg, about 400 µg, about 410 µg, about 420 µg, about 430 µg, about 440 µg, about 450 µg, 460 µg, about 470 µg, about 480 µg, about 490 µg, about 500 µg, about 510 µg, about 520 µg, about 530 µg, about 540 µg, about 550 µg, 560 µg, about 570 µg, about 580 µg, about 590 µg, about 600 µg, about 610 µg, about 620 µg, about 630 µg, about 640 µg, about 650 µg, 660 µg, about 670 µg, about 680 µg, about 690 µg, about 700 µg, about 710 µg, about 720 µg, about 730 µg, about 740 µg, about 750 µg, 760 µg, about 770 µg, about 780 µg, about 790 µg, about 800 µg, about 810 µg, about 820 µg, about 830 µg, about 840 µg, about 850 µg, 860 µg, about 870 µg, about 880 µg, about 890 µg, about 900 µg, about 910 µg, about 920 µg, about 930 µg, about 940 µg, about 950 µg, 960 µg, about 970 µg, about 980 µg, about 990 µg, or about 1,000 µg.

In other aspects of this embodiment, an amount of an EphA4 antagonist, like an APY cyclic peptide disclosed herein, included in a pharmaceutical composition may be, e.g., at least 1 µg, at least 2 µg, at least 3 µg, at least 4 µg, at least 5 µg, at least 6 µg, at least 7 µg, at least 8 µg, at least 9 µg, at least 10 µg, at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, at least 100 µg, at least 110 µg, at least 120 µg, at least 130 µg, at least 140 µg, at least 150 µg, at least 160 µg, at least 170 µg, at least 180 µg, at least 190 µg, at least 200 µg, at least 210 µg, at least 220 µg, at least 230 µg, at least 240 µg, at least 250 µg, 260 µg, at least 270 µg, at least 280 µg, at least 290 µg, at least 300 µg, at least 310 µg, at least 320 µg, at least 330 µg, at least 340 µg, at least 350 µg, 360 µg, at least 370 µg, at least 380 µg, at least 390 µg, at least 400 µg, at least 410 µg, at least 420 µg, at least 430 µg, at least 440 µg, at least 450 µg, 460 µg, at least 470 µg, at least 480 µg, at least 490 µg, at least 500 µg, at least 510 µg, at least 520 µg, at least 530 µg, at least 540 µg, at least 550 µg, 560 µg, at least 570 µg, at least 580 µg, at least 590 µg, at least 600 µg, at least 610 µg, at least 620 µg, at least 630 µg, at least 640 µg, at least 650 µg, 660 µg, at least 670 µg, at least 680 µg, at least 690 µg, at least 700 µg, at least 710 µg, at least 720 µg, at least 730 µg, at least 740 µg, at least 750 µg, 760 µg, at least 770 µg, at least 780 µg, at least 790 µg, at least 800 µg, at least 810 µg, at least 820 µg, at least 830 µg, at least 840 µg, at least 850 µg, 860 µg, at least 870 µg, at least 880 µg, at least 890 µg, at least 900 µg, at least 910 µg, at least 920 µg, at least 930 µg, at least 940 µg, at least 950 µg, 960 µg, at least 970 µg, at least 980 µg, at least 990 µg, or at least 1,000 µg.

In yet other aspects of this embodiment, an amount of an EphA4 antagonist, like an APY cyclic peptide disclosed herein, included in a pharmaceutical composition may be, e.g., at most 1 µg, at most 2 µg, at most 3 µg, at most 4 µg, at most 5 µg, at most 6 µg, at most 7 µg, at most 8 µg, at most 9 µg, at most 10 µg, at most 15 µg, at most 20 µg, at most 25 µg, at most 30 µg, at most 35 µg, at most 40 µg, at most 45 µg, at most 50 µg, at most 55 µg, at most 60 µg, at most 65 µg, at most 70 µg, at most 75 µg, at most 80 µg, at most 85 µg, at most 90 µg, at most 95 µg, at most 100 µg, at most 110 µg, at most 120 µg, at most 130 µg, at most 140 µg, at most 150 µg, at most 160 µg, at most 170 µg, at most 180 µg, at most 190 µg, at most 200 µg, at most 210 µg, at most 220 µg, at most 230 µg, at most 240 µg, at most 250 µg, 260 µg, at most 270 µg, at most 280 µg, at most 290 µg, at most 300 µg, at most 310 µg, at most 320 µg, at most 330 µg, at most 340 µg, at most 350 µg, 360 µg, at most 370 µg, at most 380 µg, at most 390 µg, at most 400 µg, at most 410 µg, at most 420 µg, at most 430 µg, at most 440 µg, at most 450 µg, 460 µg, at most 470 µg, at most 480 µg, at most 490 µg, at most 500 µg, at most 510 µg, at most 520 µg, at most 530 µg, at most 540 µg, at most 550 µg, 560 µg, at most 570 µg, at most 580 µg, at most 590 µg, at most 600 µg, at most 610 µg, at most 620 µg, at most 630 µg, at most 640 µg, at most 650 µg, 660 µg, at most 670 µg, at most 680 µg, at most 690 µg, at most 700 µg, at most 710 µg, at most 720 µg, at most 730 µg, at most 740 µg, at most 750 µg, 760 µg, at most 770 µg, at most 780 µg, at most 790 µg, at most 800 µg, at most 810 µg, at most 820 µg, at most 830 µg, at most 840 µg, at most 850 µg, 860 µg, at most 870 µg, at most 880 µg, at most 890 µg, at most 900 µg, at most 910 µg, at most 920 µg, at most 930 µg, at most 940 µg, at most 950 µg, 960 µg, at most 970 µg, at most 980 µg, at most 990 µg, or at most 1,000 µg.

In still other aspects of this embodiment, an amount of an EphA4 antagonist, like an APY cyclic peptide disclosed herein, included in a pharmaceutical composition may be in the range of, e.g., about 1 µg to about 10 µg, about 1 µg to about 20 µg, about 1 µg to about 30 µg, about 1 µg to about 40 µg, about 1 µg to about 50 µg, about 1 µg to about 60 µg, about 1 µg to about 70 µg, about 1 µg to about 80 µg, about 1 µg to about 90 µg, about 1 µg to about 100 µg, about 1 µg to about 110 µg, about 1 µg to about 120 µg, about 1 µg to about 130 µg, about 1 µg to about 140 µg, about 1 µg to about 150 µg, about 5 µg to about 10 µg, about 5 µg to about 20 µg, about 5 µg to about 30 µg, about 5 µg to about 40 µg, about 5 µg to about 50 µg, about 5 µg to about 60 µg, about 5 µg to about 70 µg, about 5 µg to about 80 µg, about 5 µg to about 90 µg, about 5 µg to about 100 µg, about 5 µg to about 110 µg, about 5 µg to about 120 µg, about 5 µg to about 130 µg, about 5 µg to about 140 µg, about 5 µg to about 150 µg, about 10 µg to about 20 µg, about 10 µg to about 30 µg, about 10 µg to about 40 µg, about 10 µg to about 50 µg, about 10 µg to about 60 µg, about 10 µg to about 70 µg, about 10 µg to about 80 µg, about 10 µg to about 90 µg, about 10 µg to about 100 µg, about 10 µg to about 110 µg, about 10 µg to about 120 µg, about 10 µg to about 130 µg, about 10 µg to about 140 µg, about 10 µg to about 150 µg, about 10 µg to about 175 µg, about 10 µg to about 200 µg, about 10 µg to about 225 µg, about 10 µg to about 250 µg, about 25 µg to about 50 µg, about 25 µg to about 75 µg, about 25 µg to about 100 µg, about 25 µg to about 125 µg, about 25 µg to about 150 µg, about 25 µg to about 175 µg, about 25 µg to about 200 µg, about 25 µg to about 225 µg, about 25 µg to about 250 µg, about 50 µg to about 75 µg, about 50 µg to about 100 µg, about 50 µg to about 125 µg, about 50 µg to about 150 µg, about 50 µg to about 175 µg, about 50 µg to about 200 µg, about 50 µg to about 225 µg, about 50 µg to about 250 µg, about 75 µg to about 100 µg, about 75 µg to about 125 µg, about 75 µg to about 150 µg, about 75 µg to about 175 µg, about 75 µg to about 200 µg, about 75 µg to about 225 µg, or about 75 µg to about 250 µg.

In still other aspects of this embodiment, an amount of an EphA4 antagonist, like an APY cyclic peptide disclosed herein, included in a pharmaceutical composition may be in the range of, e.g., about 100 µg to about 125 µg, about 100 µg to about 150 µg, about 100 µg to about 175 µg, about 100 µg to about 200 µg, about 100 µg to about 225 µg, about 100 µg to about 250 µg, about 100 µg to about 275 µg, about 100 µg to about 300 µg, about 100 µg to about 325 µg, about 100 µg to about 350 µg, about 100 µg to about 375 µg, about 100 µg to about 400 µg, about 100 µg to about 425 µg, about 100 µg to about 450 µg, about 100 µg to about 475 µg, about 100 µg to about 500 µg, about 100 µg to about 525 µg, about 100 µg to about 550 µg, about 100 µg to about 575 µg, about 100 µg to about 600 µg, about 125 µg to about 150 µg, about 125 µg to about 175 µg, about 125 µg to about 200 µg, about 125 µg to about 225 µg, about 125 µg to about 250 µg, about 125 µg to about 275 µg, about 125 µg to about 300 µg, about 125 µg to about 325 µg, about 125 µg to about 350 µg, about 125 µg to about 375 µg, about 125 µg to about 400 µg, about 125 µg to about 425 µg, about 125 µg to about 450 µg, about 125 µg to about 475 µg, about 125 µg to about 500 µg, about 125 µg to about 525 µg, about 125 µg to about 550 µg, about 125 µg to about 575 µg, about 125 µg to about 600 µg, about 150 µg to about 175 µg, about 150 µg to about 200 µg, about 150 µg to about 225 µg, about 150 µg to about 250 µg, about 150 µg to about 275 µg, about 150 µg to about 300 µg, about 150 µg to about 325 µg, about 150 µg to about 350 µg, about 150 µg to about 375 µg, about 150 µg to about 400 µg, about 150 µg to about 425 µg, about 150 µg to about 450 µg, about 150 µg to about 475 µg, about 150 µg to about 500 µg, about 150 µg to about 525 µg, about 150 µg to about 550 µg, about 150 µg to about 575 µg, about 150 µg to about 600 µg, about 200 µg to about 225 µg, about 200 µg to about 250 µg, about 200 µg to about 275 µg, about 200 µg to about 300 µg, about 200 µg to about 325 µg, about 200 µg to about 350 µg, about 200 µg to about 375 µg, about 200 µg to about 400 µg, about 200 µg to about 425 µg, about 200 µg to about 450 µg, about 200 µg to about 475 µg, about 200 µg to about 500 µg, about 200 µg to about 525 µg, about 200 µg to about 550 µg, about 200 µg to about 575 µg, about 200 µg to about 600 µg, about 200 µg to about 625 µg, about 200 µg to about 650 µg, about 200 µg to about 675 µg, about 200 µg to about 700 µg, about 200 µg to about 725 µg, about 200 µg to about 750 µg, about 200 µg to about 775 µg, about 200 µg to about 800 µg, about 200 µg to about 825 µg, about 200 µg to about 850 µg, about 200 µg to about 875 µg, about 200 µg to about 900 µg, about 200 µg to about 925 µg, about 200 µg to about 950 µg, about 200 µg to about 975 µg, or about 200 µg to about 1,000 µg.

In still other aspects of this embodiment, an amount of an EphA4 antagonist, like an APY cyclic peptide disclosed herein, included in a pharmaceutical composition may be in the range of, e.g., about 250 µg to about 275 µg, about 250 µg to about 300 µg, about 250 µg to about 325 µg, about 250 µg to about 350 µg, about 250 µg to about 375 µg, about 250 µg to about 400 µg, about 250 µg to about 425 µg, about 250 µg to about 450 µg, about 250 µg to about 475 µg, about 250 µg to about 500 µg, about 250 µg to about 525 µg, about 250 µg to about 550 µg, about 250 µg to about 575 µg, about 250 µg to about 600 µg, about 250 µg to about 625 µg, about 250 µg to about 650 µg, about 250 µg to about 675 µg, about 250 µg to about 700 µg, about 250 µg to about 725 µg, about 250 µg to about 750 µg, about 250 µg to about 775 µg, about 250 µg to about 800 µg, about 250 µg to about 825 µg, about 250 µg to about 850 µg, about 250 µg to about 875 µg, about 250 µg to about 900 µg, about 250 µg to about 925 µg, about 250 µg to about 950 µg, about 250 µg to about 975 µg, about 250 µg to about 1,000 µg, about 300 µg to about 325 µg, about 300 µg to about 350 µg, about 300 µg to about 375 µg, about 300 µg to about 400 µg, about 300 µg to about 425 µg, about 300 µg to about 450 µg, about 300 µg to about 475 µg, about 300 µg to about 500 µg, about 300 µg to about 525 µg, about 300 µg to about 550 µg, about 300 µg to about 575 µg, about 300 µg to about 600 µg, about 300 µg to about 625 µg, about 300 µg to about 650 µg, about 300 µg to about 675 µg, about 300 µg to about 700 µg, about 300 µg to about 725 µg, about 300 µg to about 750 µg, about 300 µg to about 775 µg, about 300 µg to about 800 µg, about 300 µg to about 825 µg, about 300 µg to about 850 µg, about 300 µg to about 875 µg, about 300 µg to about 900 µg, about 300 µg to about 925 µg, about 300 µg to about 950 µg, about 300 µg to about 975 µg, about 300 µg to about 1,000 µg, about 400 µg to about 425 µg, about 400 µg to about 450 µg, about 400 µg to about 475 µg, about 400 µg to about 500 µg, about 400 µg to about 525 µg, about 400 µg to about 550 µg, about 400 µg to about 575 µg, about 400 µg to about 600 µg, about 400 µg to about 625 µg, about 400 µg to about 650 µg, about 400 µg to about 675 µg, about 400 µg to about 700 µg, about 400 µg to about 725 µg, about 400 µg to about 750 µg, about 400 µg to about 775 µg, about 400 µg to about 800 µg, about 400 µg to about 825 µg, about 400 µg to about 850 µg, about 400 µg to about 875 µg, about 400 µg to about 900 µg, about 400 µg to about 925 µg, about 400 µg to about 950 µg, about 400 µg to about 975 µg, or about 400 µg to about 1,000 µg.

In still other aspects of this embodiment, an amount of an EphA4 antagonist, like an APY cyclic peptide disclosed herein, included in a pharmaceutical composition may be in the range of, e.g., about 500 µg to about 525 µg, about 500 µg to about 550 µg, about 500 µg to about 575 µg, about 500 µg to about 600 µg, about 500 µg to about 625 µg, about 500 µg to about 650 µg, about 500 µg to about 675 µg, about 500 µg to about 700 µg, about 500 µg to about 725 µg, about 500 µg to about 750 µg, about 500 µg to about 775 µg, about 500 µg to about 800 µg, about 500 µg to about 825 µg, about 500 µg to about 850 µg, about 500 µg to about 875 µg, about 500 µg to about 900 µg, about 500 µg to about 925 µg, about 500 µg to about 950 µg, about 500 µg to about 975 µg, about 500 µg to about 1,000 µg, about 600 µg to about 625 µg, about 600 µg to about 650 µg, about 600 µg to about 675 µg, about 600 µg to about 700 µg, about 600 µg to about 725 µg, about 600 µg to about 750 µg, about 600 µg to about 775 µg, about 600 µg to about 800 µg, about 600 µg to about 825 µg, about 600 µg to about 850 µg, about 600 µg to about 875 µg, about 600 µg to about 900 µg, about 600 µg to about 925 µg, about 600 µg to about 950 µg, about 600 µg to about 975 µg, about 600 µg to about 1,000 µg, about 700 µg to about 725 µg, about 700 µg to about 750 µg, about 700 µg to about 775 µg, about 700 µg to about 800 µg, about 700 µg to about 825 µg, about 700 µg to about 850 µg, about 700 µg to about 875 µg, about 700 µg to about 900 µg, about 700 µg to about 925 µg, about 700 µg to about 950 µg, about 700 µg to about 975 µg, about 700 µg to about 1,000 µg, about 800 µg to about 825 µg, about 800 µg to about 850 µg, about 800 µg to about 875 µg, about 800 µg to about 900 µg, about 800 µg to about 925 µg, about 800 µg to about 950 µg, about 800 µg to about 975 µg, or about 800 µg to about 1,000 µg.

A pharmaceutical composition disclosed herein can optionally include one or more pharmaceutically acceptable carriers that facilitate processing of an active ingredient into therapeutic compositions. As used herein "pharmaceutically acceptable" refers to any molecular entity or composition that does not produce an adverse, allergic or other untoward or unwanted reaction when administered to an individual. As used herein, the term "pharmacologically acceptable carriers" is synonymous with "pharmacological carriers" and means any compound that has substantially no long term or permanent detrimental effect when administered and encompasses terms such as "pharmacologically acceptable vehicle, stabilizer, diluent, additive, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carriers. Any of a variety of pharmaceutically acceptable carrier can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); GOODMAN & GILMAN'S THE PHARMACOLOGICAL BASIS OF THERAPEUTICS (Joel G. Hardman et al., eds., McGraw-Hill Professional, $10^{th}$ ed. 2001); and HANDBOOK OF PHARMACEUTICAL EXCIPIENTS (Raymond C. Rowe et al., APhA Publications, $4^{th}$ edition 2003). These protocols are routine procedures and any modifications are well within the scope of one skilled in the art and from the teaching herein.

A pharmaceutical composition disclosed herein may optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a therapeutic composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. An active ingredient, such as, e.g., an α-HIV antibody disclosed herein, may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a therapeutic composition.

A pharmaceutical composition comprising one or more EphA4 antagonist, like an APY cyclic peptide disclosed herein, is useful for medical and veterinary applications. A pharmaceutical composition may be administered to an individual alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

Aspects of the present specification disclose, in part, a method of treating an EphA4-based disease, disorder or pathology. An EphA4-based disease, disorder or pathology refers to any condition, disease or disorder or pathology where a pathophysiology effect is due to dysregulation of EphA4 signaling in a manner that causes EphA4 signaling hyperactivity in cells or spatially or temporally aberrant EphA4 signaling.

Such methods include therapeutic (following onset of an EphA4-based disease) and prophylactic (prior to onset of an EphA4-based disease). For example, therapeutic and prophylactic methods of treating an individual for an EphA4-based disease, disorder or pathology include treating an individual at risk of having an EphA4-based disease, disorder or pathology, treating an individual having an EphA4-based disease, disorder or pathology, and methods of protecting an individual from an EphA4-based disease, disorder or pathology, to decrease or reduce the probability of an EphA4-based disease, disorder or pathology in an individual, to decrease or reduce susceptibility of an individual to an EphA4-based disease, disorder or pathology, or to inhibit or prevent an EphA4-based disease, disorder or pathology in an individual, and to decrease, reduce, inhibit or suppress transmission of an EphA4-based disease, disorder or pathology from an afflicted individual to an unafflicted individual. Such methods include administering a pharmaceutical composition disclosed herein to therapeutically or prophylactically treat an individual having or at risk of having an EphA4-based disease, disorder or pathology. Accordingly, methods can treat an EphA4-based disease or pathology, or provide the individual with protection from an EphA4-based disease, disorder or pathology (e.g., prophylactic protection).

In an embodiment, a method of treating an EphA4-based disease, disorder or pathology, comprises administering one or more EphA4 antagonists, like one or more APY cyclic peptides disclosed herein, or a pharmaceutical composition disclosed herein to an individual in need thereof in an amount sufficient to reduce one or more physiological conditions or symptom associated with an EphA4-based disease, disorder or pathology, thereby treating the EphA4-based disease, disorder or pathology. In aspects of this embodiment, an EphA4-based disease, disorder or pathology includes, without limitation, a neurodegenerative disease, a hearing loss, promotion of nerve regeneration, promotion of neuroprotection, and a cancer.

Neurodegenerative diseases are conditions that affect brain or peripheral nerve function. They result from the deterioration of neurons and they are characterized by progressive central or peripheral nervous dysfunction. They are divided into two groups: conditions causing problems with movement or sensation and conditions affecting memory or related to dementia. EphA4 signaling activity has important functions in both categories. For example, increased expression of EphA4 and its activation by ephrin ligands contribute to the pathogenesis of ALS, Alzheimer's disease, multiple sclerosis, stroke and traumatic brain injury and other neurodegenerative disease because EphA4 signaling leads to abnormal inhibition of axon growth, aberrant synaptic function and poor neuronal survival. Thus, an EphA4 antagonist, like an APY cyclic peptide disclosed herein, or a pharmaceutical composition disclosed herein can be useful in treating any neurodegenerative disease expressing high EphA4 levels because these APY cyclic peptides inhibit EphA4 signaling. A neurodegenerative disease includes, without limitation, an Alexander disease, an Alper's disease, Alzheimer's disease, an amyotrophic lateral sclerosis, an ataxia telangiectasia, a Canavan disease, a Cockayne syndrome, a corticobasal degeneration, a Creutzfeldt-Jakob disease, a Guillain-Barre Syndrome a HIV-induced neurodegeneration, a Huntington disease, a Kennedy's disease, a Krabbe disease, a Lewy body dementia, a Machado-Joseph disease, a multiple sclerosis, a Parkinson's disease, a Pelizaeus-Merzbacher disease, a Pick's disease, a primary lateral sclerosis, a Refsum's disease, a Sandhoff disease, a Schilder's disease, a spinal cord injury, a Steele-Richardson-Olszewski disease, a stroke, a tabes dorsalis and/or a traumatic brain injury. Symptoms associated with a neurodegenerative disease include, without limitation, abnormal movement, abnormal sensation, limb grasping, muscle weakness, atrophy, paralysis, abnormal inhibition of axon growth, abnormal axonal transport, aberrant synaptic function, synaptic transmission loss, impaired synaptic plasticity, synaptic loss, neuronal degeneration, motor neuron degeneration, motor neuron loss, poor neuronal survival, memory loss, impaired learning, dementia, β-amyloid plaque deposits, aberrant neurofilament accumulation, reactive astroglia and/or reactive microglia.

In another embodiment, a method of treating an EphA4-based disease, disorder or pathology includes a method of treating a neurodegenerative disease. In an aspect of this embodiment, a method of treating a neurodegenerative disease comprises administering one or more EphA4 antagonists, like one or more APY cyclic peptides disclosed herein, or a pharmaceutical composition disclosed herein to an individual in need thereof in an amount sufficient to reduce one or more physiological conditions or symptom associated with a neurodegenerative disease, thereby treating the neurodegenerative disease.

Cochlear hair cells are the primary sensory receptors of both the auditory system and the vestibular system in all vertebrates. Through mechanotransduction, hair cells detect movement in their environment (i.e., sound) and are responsible for the sense of hearing. Hair cell damage results in decreased hearing sensitivity, i.e. sensorineural hearing loss. Such damage can occur due to hereditary and/or environmental causes. For example, hair cell degenerate and/or death can be caused by lack of essential growth factors, exogenous toxins (such as ototoxic drugs), overstimulation by noise or sound, viral or bacterial infections, autoimmune conditions or hereditary disease. Since human cochlear hair cells are incapable of regeneration, damaged cells cannot be replaced, and as such, their loss leads to permanent hearing loss. Symptoms associated with a neurodegenerative disease include, without limitation, decreased hearing sensitivity and/or sensorineural hearing loss. It is now known that EpHA4 signaling prevents the generation of new cochlear hair cells suggesting that inhibition of EpHA4 activity could be an effective therapy in the treatment of hearing loss.

In another embodiment, a method of treating an EphA4-based disease, disorder or pathology includes a method of treating a hearing loss. In an aspect of this embodiment, a method of treating a hearing loss comprises administering one or more EphA4 antagonists, like one or more APY cyclic peptides disclosed herein, or a pharmaceutical composition disclosed herein to an individual in need thereof in an amount sufficient to reduce one or more physiological conditions or symptom associated with a hearing loss, thereby treating the hearing loss. In an aspect of this embodiment, administration of one or more EphA4 antagonists, like one or more APY cyclic peptides disclosed herein, or a pharmaceutical composition disclosed herein promotes the generation of cochlear sensory hair cells. In an aspect of this embodiment, administration is by injection to the ear region.

Nerve regeneration or neuroregeneration, refers to the regrowth or repair of nervous tissues, cells or cell products. Such mechanisms may include generation of new neurons, glia, axons, myelin, or synapses. Although neuroregeneration differs between the peripheral nervous system (PNS) and the central nervous system (CNS) by the functional mechanisms that control axon regrowth, both are influenced by EphA4 signaling which contribute to the inhibition of axon regeneration following injury. Thus, an EphA4 antagonist, like an APY cyclic peptide disclosed herein, or a pharmaceutical composition disclosed herein can be useful in promoting neuroregeneration by inhibiting the activity of EphA4 signaling. Symptoms associated with a lack of nerve regeneration include, without limitation, abnormal movement, abnormal sensation, limb grasping, muscle weakness, atrophy, paralysis, loss of neuronal function, loss of motor neuron function, loss of sensory neuron function, inhibited neuronal growth, inhibited axon growth, inhibited synaptic plasticity, synaptic loss, astrocytic gliosis and/or glial scarring.

In another embodiment, a method of treating an EphA4-based disease, disorder or pathology includes a method of promoting nerve regeneration. In an aspect of this embodiment, a method of promoting nerve regeneration comprises administering one or more EphA4 antagonists, like one or more APY cyclic peptides disclosed herein, or a pharmaceutical composition disclosed herein to an individual in need thereof in an amount sufficient to stimulate of facilitate neuronal differentiation and/or growth, thereby promoting nerve regeneration.

Following the primary cerebral insult, a cascade of events amplifies the initial damage regardless of the etiology of the precipitating event. Secondary biochemical changes contribute to subsequent tissue damage with associated neuronal cell death. One such secondary chemical response is a growth inhibitory response that prevents axonal regeneration, neurogenesis, synaptogenesis and angiogenesis. EphA4 signaling is known to inhibit neuronal growth following neuronal injury. Thus, an EphA4 antagonist, like an APY cyclic peptide disclosed herein, or a pharmaceutical composition disclosed herein can be useful in providing neuroprotection that minimizes this subsequent damage, where the secondary tissue damage is dependent EphA4 signaling activity because these APY cyclic peptides inhibit EphA4 signaling.

In another embodiment, a method of treating an EphA4-based disease, disorder or pathology includes a method of promoting neuroprotection. In an aspect of this embodiment, a method of promoting neuroprotection comprises administering one or more EphA4 antagonists, like one or more APY cyclic peptides disclosed herein, or a pharmaceutical composition disclosed herein to an individual in need thereof in an amount sufficient to protect neurons or nerve tissue from damage, thereby promoting neuroprotection.

Originally identified as axon guidance molecules, ephrins and Eph receptors are now known to be involved in a vast array of cell communication events. Many A- and B-class receptors were shown to be overexpressed in a wide variety of tumors, including malignant melanoma, glioma, prostate cancer, breast cancer, small cell lung cancer, endometrial cancer, esophageal cancer, gastric cancer, and colorectal cancer. Subsequent work has shown the Eph receptors regulate critical steps of blood vessel formation (vasculogenesis) and remodeling (angiogenesis) and hence tumor growth. Increasing evidence has implicated EphA4 in various types of cancer, including glioblastoma, gastric cancer, pancreatic cancer, prostate cancer and breast cancer. For example, EphA4 downregulation studies have suggested a role for EphA4 in leukemia, prostate cancer, pancreatic cancer and gastric cancer cell growth and in liver cancer metastasis. High EphA4 expression has also been correlated with shorter survival in breast and gastric cancer patients, although the opposite correlation was found in lung cancer patients. EphA4 is also highly upregulated in Sezary syndrome, a leukemic variant of cutaneous T-cell lymphomas. Finally, EphA4 can enhance the oncogenic effects of fibroblast growth factor receptor 1 in glioblastoma cells. Hence, inhibiting EphA4-ephrin interaction could be useful for promoting axon regeneration and neural repair, providing neuroprotection and regulating synaptic plasticity in the nervous system as well as inhibiting the progression of cancer.

In another embodiment, a method of treating an EphA4-based disease, disorder or pathology includes a method of treating a cancer. In an aspect of this embodiment, a method of treating a cancer comprising administering one or more EphA4 antagonists, like one or more APY cyclic peptides disclosed herein, or a pharmaceutical composition disclosed herein to an individual in need thereof in an amount sufficient to reduce one or more physiological conditions or symptom associated with a cancer, thereby treating the cancer. An EphA4 antagonist, like an APY cyclic peptide disclosed herein, or a pharmaceutical composition disclosed herein can be useful in treating any cancer expressing high EphA4 levels. IN an aspect of this embodiment, a cancer, includes, without limitation, glioblastoma, a gastric cancer, a pancreatic cancer, a prostate cancer, a breast cancer, a liver cancer, a leukemia and Sezary syndrome, a leukemic variant of cutaneous T-cell lymphomas.

Aspects of the present invention provide, in part, an individual. An individual comprises any mammal including a human, and a human can be a patient.

Aspects of the present invention provide, in part, administering an APY cyclic peptide disclosed herein, or a pharmaceutical composition disclosed herein. As used herein, the term "administering" refers to any delivery mechanism that provides an APY cyclic peptide disclosed herein, or a pharmaceutical composition disclosed herein to an individual that potentially results in a clinically, therapeutically, or experimentally beneficial result. The actual delivery mechanism used to administer an APY cyclic peptide disclosed herein, or a pharmaceutical composition disclosed herein to an individual can be determined by a person of ordinary skill in the art by taking into account factors, including, without limitation, the type of Eph4A-based disease, the location of the Eph4A-based disease, the cause of the Eph4A-based disease, the severity of the Eph4A-based disease, the degree of relief desired for Eph4A-based disease, the duration of relief desired for Eph4A-based disease, the particular APY cyclic peptide or a pharmaceutical composition used, the rate of excretion of the particular APY cyclic peptide or a pharmaceutical composition used, the pharmacodynamics of the particular APY cyclic peptide or a pharmaceutical composition used, the nature of the other compounds to be included in the pharmaceutical composition, the particular route of administration, the particular characteristics, history and risk factors of the individual, such as, e.g., age, weight, general health and the like, or any combination thereof.

A composition disclosed herein can be administered to an individual using a cellular uptake approach. Administration of a composition disclosed herein using a cellular uptake approach comprise a variety of enteral or parenteral approaches including, without limitation, oral administration in any acceptable form, such as, e.g., tablet, liquid, capsule, powder, or the like; topical administration in any acceptable form, such as, e.g., drops, spray, creams, gels or ointments; intravascular administration in any acceptable form, such as, e.g., intravenous injection, intravenous infusion, intra-arterial injection, intra-arterial infusion and catheter instillation into the vasculature; peri- and intra-tissue administration in any acceptable form, such as, e.g., intra-peritoneal injection, intramuscular injection, subcutaneous injection, subcutaneous infusion, intraocular injection, retinal injection, sub-retinal injection, intrathecal injection, intracerebroventricular injection or epidural injection; intravesicular administration in any acceptable form, such as, e.g., catheter instillation; and by placement device, such as, e.g., an implant, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

An APY cyclic peptide disclosed herein, or a pharmaceutical composition disclosed herein is administered in an amount sufficient to treat an EphA4-based disease, disorder or pathology. In aspects of this embodiment, the amount of an APY cyclic peptide disclosed herein, or a pharmaceutical composition disclosed herein administered is an amount sufficient to reduce one or more physiological conditions or symptom associated with an EphA4-based disease, disorder or pathology or an amount sufficient to protect the individual against an EphA4-based disease, disorder or pathology. As used herein, the term "amount sufficient" includes "effective amount", "effective dose", "therapeutically effective amount" or "therapeutically effective dose" and refers to the minimum amount of an APY cyclic peptide disclosed herein, or a pharmaceutical composition disclosed herein necessary to achieve the desired therapeutic effect and includes an amount sufficient to reduce or inhibit one or more physiological conditions or symptom associated with an EphA4-based disease, disorder or pathology.

In aspects of this embodiment, an effective amount of an APY cyclic peptide disclosed herein, or a pharmaceutical composition disclosed herein reduces or inhibits one or more physiological conditions or symptom associated with an EphA4-based disease, disorder or pathology by, e.g., at least 10%, at least 20%, at least 30%, at least 40%, at least 50%, at least 60%, at least 70%, at least 80%, at least 90% or at least 100%. In other aspects of this embodiment, an effective amount of an APY cyclic peptide disclosed herein, or a pharmaceutical composition disclosed herein reduces or inhibits one or more physiological conditions or symptom associated with an EphA4-based disease, disorder or pathology by, e.g., at most 10%, at most 20%, at most 30%, at most 40%, at most 50%, at most 60%, at most 70%, at most 80%, at most 90% or at most 100%. In yet other aspects of this embodiment, an effective amount of an APY cyclic peptide disclosed herein, or a pharmaceutical composition disclosed herein reduces or inhibits one or more physiological conditions or symptom associated with an EphA4-based disease, disorder or pathology by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, an effective amount of an APY cyclic peptide disclosed herein, or a pharmaceutical composition disclosed herein reduces or inhibits one or more physiological conditions or symptom associated with an EphA4-based disease, disorder or pathology for, e.g., at least one week, at least one month, at least two months, at least three months, at least four months, at least five months, at least six months, at least seven months, at least eight months, at least nine months, at least ten months, at least eleven months, or at least twelve months.

The actual effective amount of an APY cyclic peptide disclosed herein, or a pharmaceutical composition disclosed herein to be administered to an individual can be determined by a person of ordinary skill in the art by taking into account factors, including, without limitation, the type of EphA4-based disease, disorder or pathology, the location of the EphA4-based disease, disorder or pathology, the cause of the EphA4-based disease, disorder or pathology, the severity of the EphA4-based disease, disorder or pathology, the degree of relief desired for EphA4-based disease, disorder or pathology, the duration of relief desired for EphA4-based disease, disorder or pathology, the particular APY cyclic peptide or a pharmaceutical composition used, the rate of excretion of the particular APY cyclic peptide or a pharmaceutical composition used, the pharmacodynamics of the particular APY cyclic peptide or a pharmaceutical composition used, the nature of the other compounds to be included in the pharmaceutical composition, the particular route of administration used, the particular characteristics, history and risk factors of the individual, such as, e.g., age, weight, general health and the like, or any combination thereof. Additionally, where repeated administration of an APY cyclic peptide disclosed herein, or a pharmaceutical composition disclosed herein is used, the actual therapeutically effective amount will further depend upon factors, including, without limitation, the frequency of administration, the half-life of an APY cyclic peptide disclosed herein, or a pharmaceutical composition disclosed herein, or any combination thereof. It is known by a person of ordinary skill in the art that an effective amount of an APY cyclic peptide disclosed herein, or a pharmaceutical composition disclosed herein can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

In other aspects of this embodiment, an effective amount of an APY cyclic peptide disclosed herein, or a pharmaceutical composition disclosed herein generally is in the range of about 0.001 µg/kg/day to about 100 µg/kg/day. In aspects of this embodiment, an effective amount of an APY cyclic peptide disclosed herein, or a pharmaceutical composition disclosed herein may be, e.g., at least 0.001 µg/kg/day, at least 0.01 µg/kg/day, at least 0.1 µg/kg/day, at least 1.0 µg/kg/day, at least 5.0 µg/kg/day, at least 10 µg/kg/day, at least 15 µg/kg/day, at least 20 µg/kg/day, at least 25 µg/kg/day, at least 30 µg/kg/day, at least 35 µg/kg/day, at least 40 µg/kg/day, at least 45 µg/kg/day, or at least 50 µg/kg/day.

In other aspects of this embodiment, an effective amount of an APY cyclic peptide disclosed herein, or a pharmaceutical composition disclosed herein may be in the range of, e.g., about 0.001 µg/kg/day to about 10 µg/kg/day, about 0.001 µg/kg/day to about 15 µg/kg/day, about 0.001 µg/kg/day to about 20 µg/kg/day, about 0.001 µg/kg/day to about 25 µg/kg/day, about 0.001 µg/kg/day to about 30 µg/kg/day, about 0.001 µg/kg/day to about 35 µg/kg/day, about 0.001 µg/kg/day to about 40 µg/kg/day, about 0.001 µg/kg/day to about 45 µg/kg/day, about 0.001 µg/kg/day to about 50 µg/kg/day, about 0.001 µg/kg/day to about 75 µg/kg/day, or about 0.001 µg/kg/day to about 100 µg/kg/day. In yet other aspects of this embodiment, an effective amount of an APY cyclic peptide disclosed herein, or a pharmaceutical composition disclosed herein may be in the range of, e.g., about 0.01 µg/kg/day to about 10 µg/kg/day, about 0.01 µg/kg/day to about 15 µg/kg/day, about 0.01 µg/kg/day to about 20 µg/kg/day, about 0.01 µg/kg/day to about 25 µg/kg/day, about 0.01 µg/kg/day to about 30 µg/kg/day, about 0.01 µg/kg/day to about 35 µg/kg/day, about 0.01 µg/kg/day to about 40 µg/kg/day, about 0.01 µg/kg/day to about 45 µg/kg/day, about 0.01 µg/kg/day to about 50 µg/kg/day, about 0.01 µg/kg/day to about 75 µg/kg/day, or about 0.01 µg/kg/day to about 100 µg/kg/day. In still other aspects of this embodiment, an effective amount of an APY cyclic peptide disclosed herein, or a pharmaceutical composition disclosed herein may be in the range of, e.g., about 0.1 µg/kg/day to about 10 µg/kg/day, about 0.1 µg/kg/day to about 15 µg/kg/day, about 0.1 µg/kg/day to about 20 µg/kg/day, about 0.1 µg/kg/day to about 25 µg/kg/day, about 0.1 µg/kg/day to about 30 µg/kg/day, about 0.1 µg/kg/day to about 35 µg/kg/day, about 0.1 µg/kg/day to about 40 µg/kg/day, about 0.1 µg/kg/day to about 45 µg/kg/day, about 0.1 µg/kg/day to about 50 µg/kg/day, about 0.1 µg/kg/day to about 75 µg/kg/day, or about 0.1 µg/kg/day to about 100 µg/kg/day.

In other aspects of this embodiment, an effective amount of an APY cyclic peptide disclosed herein, or a pharmaceutical composition disclosed herein may be in the range of, e.g., about 1 µg/kg/day to about 10 µg/kg/day, about 1

µg/kg/day to about 15 µg/kg/day, about 1 µg/kg/day to about 20 µg/kg/day, about 1 µg/kg/day to about 25 µg/kg/day, about 1 µg/kg/day to about 30 µg/kg/day, about 1 µg/kg/day to about 35 µg/kg/day, about 1 µg/kg/day to about 40 µg/kg/day, about 1 µg/kg/day to about 45 µg/kg/day, about 1 µg/kg/day to about 50 µg/kg/day, about 1 µg/kg/day to about 75 µg/kg/day, or about 1 µg/kg/day to about 100 µg/kg/day. In yet other aspects of this embodiment, an effective amount of an APY cyclic peptide disclosed herein, or a pharmaceutical composition disclosed herein may be in the range of, e.g., about 5 µg/kg/day to about 10 µg/kg/day, about 5 µg/kg/day to about 15 µg/kg/day, about 5 µg/kg/day to about 20 µg/kg/day, about 5 µg/kg/day to about 25 µg/kg/day, about 5 µg/kg/day to about 30 µg/kg/day, about 5 µg/kg/day to about 35 µg/kg/day, about 5 µg/kg/day to about 40 µg/kg/day, about 5 µg/kg/day to about 45 µg/kg/day, about 5 µg/kg/day to about 50 µg/kg/day, about 5 µg/kg/day to about 75 µg/kg/day, or about 5 µg/kg/day to about 100 µg/kg/day.

In other aspects of this embodiment, an effective amount of an APY cyclic peptide disclosed herein, or a pharmaceutical composition disclosed herein generally is in the range of about 0.001 µg/day to about 100 µg/day. In aspects of this embodiment, an effective amount of an APY cyclic peptide disclosed herein, or a pharmaceutical composition disclosed herein may be, e.g., at least 0.001 µg/day, at least 0.01 µg/day, at least 0.1 µg/day, at least 1.0 µg/day, at least 5.0 µg/day, at least 10 µg/day, at least 15 µg/day, at least 20 µg/day, at least 25 µg/day, at least 30 µg/day, at least 35 µg/day, at least 40 µg/day, at least 45 µg/day, or at least 50 µg/day.

In other aspects of this embodiment, an effective amount of an APY cyclic peptide disclosed herein, or a pharmaceutical composition disclosed herein may be in the range of, e.g., about 0.001 µg/day to about 10 µg/day, about 0.001 µg/day to about 15 µg/day, about 0.001 µg/day to about 20 µg/day, about 0.001 µg/day to about 25 µg/day, about 0.001 µg/day to about 30 µg/day, about 0.001 µg/day to about 35 µg/day, about 0.001 µg/day to about 40 µg/day, about 0.001 µg/day to about 45 µg/day, about 0.001 µg/day to about 50 µg/day, about 0.001 µg/day to about 75 µg/day, or about 0.001 µg/day to about 100 µg/day. In yet other aspects of this embodiment, an effective amount of an APY cyclic peptide disclosed herein, or a pharmaceutical composition disclosed herein may be in the range of, e.g., about 0.01 µg/day to about 10 µg/day, about 0.01 µg/day to about 15 µg/day, about 0.01 µg/day to about 20 µg/day, about 0.01 µg/day to about 25 µg/day, about 0.01 µg/day to about 30 µg/day, about 0.01 µg/day to about 35 µg/day, about 0.01 µg/day to about 40 µg/day, about 0.01 µg/day to about 45 µg/day, about 0.01 µg/day to about 50 µg/day, about 0.01 µg/day to about 75 µg/day, or about 0.01 µg/day to about 100 µg/day. In still other aspects of this embodiment, an effective amount of an APY cyclic peptide disclosed herein, or a pharmaceutical composition disclosed herein may be in the range of, e.g., about 0.1 µg/day to about 10 µg/day, about 0.1 µg/day to about 15 µg/day, about 0.1 µg/day to about 20 µg/day, about 0.1 µg/day to about 25 µg/day, about 0.1 µg/day to about 30 µg/day, about 0.1 µg/day to about 35 µg/day, about 0.1 µg/day to about 40 µg/day, about 0.1 µg/day to about 45 µg/day, about 0.1 µg/day to about 50 µg/day, about 0.1 µg/day to about 75 µg/day, or about 0.1 µg/day to about 100 µg/day.

In other aspects of this embodiment, an effective amount of an APY cyclic peptide disclosed herein, or a pharmaceutical composition disclosed herein may be in the range of, e.g., about 1 µg/day to about 10 µg/day, about 1 µg/day to about 15 µg/day, about 1 µg/day to about 20 µg/day, about 1 µg/day to about 25 µg/day, about 1 µg/day to about 30 µg/day, about 1 µg/day to about 35 µg/day, about 1 µg/day to about 40 µg/day, about 1 µg/day to about 45 µg/day, about 1 µg/day to about 50 µg/day, about 1 µg/day to about 75 µg/day, or about 1 µg/day to about 100 µg/day. In yet other aspects of this embodiment, an effective amount of an APY cyclic peptide disclosed herein, or a pharmaceutical composition disclosed herein may be in the range of, e.g., about 5 µg/day to about 10 µg/day, about 5 µg/day to about 15 µg/day, about 5 µg/day to about 20 µg/day, about 5 µg/day to about 25 µg/day, about 5 µg/day to about 30 µg/day, about 5 µg/day to about 35 µg/day, about 5 µg/day to about 40 µg/day, about 5 µg/day to about 45 µg/day, about 5 µg/day to about 50 µg/day, about 5 µg/day to about 75 µg/day, or about 5 µg/day to about 100 µg/day.

Dosing can be single dosage or cumulative (serial dosing), and can be readily determined by one skilled in the art. For instance, treatment of an EphA4-based disease, disorder or pathology may comprise a one-time administration of an effective amount of an APY cyclic peptide disclosed herein, or a pharmaceutical composition disclosed herein. As a non-limiting example, an effective amount of an APY cyclic peptide disclosed herein, or a pharmaceutical composition disclosed herein can be administered once to an individual, e.g., as a single injection or deposition. Alternatively, treatment of a HIV-based disease may comprise multiple administrations of an effective amount of an APY cyclic peptide disclosed herein, or a pharmaceutical composition disclosed herein carried out over a range of time periods, such as, e.g., daily, once every few days, weekly, monthly or yearly. As a non-limiting example, an APY cyclic peptide disclosed herein, or a pharmaceutical composition disclosed herein can be administered one, two, three, four, five or six times yearly to an individual. The timing of administration can vary from individual to individual, depending upon such factors as the severity of an individual's symptoms. For example, an effective amount of an APY cyclic peptide disclosed herein, or a pharmaceutical composition disclosed herein can be administered to an individual once every three months for an indefinite period of time, or until the individual no longer requires therapy. A person of ordinary skill in the art will recognize that the condition of the individual can be monitored throughout the course of treatment and that the effective amount of an APY cyclic peptide disclosed herein, or a pharmaceutical composition disclosed herein that is administered can be adjusted accordingly.

An APY cyclic peptide disclosed herein, or a pharmaceutical composition disclosed herein can also be administered to an individual in combination with other therapeutic compounds to increase the overall therapeutic effect of the treatment. The use of multiple compounds to treat an indication can increase the beneficial effects while reducing the presence of side effects.

Aspects of the present specification can also be described as follows:

1. An EphA4 receptor antagonist comprising a cyclic peptide comprising or consisting essentially or consisting of the sequence $X_1$-$X_2$-$X_3$-$C_4$-$X_5$-$X_6$-$X_7$-$\beta A_8$-$X_9$-W-$X_{11}$-$C_{12}$ (SEQ ID NO: 3), $X_2$-$X_3$-$C_4$-$X_5$-$X_6$-$X_7$-$\beta A_8$-$X_9$-W-$X_{11}$-$C_{12}$ (SEQ ID NO: 4), or $X_3$-$C_4$-$X_5$-$X_6$-$X_7$-$\beta A_8$-$X_9$-W-$X_{11}$-$C_{12}$ (SEQ ID NO: 5), wherein $X_1$ is independently βA, D-A, A, E, G, Q, D, L, S, F, or Y; $X_2$ is independently P, A, G, Ahx, Ava, γAbu, βA or Sar; $X_3$ is independently Y, F, W, V, L, H or I; $X_5$ is independently V or L; $X_6$ is independently Y, F, W or H; $X_7$ is independently any amino acid; $X_9$ is independently any amino acid; and $X_{11}$ is independently any amino acid; wherein $C_4$ and $C_{12}$ form a disulfide bridge; wherein $C_{12}$ is optionally amidated; and wherein the amino-terminal residue is optionally acetylated.

2. The EphA4 receptor antagonist according to embodiment 1, wherein $X_1$ is independently βA, D-A, A, E, G or Q.

3. The EphA4 receptor antagonist according to embodiment 1 or embodiment 2, wherein $X_1$ is independently βA, D-A, A or E.

4. The EphA4 receptor antagonist according to any one of embodiments 1-3, wherein $X_2$ is P.

5. The EphA4 receptor antagonist according to any one of embodiments 1-4, wherein $X_3$ is independently Y, F, W, V, L or H.

6. The EphA4 receptor antagonist according to any one of embodiments 1-5, wherein $X_3$ is independently Y, F or W.

7. The EphA4 receptor antagonist according to any one of embodiments 1-6, wherein $X_5$ is V.

8. The EphA4 receptor antagonist according to any one of embodiments 1-7, wherein $X_6$ is independently Y, F or W.

9. The EphA4 receptor antagonist according to any one of embodiments 1-8, wherein $X_7$ is independently any amino acid except P; $X_9$ is independently any amino acid except P; and $X_{11}$ is independently any amino acid except P.

10. The EphA4 receptor antagonist according to any one of embodiments 1-9, wherein $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G.

11. The EphA4 receptor antagonist according to any one of embodiments 1-10, wherein $X_7$ is independently R, T, N, D, S, or Q; $X_9$ is independently S, E, T, V, W, R, L, D, Y; and $X_{11}$ is independently S, E, L, N, T, K, V, I or H.

12. The EphA4 receptor antagonist according to any one of embodiments 1-11, wherein $X_7$ is independently R, T, N, D, S, or Q; $X_9$ is independently S, E, T, V, D, Y; and $X_{11}$ is independently S, E, L, N, K, V, I or H.

13. The EphA4 receptor antagonist according to any one of embodiments 1-12, wherein $X_7$ is independently R, T, or N; $X_9$ is independently S, E, T or V; and $X_{11}$ is independently S, E, L or N.

14. The EphA4 receptor antagonist according to any one of embodiments 1, 2, 4, 5 or 10-13, wherein the sequence comprises or consists essentially of or consists of $X_1$-$P_2$-$X_3$-$C_4$-$X_5$-$X_6$-$X_7$-$βA_8$-$X_9$-$W_{10}$-$X_{11}$-$C_{12}$ (SEQ ID NO: 6), $P_2$-$X_3$-$C_4$-$X_5$-$X_6$-$X_7$-$βA_8$-$X_9$-$W_{10}$-$X_{11}$-$C_{12}$ (SEQ ID NO: 7) or $X_3$-$C_4$-$X_5$-$X_6$-$X_7$-$βA_8$-$X_9$-$W_{10}$-$X_{11}$-$C_{12}$ (SEQ ID NO: 8), wherein $X_1$ is independently βA, D-A, A, E, G or Q; $X_3$ is independently Y, F, W, V, L or H; $X_5$ is independently V or L; $X_6$ is independently Y, F, W or H; $X_7$ is independently any amino acid except P; $X_9$ is independently any amino acid except P; and $X_{11}$ is independently any amino acid except P; wherein $C_4$ and $C_{12}$ form a disulfide bridge; wherein $C_{12}$ is optionally amidated; and wherein the amino-terminal residue is optionally acetylated.

15. The EphA4 receptor antagonist according to embodiment 14, wherein $X_1$ is independently βA, D-A, A or E.

16. The EphA4 receptor antagonist according to embodiment 14 or embodiment 15, wherein $X_3$ is independently Y, F or W.

17. The EphA4 receptor antagonist according to any one of embodiments 14-16, wherein $X_5$ is V.

18. The EphA4 receptor antagonist according to any one of embodiments 14-17, wherein $X_6$ is independently Y, F or W.

19. The EphA4 receptor antagonist according to any one of embodiments 14-18, wherein $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G.

20. The EphA4 receptor antagonist according to any one of embodiments 14-10, wherein $X_7$ is independently R, T, N, D, S, or Q; $X_9$ is independently S, E, T, V, W, R, L, D, Y; and $X_{11}$ is independently S, E, L, N, T, K, V, I or H.

21. The EphA4 receptor antagonist according to any one of embodiments 14-20, wherein $X_7$ is independently R, T, N, D, S, or Q; $X_9$ is independently S, E, T, V, D, Y; and $X_{11}$ is independently S, E, L, N, K, V, I or H.

22. The EphA4 receptor antagonist according to any one of embodiments 11-21, wherein $X_7$ is independently R, T, or N; $X_9$ is independently S, E, T or V; and $X_{11}$ is independently S, E, L or N.

23. The EphA4 receptor antagonist according to any one of embodiments 1, 2, 5, 7 or 10-13, wherein the sequence comprises or consists essentially of or consists of $X_1$-$X_2$-$X_3$-$C_4$-$V_6$-$X_6$-$X_7$-$βA_8$-$X_9$-$W_{10}$-$X_{11}$-$C_{12}$ (SEQ ID NO: 9), $X_2$-$X_3$-$C_4$-$V_6$-$X_6$-$X_7$-$βA_8$-$X_9$-$W_{10}$-$X_{11}$-$C_{12}$ (SEQ ID NO: 10) or $X_3$-$C_4$-$V_6$-$X_6$-$X_7$-$βA_8$-$X_9$-$W_{10}$-$X_{11}$-$C_{12}$ (SEQ ID NO: 11), wherein $X_1$ is independently βA, D-A, A, E, G or Q; $X_2$ is independently P, A, G, Ahx, Ava, γAbu, βA or Sar; $X_3$ is independently Y, F, W, V, L or H; $X_6$ is independently Y, F, W or H; $X_7$ is independently any amino acid except P; $X_9$ is independently any amino acid except P; and $X_{11}$ is independently any amino acid except P; wherein $C_4$ and $C_{12}$ form a disulfide bridge; wherein $C_{12}$ is optionally amidated; and wherein the amino-terminal residue is optionally acetylated.

24. The EphA4 receptor antagonist according to embodiment 23, wherein $X_1$ is independently βA, D-A, A or E.

25. The EphA4 receptor antagonist according to embodiment 23 or embodiment 24, wherein $X_2$ is P.

26. The EphA4 receptor antagonist according to any one of embodiments 23-25, wherein $X_3$ is independently Y, F or W.

27. The EphA4 receptor antagonist according to any one of embodiments 23-26, wherein $X_6$ is independently Y, F or W.

28. The EphA4 receptor antagonist according to any one of embodiments 23-27, wherein $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G.

29. The EphA4 receptor antagonist according to any one of embodiments 23-28, wherein $X_7$ is independently R, T, N, D, S, or Q; $X_9$ is independently S, E, T, V, W, R, L, D, Y; and $X_{11}$ is independently S, E, L, N, T, K, V, I or H.

30. The EphA4 receptor antagonist according to any one of embodiments 23-29, wherein $X_7$ is independently R, T, N, D, S, or Q; $X_9$ is independently S, E, T, V, D, Y; and $X_{11}$ is independently S, E, L, N, K, V, I or H.

31. The EphA4 receptor antagonist according to any one of embodiments 23-30, wherein $X_7$ is independently R, T, or N; $X_9$ is independently S, E, T or V; and $X_{11}$ is independently S, E, L or N.

32. The EphA4 receptor antagonist according to any one of embodiments 1, 2, 5 or 10-13, wherein the sequence comprises or consists essentially of or consists of $X_1$-$P_2$-$X_3$-$C_4$-$V_6$-$X_6$-$X_7$-$βA_8$-$X_9$-$W_{10}$-$X_{11}$-$C_{12}$ (SEQ ID NO: 12), $P_2$-$X_3$-$C_4$-$V_6$-$X_6$-$X_7$-$βA_8$-$X_9$-$W_{10}$-$X_{11}$-$C_{12}$ (SEQ ID NO: 13) or $X_3$-$C_4$-$V_6$-$X_6$-$X_7$-$βA_8$-$X_9$-$W_{10}$-$X_{11}$-$C_{12}$ (SEQ ID NO: 14), wherein $X_1$ is independently βA, D-A, A, E, G or Q; $X_3$ is independently Y, F, W, V, L or H; $X_6$ is independently Y, F, W or H; $X_7$ is independently any amino acid except P; $X_9$ is independently any amino acid except P; and $X_{11}$ is independently any amino acid except P; wherein $C_4$ and $C_{12}$ form a disulfide bridge; wherein $C_{12}$ is optionally amidated; and wherein the amino-terminal residue is optionally acetylated.

33. The EphA4 receptor antagonist according to embodiment 32, wherein $X_1$ is independently βA, D-A, A or E.
34. The EphA4 receptor antagonist according to embodiment 32 or embodiment 33, wherein $X_3$ is independently Y, F or W.
35. The EphA4 receptor antagonist according to any one of embodiments 32-34, wherein $X_6$ is independently Y, F or W.
36. The EphA4 receptor antagonist according to any one of embodiments 32-35, wherein $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G.
37. The EphA4 receptor antagonist according to any one of embodiments 32-36, wherein $X_7$ is independently R, T, N, D, S, or Q; $X_9$ is independently S, E, T, V, W, R, L, D, Y; and $X_{11}$ is independently S, E, L, N, T, K, V, I or H.
38. The EphA4 receptor antagonist according to any one of embodiments 32-37, wherein $X_7$ is independently R, T, N, D, S, or Q; $X_9$ is independently S, E, T, V, D, Y; and $X_{11}$ is independently S, E, L, N, K, V, I or H.
39. The EphA4 receptor antagonist according to any one of embodiments 32-38, wherein $X_7$ is independently R, T, or N; $X_9$ is independently S, E, T or V; and $X_{11}$ is independently S, E, L or N.
40. The EphA4 receptor antagonist according to any one of embodiments 1, 2 or 10-13, wherein the sequence comprises or consists essentially of or consists of $X_1$-$P_2$-$Y_3$-$C_4$-$V_5$-$X_6$-$X_7$-$βA_8$-$X_9$-$W_{10}$-$X_{11}$-$C_{12}$ (SEQ ID NO: 15), $P_2$-$Y_3$-$C_4$-$V_5$-$X_6$-$X_7$-$βA_8$-$X_9$-$W_{10}$-$X_{11}$-$C_{12}$ (SEQ ID NO: 16) or $Y_3$-$C_4$-$V_5$-$X_6$-$X_7$-$βA_8$-$X_9$-$W_{10}$-$X_{11}$-$C_{12}$ (SEQ ID NO: 17), wherein $X_1$ is independently βA, D-A, A, E, G or Q; $X_6$ is independently Y, F, W or H; $X_7$ is independently any amino acid except P; $X_9$ is independently any amino acid except P; and $X_{11}$ is independently any amino acid except P; wherein $C_4$ and $C_{12}$ form a disulfide bridge; wherein $C_{12}$ is optionally amidated; and wherein the amino-terminal residue is optionally acetylated.
41. The EphA4 receptor antagonist according to embodiment 40, wherein $X_1$ is independently βA, D-A, A or E.
42. The EphA4 receptor antagonist according to embodiment 40 or embodiment 41, wherein $X_6$ is independently Y, F or W.
43. The EphA4 receptor antagonist according to any one of embodiments 40-42, wherein $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G.
44. The EphA4 receptor antagonist according to any one of embodiments 40-43, wherein $X_7$ is independently R, T, N, D, S, or Q; $X_9$ is independently S, E, T, V, W, R, L, D, Y; and $X_{11}$ is independently S, E, L, N, T, K, V, I or H.
45. The EphA4 receptor antagonist according to any one of embodiments 40-44, wherein $X_7$ is independently R, T, N, D, S, or Q; $X_9$ is independently S, E, T, V, D, Y; and $X_{11}$ is independently S, E, L, N, K, V, I or H.
46. The EphA4 receptor antagonist according to any one of embodiments 40-45, wherein $X_7$ is independently R, T, or N; $X_9$ is independently S, E, T or V; and $X_{11}$ is independently S, E, L or N.
47. The EphA4 receptor antagonist according to any one of embodiments 1, 2, 5 or 10-13, wherein the sequence comprises or consists essentially of or consists of $X_1$-$P_2$-$X_3$-$C_4$-$V_5$-$Y_6$-$X_7$-$βA_8$-$X_9$-$W_{10}$-$X_{11}$-$C_{12}$ (SEQ ID NO: 18), $P_2$-$X_3$-$C_4$-$V_5$-$Y_6$-$X_7$-$βA_8$-$X_9$-$W_{10}$-$X_{11}$-$C_{12}$ (SEQ ID NO: 19) or $X_3$-$C_4$-$V_5$-$Y_6$-$X_7$-$βA_8$-$X_9$-$W_{10}$-$X_{11}$-$C_{12}$ (SEQ ID NO: 20), wherein $X_1$ is independently βA, D-A, A, E, G or Q; $X_3$ is independently Y, F, W, V, L or H; $X_7$ is independently any amino acid except P; $X_9$ is independently any amino acid except P; and $X_{11}$ is independently any amino acid except P; wherein $C_4$ and $C_{12}$ form a disulfide bridge; wherein $C_{12}$ is optionally amidated; and wherein the amino-terminal residue is optionally acetylated.
48. The EphA4 receptor antagonist according to embodiment 47, wherein $X_1$ is independently βA, D-A, A or E.
49. The EphA4 receptor antagonist according to embodiment 47 or embodiment 48, wherein $X_3$ is independently Y, F or W.
50. The EphA4 receptor antagonist according to any one of embodiments 47-49, wherein $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G.
51. The EphA4 receptor antagonist according to any one of embodiments 47-50, wherein $X_7$ is independently R, T, N, D, S, or Q; $X_9$ is independently S, E, T, V, W, R, L, D, Y; and $X_{11}$ is independently S, E, L, N, T, K, V, I or H.
52. The EphA4 receptor antagonist according to any one of embodiments 47-51, wherein $X_7$ is independently R, T, N, D, S, or Q; $X_9$ is independently S, E, T, V, D, Y; and $X_{11}$ is independently S, E, L, N, K, V, I or H.
53. The EphA4 receptor antagonist according to any one of embodiments 47-52, wherein $X_7$ is independently R, T, or N; $X_9$ is independently S, E, T or V; and $X_{11}$ is independently S, E, L or N.
54. The EphA4 receptor antagonist according to any one of embodiments 1, 2 or 10-13, wherein the sequence comprises or consists essentially of or consists of $X_1$-$P_2$-$Y_3$-$C_4$-$V_5$-$Y_6$-$X_7$-$βA_8$-$X_9$-$W_{10}$-$X_{11}$-$C_{12}$ (SEQ ID NO: 21), $P_2$-$Y_3$-$C_4$-$V_5$-$Y_6$-$X_7$-$βA_8$-$X_9$-$W_{10}$-$X_{11}$-$C_{12}$ (SEQ ID NO: 22) or $Y_3$-$C_4$-$V_5$-$Y_6$-$X_7$-$βA_8$-$X_9$-$W_{10}$-$X_{11}$-$C_{12}$ (SEQ ID NO: 23), wherein $X_1$ is independently βA, D-A, A, E, G or Q; $X_7$ is independently any amino acid except P; $X_9$ is independently any amino acid except P; and $X_{11}$ is independently any amino acid except P; wherein $C_4$ and $C_{12}$ form a disulfide bridge; wherein $C_{12}$ is optionally amidated; and wherein the amino-terminal residue is optionally acetylated.
55. The EphA4 receptor antagonist according to embodiment 54, wherein $X_1$ is independently βA, D-A, A or E.
56. The EphA4 receptor antagonist according to embodiment 54 or embodiment 55, wherein $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G.
57. The EphA4 receptor antagonist according to any one of embodiments 54-56, wherein $X_7$ is independently R, T, N, D, S, or Q; $X_9$ is independently S, E, T, V, W, R, L, D, Y; and $X_{11}$ is independently S, E, L, N, T, K, V, I or H.
58. The EphA4 receptor antagonist according to any one of embodiments 54-57, wherein $X_7$ is independently R, T, N, D, S, or Q; $X_9$ is independently S, E, T, V, D, Y; and $X_{11}$ is independently S, E, L, N, K, V, I or H.
59. The EphA4 receptor antagonist according to any one of embodiments 54-57, wherein $X_7$ is independently R, T, or N; $X_9$ is independently S, E, T or V; and $X_{11}$ is independently S, E, L or N.
60. The EphA4 receptor antagonist according to any one of embodiments 1, 2 or 10-13, wherein the sequence comprises or consists essentially of or consists of $X_1$-$P_2$-$Y_3$-$C_4$-$V_5$-$Y_6$-$R_7$-$\beta A_8$-$X_9$-$W_{10}$-$X_{11}$-$C_{12}$ (SEQ ID NO: 24), $P_2$-$Y_3$-$C_4$-$V_5$-$Y_6$-$R_7$-$\beta A_8$-$X_9$-$W_{10}$-$X_{11}$-$C_{12}$ (SEQ ID NO: 25) or $Y_3$-$C_4$-$V_5$-$Y_6$-$R_7$-$\beta A_8$-$X_9$-$W_{10}$-$X_{11}$-$C_{12}$ (SEQ ID NO: 26), wherein $X_1$ is independently βA, D-A, A, E, G or Q; $X_9$ is independently any amino acid except P; and $X_{11}$ is independently any amino acid except P; wherein $C_4$ and $C_{12}$ form a disulfide bridge; wherein $C_{12}$ is optionally amidated; and wherein the amino-terminal residue is optionally acetylated.

61. The EphA4 receptor antagonist according to embodiment 60, wherein $X_1$ is independently βA, D-A, A or E.
62. The EphA4 receptor antagonist according to embodiment 60 or embodiment 61, wherein $X_9$ is independently S, E, T, V, D, Y, Q, V, W, R, N, L, K or H; and $X_{11}$ is independently S, E, L, N, V, I, H, K, M, D, W, T or G.
63. The EphA4 receptor antagonist according to any one of embodiments 60-62, wherein $X_9$ is independently S, E, T, V, W, R, L, D, Y; and $X_{11}$ is independently S, E, L, N, T, K, V, I or H.
64. The EphA4 receptor antagonist according to any one of embodiments 60-63, wherein $X_9$ is independently S, E, T, V, D, Y; and $X_{11}$ is independently S, E, L, N, K, V, I or H.
65. The EphA4 receptor antagonist according to any one of embodiments 60-64 wherein $X_9$ is independently S, E, T or V; and $X_{11}$ is independently S, E, L or N.
66. The EphA4 receptor antagonist according to any one of embodiments 1-65, wherein $C_{12}$ is amidated.
67. The EphA4 receptor antagonist according to any one of embodiments 1-66, having a length of about 10 amino acids to about 12 amino acids.
68. The EphA4 receptor antagonist according to any one of embodiments 1-67, having a length 12 amino acids.
69. The EphA4 receptor antagonist according to any one of embodiments 1-68, wherein the sequence is APYCVYRβASWSC (SEQ ID NO: 35), APYCVYRβASWSC-am (SEQ ID NO: 36), APYCVYKβASWSC-am (SEQ ID NO: 45), βAPYCVYRβASWSC (SEQ ID NO: 46), βAPYCVYRβASWSC-am (SEQ ID NO: 47), βAPYCVYKβASWSC-am (SEQ ID NO: 48), βAPYCVYRβAEWEC (SEQ ID NO: 49), βAPYCVYRβAEWEC-am (SEQ ID NO: 50), D-APYCVYRβASWSC (SEQ ID NO: 51), D-APYCVYRβASWSC-am (SEQ ID NO: 52), APYCVWRβASWSC (SEQ ID NO: 53), APYCVYTβAEWLC (SEQ ID NO: 54), APYCVYNβATWNC (SEQ ID NO: 55), APYCVYRβAVWEC (SEQ ID NO: 56), APVCVWRβASWSC (SEQ ID NO: 57), APLCVWRβASWSC (SEQ ID NO: 58), APLCVYRβASWSC (SEQ ID NO: 59), APWCVFRβASWSC (SEQ ID NO: 60), APHCVFRβASWSC (SEQ ID NO: 61), APFCLYTβADWVC (SEQ ID NO: 62), APYCVYDβATWIC (SEQ ID NO: 63), APYCVYSβATWHC (SEQ ID NO: 64), APYCVYDβASWNC (SEQ ID NO: 65), APYCVYQβAYWKC (SEQ ID NO: 66), APYCVYRβASWSC (SEQ ID NO: 67), EPYCVYRβASWSC (SEQ ID NO: 68), APLCVYRβASWSC (SEQ ID NO: 69), Ahx-YCVYRβASWSC-am (SEQ ID NO: 119), Ava-YCVYRβASWSC-am (SEQ ID NO: 120), γAbu-YCVYRβASWSC-am (SEQ ID NO: 121), βA-YCVYRβASWSC-am (SEQ ID NO: 122), GYCVYRβASWSC-am (SEQ ID NO: 123) or Sar1-Y-βAla8.am (SEQ ID NO: 124).

70. The EphA4 receptor antagonist according to embodiment 69, wherein the sequence is APYCVYRβASWSC-am (SEQ ID NO: 36), APYCVYKβASWSC-am (SEQ ID NO: 45), βAPYCVYRβASWSC (SEQ ID NO: 46), βAPYCVYRβASWSC-am (SEQ ID NO: 47), βAPYCVYRβAEWEC-am (SEQ ID NO: 50), D-APYCVYRβASWSC-am (SEQ ID NO: 52), APYCVWRβASWSC (SEQ ID NO: 53), APYCVYTβAEWLC (SEQ ID NO: 54), APYCVYNβATWNC (SEQ ID NO: 55) or APYCVYRβAVWEC (SEQ ID NO: 56).

71. The EphA4 receptor antagonist according to embodiment 70, wherein the sequence is APYCVYRβASWSC-am (SEQ ID NO: 36), βAPYCVYRβASWSC-am (SEQ ID NO: 47) or βAPYCVYRβAEWEC-am (SEQ ID NO: 50).

72. The EphA4 receptor antagonist according to any one of embodiments 1-71, wherein the amino-terminal residue is acetylated or wherein the amino-terminal residue is modified with carboxybenzyl or wherein the amino-terminal residue is not acetylated or is not modified with carboxybenzyl.

73. The EphA4 receptor antagonist according to any one of embodiments 1-72, wherein the EphA4 receptor antagonist has an association rate constant for an EphA4 receptor of less than $1\times10^5$ $M^{-1}$ $s^{-1}$, $5\times10^5$ $M^{-1}$ $s^{-1}$, less than $1\times10^6$ $M^{-1}$ $s^{-1}$, less than $5\times10^6$ $M^{-1}$ $s^{-1}$, less than $1\times10^7$ $M^{-1}$ $s^{-1}$, less than $5\times10^7$ $M^{-1}$ $s^{-1}$ or less than $1\times10^8$ $M^{-1}$ $s^{-1}$.

74. The EphA4 receptor antagonist according to any one of embodiments 1-73, wherein the EphA4 receptor antagonist has an association rate constant for an EphA4 receptor of between $1\times10^5$ $M^{-1}$ $s^{-1}$ to $1\times10^8$ $M^{-1}$ $s^{-1}$, $1\times10^6$ $M^{-1}$ $s^{-1}$ to $1\times10^8$ $M^{-1}$ $s^{-1}$, $1\times10^5$ $M^{-1}$ $s^{-1}$ to $1\times10^7$ $M^{-1}$ $s^{-1}$ or $1\times10^6$ $M^{-1}$ $s^{-1}$ to $1\times10^7$ $M^{-1}$ $s^{-1}$.

75. The EphA4 receptor antagonist according to any one of embodiments 1-74, wherein the EphA4 receptor antagonist has a disassociation rate constant for an EphA4 receptor of less than $1\times10^{-3}$ $s^{-1}$, $5\times10^{-3}$ $s^{-1}$, less than $1\times10^{-4}$ $s^{-1}$, less than $5\times10^{-4}$ $s^{-1}$ or less than $1\times10^{-5}$ $s^{-1}$.

76. The EphA4 receptor antagonist according to any one of embodiments 1-75, wherein the EphA4 receptor antagonist has a disassociation rate constant for an EphA4 receptor of between $1\times10^{-3}$ $s^{-1}$ to $1\times10^{-5}$ $s^{-1}$, $1\times10^{-3}$ $s^{-1}$ to $1\times10^{-4}$ $s^{-1}$ or $1\times10^{-4}$ $s^{-1}$ to $1\times10^{-5}$ $s^{-1}$.

77. The EphA4 receptor antagonist according to any one of embodiments 1-76, wherein the EphA4 receptor antagonist has a disassociation rate constant for an ephrin receptor other than an EpHA4 receptor of less than $1\times10^0$ $M^{-1}$ $s^{-1}$, $5\times10^0$ $M^{-1}$ $s^{-1}$, less than $1\times10^1$ $M^{-1}$ $s^{-1}$, less than $5\times10^1$ $M^{-1}$ $s^{-1}$, less than $1\times10^2$ $M^{-1}$ $s^{-1}$, less than $5\times10^2$ $M^{-1}$ $s^{-1}$, less than $1\times10^3$ $M^{-1}$ $s^{-1}$, less than $5\times10^3$ $M^{-1}$ $s^{-1}$ or less than $1\times10^4$ $M^{-1}$ $s^{-1}$.

78. The EphA4 receptor antagonist according to any one of embodiments 1-77, wherein the EphA4 receptor antagonist has a disassociation rate constant for an ephrin receptor other than an EpHA4 receptor of at most $1\times10^0$ $M^{-1}$ $s^{-1}$, at most $5\times10^0$ $M^{-1}$ $s^{-1}$, at most $1\times10^1$ $M^{-1}$ $s^{-1}$, at most $5\times10^1$ $M^{-1}$ $s^{-1}$, at most $1\times10^2$ $M^{-1}$ $s^{-1}$, at most $5\times10^2$ $M^{-1}$ $s^{-1}$, at most $1\times10^3$ $M^{-1}$ $s^{-1}$, at most $5\times10^3$ $M^{-1}$ $s^{-1}$ or at most $1\times10^4$ $M^{-1}$ $s^{-1}$.

79. The EphA4 receptor antagonist according to any one of embodiments 1-78, wherein the EphA4 receptor antagonist has an equilibrium disassociation rate constant for an EphA4 receptor less than 500 nM, less than 450 nM, less than 400 nM, less than 350 nM, less than 300 nM, less than 250 nM, less than 200 nM, less than 150 nM, less than 100 nM, less than 75 nM, less than 50 nM, less than 25 nM, less than 20 nM, less than 15 nM, less than 10 nM, less than 5 nM, less than 1 nM, less than 0.5 nM or less than 0.1 nM.

80. The EphA4 receptor antagonist according to any one of embodiments 1-79, wherein the EphA4 receptor antagonist has an equilibrium disassociation rate constant for an EphA4 receptor of between about 0.1 nM to about 10 nM, about 0.1 nM to about 25 nM, about 0.1 nM to about 75 nM, about 0.1 nM to about 100 nM, about 0.1 nM to about 125 nM, about 0.1 nM to about 150 nM, about 0.5 nM to about 10 nM, about 0.5 nM to about 25 nM, about 0.5 nM to about 75 nM, about 0.5 nM to about 100 nM, about 0.5 nM to about 125 nM, about 0.5 nM to about 150 nM, about 1 nM to about 10 nM, about 1 nM to about 25 nM, about 1 nM to about 75 nM, about 1 nM to about 100 nM, about 1 nM to about 125 nM, about 1 nM to about 150 nM, about 5 nM to about 10 nM, about 5 nM to about 25 nM, about 5 nM to about 75 nM, about 5 nM to about 100 nM, about 5 nM to about 125 nM, about 5 nM to about 150 nM, about 10 nM to about 25 nM, about 10 nM to about 50 nM, about 10 nM to about 75 nM, about 10 nM to about 100 nM, about 10 nM to about 125 nM, about 10 nM to about 150 nM, about 10 nM to about 175 nM or about 10 nM to about 200 nM.

81. The EphA4 receptor antagonist according to any one of embodiments 1-80, wherein the EphA4 receptor antagonist has an association rate constant for an ephrin-binding pocket of an ephrin receptor other than an EphA4 receptor of less than $1\times10^0$ $M^{-1}$ $s^{-1}$, less than $1\times10^1$ $M^{-1}$ $s^{-1}$, less than $1\times10^2$ $M^{-1}$ $s^{-1}$, less than $1\times10^3$ $M^{-1}$ $s^{-1}$ or less than $1\times10^4$ $M^{-1}$ $s^{-1}$.

82. The EphA4 receptor antagonist according to any one of embodiments 1-81, wherein the EphA4 receptor antagonist has an association rate constant for an ephrin-binding pocket of an ephrin receptor other than an EphA4 receptor of at most $1\times10^0$ $M^{-1}$ $s^{-1}$, at most $1\times10^1$ $M^{-1}$ $s^{-1}$, at most $1\times10^2$ $M^{-1}$ $s^{-1}$, at most $1\times10^3$ $M^{-1}$ $s^{-1}$ or at most $1\times10^4$ $M^{-1}$ $s^{-1}$.

83. The EphA4 receptor antagonist according to any one of embodiments 1-82, wherein the EphA4 receptor antagonist has an association rate constant for an ephrin-binding pocket of an ephrin receptor other than an EphA4 receptor of at least 2-fold more, at least 3-fold more, at least 4-fold more, at least 5-fold more, at least 6-fold more, at least 7-fold more, at least 8-fold more, or at least 9-fold more, at least 10-fold more, at least 20-fold more, at least 30-fold more, at least 40-fold more, at least 50-fold more, at least 60-fold more, at least 70-fold more, at least 80-fold more, at least 90-fold more, at least 100-fold more, at least 200-fold more, at least 300-fold more, at least 400-fold more, at least 500-fold more, at least 600-fold more, at least 700-fold more, at least 800-fold more, at least 900-fold more, at least 1,000-fold more, at least 2,500-fold more, at least 5,000-fold more, at least 7,500-fold more or at least 10,000-fold more.

84. The EphA4 receptor antagonist according to any one of embodiments 1-83, wherein the EphA4 receptor antagonist has an association rate constant for an ephrin-binding pocket of an ephrin receptor other than an EphA4 receptor of at most 1-fold more, at most 2-fold more, at most 3-fold more, at most 4-fold more, at most 5-fold more, at most 6-fold more, at most 7-fold more, at most 8-fold more, or at most 9-fold more, at most 10-fold more, at most 20-fold more, at most 30-fold more, at most 40-fold more, at most 50-fold more, at most 60-fold more, at most 70-fold more, at most 80-fold more, at most 90-fold more, at most 100-fold more, at most 200-fold more, at most 300-fold more, at most 400-fold more, at most 500-fold more, at most 600-fold more, at most 700-fold more, at most 800-fold more, at most 900-fold more, at most 1,000-fold more, at most 2,500-fold more, at most 5,000-fold more, at most 7,500-fold more or at most 10,000-fold more.

85. The EphA4 receptor antagonist according to any one of embodiments 1-84, wherein the EphA4 receptor antagonist has a binding specificity ratio for the ephrin-binding pocket in the EphA4 ligand binding domain relative to an ephrin-binding pocket of an ephrin receptor other than an EphA4 receptor of at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1.

86. The EphA4 receptor antagonist according to any one of embodiments 1-85, wherein the EphA4 receptor antagonist reduces EphA4 receptor activity by at least 10%, at least 20%, at least 30%, at least 40%, at least 50%, at least 60%, at least 70%, at least 80%, at least 60%, or at least 100%.

87. The EphA4 receptor antagonist according to any one of embodiments 1-86, wherein the EphA4 receptor antagonist has a biological half-life of at least 12 hours, at least 18 hours, at least 24 hours, at least 30 hours, at least 36 hours, at least 42 hours, at least 48 hours, at least 54 hours, at least 60 hours, at least 66 hours, at least 72 hours, at least 78 hours, at least 84 hours, at least 90 hours or at least 96 hours.

88. The EphA4 receptor antagonist according to any one of embodiments 1-87, wherein the EphA4 receptor antagonist has a biological half-life of about 12 hours to about 24 hours, about 12 hours to about 36 hours, about 12 hours to about 48 hours, about 12 hours to about 60 hours, about 12 hours to about 72 hours, about 12 hours to about 84 hours, about 12 hours to about 96 hours, about 24 hours to about 36 hours, about 24 hours to about 48 hours, about 24 hours to about 60 hours, about 24 hours to about 72 hours, about 24 hours to about 84 hours, about 24 hours to about 96 hours, about 36 hours to about 48 hours, about 36 hours to about 60 hours, about 36 hours to about 72 hours, about 36 hours to about 84 hours, about 36 hours to about 96 hours, about 48 hours to about 60 hours, about 48 hours to about 72 hours, about 48 hours to about 84 hours, about 48 hours to about 96 hours, about 60 hours to about 72 hours, about 60 hours to about 84 hours, about 60 hours to about 96 hours, about 72 hours to about 84 hours, about 72 hours to about 96 hours or about 84 hours to about 96 hours.

89. The EphA4 receptor antagonist according to any one of embodiments 1-88, wherein the EphA4 receptor antagonist has a plasma half-life of at least 12 hours, at least 18 hours, at least 24 hours, at least 30 hours, at least 36 hours, at least 42 hours, at least 48 hours, at least 54 hours, at least 60 hours, at least 66 hours, at least 72 hours, at least 78 hours, at least 84 hours, at least 90 hours or at least 96 hours.

90. The EphA4 receptor antagonist according to any one of embodiments 1-89, wherein the EphA4 receptor antagonist has a plasma half-life of about 12 hours to about 24 hours, about 12 hours to about 36 hours, about 12 hours to about 48 hours, about 12 hours to about 60 hours, about 12 hours to about 72 hours, about 12 hours to about 84 hours, about 12 hours to about 96 hours, about 24 hours to about 36 hours, about 24 hours to about 48 hours, about 24 hours to about 60 hours, about 24 hours to about 72 hours, about 24 hours to about 84 hours, about 24 hours to about 96 hours, about 36 hours to about 48 hours, about 36 hours to about 60 hours, about 36 hours to about 72 hours, about 36 hours to about 84 hours, about 36 hours to about 96 hours, about 48 hours to about 60 hours, about 48 hours to about 72 hours, about 48 hours to about 84 hours, about 48 hours to about 96 hours, about 60 hours to about 72 hours, about 60 hours to about 84 hours, about 60 hours to about 96 hours, about 72 hours to about 84 hours, about 72 hours to about 96 hours or about 84 hours to about 96 hours.

91. A pharmaceutical composition comprising one or more EphA4 receptor antagonist according to any one of embodiments 1-90.

92. The pharmaceutical composition according to embodiment 91, wherein the one or more EphA4 receptor antagonist are each present in an amount of between about 100 ng to about 1,000 µg.

93. The pharmaceutical composition according to embodiment 91 or embodiment 92, wherein the pharmaceutical composition further comprises one or more pharmaceutical acceptable carriers.

94. A method of treating an EphA4-based disease, disorder or pathology, the method comprising administering an EphA4 receptor antagonist as defined in any one of embodiments 1-90 or a pharmaceutical composition as defined in any one of embodiments 90-93 to an individual in need thereof, wherein administration reduces one or more symptoms associated with the EphA4-based disease, disorder or pathology.

95. The method according to embodiment 94, wherein the EphA4-based disease, disorder or pathology comprises a condition, a disease, a disorder and/or pathology where a pathophysiology effect is due to dysregulation of EphA4 signaling in a manner that causes EphA4 signaling hyperactivity in cells or spatially or temporally aberrant EphA4 signaling.

96. The method according to embodiment 94 or embodiment 95, wherein the EphA4-based disease, disorder or pathology is a neurodegenerative disease, a hearing loss, a promotion of nerve regeneration, a promotion of neuroprotection, or a cancer.

97. A method of treating a neurodegenerative disease, the method comprising administering an EphA4 receptor antagonist as defined in any one of embodiments 1-90 or a pharmaceutical composition as defined in any one of embodiments 90-93 to an individual in need thereof, wherein administration reduces one or more symptoms associated with the neurodegenerative disease.

98. The method according to embodiment 97, wherein the neurodegenerative disease is an Alexander disease, an Alper's disease, Alzheimer's disease, an amyotrophic lateral sclerosis, an ataxia telangiectasia, a Canavan disease, a Cockayne syndrome, a corticobasal degeneration, a Creutzfeldt-Jakob disease, a Guillain-Barre Syndrome a HIV-induced neurodegeneration, a Huntington disease, a Kennedy's disease, a Krabbe disease, a Lewy body dementia, a Machado-Joseph disease, a multiple sclerosis, a Parkinson's disease, a Pelizaeus-Merzbacher disease, a Pick's disease, a primary lateral sclerosis, a Refsum's disease, a Sandhoff disease, a Schilder's disease, a spinal cord injury, a Steele-Richardson-Olszewski disease, a stroke, a tabes dorsalis and/or a traumatic brain injury.

99. The method according to embodiment 97 or embodiment 98, wherein the one or more symptoms include abnormal movement, abnormal sensation, limb grasping, muscle weakness, atrophy, paralysis, abnormal inhibition of axon growth, abnormal axonal transport, aberrant synaptic function, synaptic transmission loss, impaired synaptic plasticity, synaptic loss, neuronal degeneration, motor neuron degeneration, motor neuron loss, poor neuronal survival, memory loss, impaired learning, dementia, β-amyloid plaque deposits, aberrant neurofilament accumulation, reactive astroglia and/or reactive microglia.

100. A method of treating a hearing loss, the method comprising administering an EphA4 receptor antagonist as defined in any one of embodiments 1-90 or a pharmaceutical composition as defined in any one of embodiments 90-93 to an individual in need thereof, wherein administration reduces one or more symptoms associated with the hearing loss.

101. The method according to embodiment 100, wherein administration of the pharmaceutical composition promotes generation of new cochlear sensory hair cells.

102. The method according to embodiment 100 or embodiment 101, wherein the one or more symptoms include decreased hearing sensitivity and sensorineural hearing loss.

103. A method of promoting nerve regeneration, the method comprising administering an EphA4 receptor antagonist as defined in any one of embodiments 1-90 or a pharmaceutical composition as defined in any one of embodiments 90-93 to an individual in need thereof in an amount sufficient to stimulate of facilitate neuronal differentiation and/or growth, thereby promoting nerve regeneration.

104. A method of promoting neuroprotection, the method comprising administering an EphA4 receptor antagonist as defined in any one of embodiments 1-90 or a pharmaceutical composition as defined in any one of embodiments 90-93 to an individual in need thereof in an amount sufficient to protect neurons or nerve tissue from damage, thereby promoting neuroprotection.

105. A method of treating a cancer, the method comprising administering an EphA4 receptor antagonist as defined in any one of embodiments 1-90 or a pharmaceutical composition as defined in any one of embodiments 90-93 to an individual in need thereof, wherein administration reduces one or more symptoms associated with the cancer.

106. The method according to embodiment 105, wherein the cancer comprises a condition, where a pathophysiology effect is due to dysregulation of EphA4 signaling in a manner that causes EphA4 signaling hyperactivity in cells or spatially or temporally aberrant EphA4 signaling.

106. The method according to embodiment 105 or embodiment 106, wherein the cancer is a glioblastoma, a gastric cancer, a pancreatic cancer, a prostate cancer, a breast cancer, a liver cancer, a leukemia or a Sezary syndrome.

107. Use of an EphA4 receptor antagonist as defined in any one of embodiments 1-90 in the manufacture of a medicament for treating an EphA4-based disease, disorder or pathology.

108. Use of an EphA4 receptor antagonist as defined in any one of embodiments 1-90 or a pharmaceutical composition as defined in any one of embodiments 90-93 in the treatment of an EphA4-based disease, disorder or pathology.

109. The use according to embodiment 107 or embodiment 108, wherein the EphA4-based disease, disorder or pathology comprises a condition, a disease, a disorder and/or pathology where a pathophysiology effect is due to dysregulation of EphA4 signaling in a manner that causes EphA4 signaling hyperactivity in cells or spatially or temporally aberrant EphA4 signaling.

110. The use according to any one of embodiments 107-109, wherein the EphA4-based disease, disorder or pathology is a neurodegenerative disease, a hearing loss, a promotion of nerve regeneration, a promotion of neuroprotection, or a cancer.

111. Use of an EphA4 receptor antagonist as defined in any one of embodiments 1-90 in the manufacture of a medicament for treating a neurodegenerative disease.

112. Use of an EphA4 receptor antagonist as defined in any one of embodiments 1-90 or a pharmaceutical composition as defined in any one of embodiments 90-93 in the treatment of a neurodegenerative disease.

113. The use according to embodiment 111 or embodiment 112, wherein the neurodegenerative disease is an Alexander disease, an Alper's disease, Alzheimer's disease, an amyotrophic lateral sclerosis, an ataxia telangiectasia, a Canavan disease, a Cockayne syndrome, a corticobasal degeneration, a Creutzfeldt-Jakob disease, a Guillain-Barre Syndrome a HIV-induced neurodegeneration, a Huntington disease, a Kennedy's disease, a Krabbe disease, a Lewy body dementia, a Machado-Joseph disease, a multiple sclerosis, a Parkinson's disease, a Pelizaeus-Merzbacher disease, a Pick's disease, a primary lateral sclerosis, a Refsum's disease, a Sandhoff disease, a Schilder's disease, a spinal cord injury, a Steele-Richardson-Olszewski disease, a stroke, a tabes dorsalis and/or a traumatic brain injury.

114. Use of an EphA4 receptor antagonist as defined in any one of embodiments 1-90 in the manufacture of a medicament for treating a hearing loss.

115. Use of an EphA4 receptor antagonist as defined in any one of embodiments 1-90 or a pharmaceutical composition as defined in any one of embodiments 90-93 in the treatment of a hearing loss.

116. The use according to embodiment 114 or embodiment 115, wherein the medicament, the EphA4 receptor antagonist, or the pharmaceutical composition promotes generation of new cochlear sensory hair cells.

117. Use of an EphA4 receptor antagonist as defined in any one of embodiments 1-90 in the manufacture of a medicament for promoting nerve regeneration.

118. Use of an EphA4 receptor antagonist as defined in any one of embodiments 1-90 or a pharmaceutical composition as defined in any one of embodiments 90-93 in the promotion of nerve regeneration.

119. Use of an EphA4 receptor antagonist as defined in any one of embodiments 1-90 in the manufacture of a medicament for promoting neuroprotection.

120. Use of an EphA4 receptor antagonist as defined in any one of embodiments 1-90 or a pharmaceutical composition as defined in any one of embodiments 90-93 in the promotion of neuroprotection.

121. Use of an EphA4 receptor antagonist as defined in any one of embodiments 1-90 in the manufacture of a medicament for treating cancer.

122. Use of an EphA4 receptor antagonist as defined in any one of embodiments 1-90 or a pharmaceutical composition as defined in any one of embodiments 90-93 in the treatment of cancer.

123. The method according to embodiment 121 or embodiment 122, wherein the cancer comprises a condition where a pathophysiology effect is due to dysregulation of EphA4 signaling in a manner that causes EphA4 signaling hyperactivity in cells or spatially or temporally aberrant EphA4 signaling.

124. The method according to any one of embodiments 121-123, wherein the cancer is a glioblastoma, a gastric cancer, a pancreatic cancer, a prostate cancer, a breast cancer, a liver cancer, a leukemia or a Sezary syndrome.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods or uses of treating a disorder disclosed herein.

Example 1

Synthesis of APY Cyclic Peptides

APY cyclic peptides with a free amine at the N terminus and either an amidated C terminus or a free carboxylic acid at the C terminus were obtained from a commercial vendor (GenScript). Peptide amides were synthesized using manual synthetic cycles for 9-fluorenylmethoxycarbonyl (Fmoc) solid phase peptide synthesis. Typically syntheses were performed on a 0.2 mmol scale using Rink amide resin (0.69 mmol/g, Novabiochem). Couplings were performed for 20 minutes using Fmoc protected amino acids (1.1 mmol) dissolved in 2.5 mL 0.4 M HCTU (1.0 mmol) and DIEA (261 µL, 1.5 mmol). Fmoc deprotection was facilitated by treating with an excess of 20% 4-Me piperidine for a total of 7 min. Peptides were deprotected and cleaved from resin using TFA:TIS:EDT:H20 (92.5:2.5:2.5:2.5) while agitating for 2 hours at room temperature. The TFA was 80% evaporated under $N_2$, precipitated using ice-cold diethyl ether, filtered and further washed with cold ether. The crude peptides were dissolved in 45% acetonitrile/water, 0.05% TFA and lyophilized. Samples were solubilized with 20% acetic acid prior to analysis by reversed-phase high-performance liquid chromatography (HPLC) and electrospray ionization mass spectrometry. If the sample was sufficiently homogeneous, it was oxidatively folded in 0.1 M $NH_4HCO_3$ (pH 8) at a peptide concentration of 0.1 mg/mL followed by HPLC purification. If significant synthetic byproducts were present, the peptide was purified by HPLC prior to oxidation. The identity and purity of the peptides (>95%) were verified by reversed-phase HPLC and electrospray ionization mass spectrometry. For further analysis, peptides were dissolved in DMSO or water at a concentration of about 10 mM and the concentration was verified by measuring the optical density at 280 nm.

Example 2

Crystal Structure of APY Cyclic Peptide in Complex with EphA4

While the EphA4 ligand-binding domain has been crystallized in its unbound form and in complex with ephrin ligands, complexes containing peptides and small molecules that target the ephrin-binding pocket of EphA4 have evaded structural evaluation.

The EphA4 ligand binding domain (residues 29-204 with Cys204 replaced by Ala) was cloned into the pETNKI-His-3C-LIC expression vector and expressed in *E. coli* origami 2(DE3) bacterial cells grown at 20° C. overnight. Cells were lysed by sonication and the EphA4 ligand binding domain was purified by Ni$^{2+}$-affinity chromatography. The N-terminal His-tag was cleaved with 3C protease (leaving the 3 extra GPG residues at the EphA4 N terminus) and removed by gel filtration using a Superdex 200 column equilibrated in 100 mM NaCl, 10 mM Hepes (pH 7.9). Protein aliquots were flash frozen in liquid nitrogen and stored at −80° C.

For crystallization, the EphA4 ligand-binding domain was added to a 1.5 fold molar excess of peptide. Crystallization trials were conducted using the sitting-drop vapor diffusion method with commercial screens. Single diffraction quality crystals were obtained after a second round of screening using the Additive Screen HT (Hampton Research) in 0.2 M MgCl$_2$, 0.1 M TrisHCl (pH 8.5), 25% PEG3350 with the additives 4% 1,3-butanediol for APY or 3% 1,6-hexanediol for APY-βAla8.am. Crystals were cryoprotected in reservoir solution with the addition of 20% glycerol and cryocooled in a nitrogen stream at 100 K. Datasets were collected on a rotating anode X-ray generator (Rigaku) at 100 K and processed in iMosflm and with software from the CCP4 suite. Initial analysis suggested space group P222$_1$, but multiple tests suggested crystal twinning and finally P2$_1$ was determined as the real space group. Initial phases were obtained via molecular replacement using coordinates from PDB 2WO1 chain B[36] as search model. Non-crystallographic symmetry (NCS) restraints were used in early rounds of refinement, whereas later refinement stages included TLS (translation/libration/screw) and twin refinement (twin fractions: about 0.35/0.65 for both structures). MolProbity was used for structure validation. Data collection and refinement statistics are summarized in Supplementary Table 1.

After extensive screening of crystallization conditions, crystals of the APY-EphA4 ligand-binding domain complex were successfully generated and the crystal structure solved at a resolution of 2.4 Å (Table 1). The structure contains four APY-EphA4 complexes in the asymmetric unit and provides detailed information on the APY-EphA4 interaction. The APY cyclic peptide efficiently utilizes about 70% (600 Å$^2$) of the available surface within the ephrin-binding pocket (FIG. 1A, 1B). Comparison of the structure of the EphA4 ligand binding domain bound to APY with structures not bound to a ligand (PDB entries 3CKH, 2W01, 4BK4, and 4M4P) or bound to ephrins (FIG. 1B, 1D, 1F) reveals that the APY cyclic peptide induces conformational changes in critical loops of EphA4. Upon peptide binding, it locks the DE and JK loops in highly structured anti parallel β-sheet conformations, which causes the ephrin-binding pocket to adopt a "closed" conformation (compare FIG. 1B with FIG. 1D, 1F), counteracting the reported extraordinary structural flexibility of the EphA4 ligand binding domain. This structural rearrangement indicates that the APY cyclic peptide not only functions as a competitive inhibitor that sterically precludes ephrin ligand binding to EphA4, but also promotes a conformation of the EphA4 ligand binding domain that would be unsuitable for ephrin binding (FIG. 1B). Binding of APY to the EphA4 ligand binding domain should also inhibit the receptor clustering interactions that have been proposed to facilitate ephrin-induced activation. Thus, the structure of the APY-EphA4 complex indicates that the APY cyclic peptide can effectively inhibit EphA4 signaling through multiple concerted mechanisms.

The structure also reveals a critical role for Gly8 in the APY cyclic peptide. This Gly resides at the apex of the

TABLE 1

| Data Collection and Refinement Statistics | | |
|---|---|---|
| | APY-EphA4 | APY-βAla8.am-EphA4 |
| Crystal | | |
| Space Group | P2$_1$ | P2$_1$ |
| Cell dimensions a, b, c (Å) | 36.27, 127.7, 84.57 | 37.22, 127.2, 84.6 |
| Cell dimensions A, β, γ (°) | 90, 90, 90 | 90, 90, 90 |
| Data processing statistics | | |
| Resolution (Å) | 50.95-2.42 (2.52-2.42) | 50.83-2.41 (2.51-2.41) |
| R$_{merge}$ | 0.073 (0.219) | 0.061 (0.207) |
| Reflections | 179142 (18172) | 99518 (27979} |
| Unique reflections | 27280 (2882) | 9181 (27766) |
| I/σI | 14.4 (4.9) | 13.1 (4.8) |
| CC1/2 | 0.995 (0.971) | 0 .996 (0.935} |
| Completeness (%) | 93.4 (90.1) | 92.3 (80.6) |
| Redundancy | 6.6 (6.3) | 3.6 (3.3) |
| Model | | |
| Peptide-EphA4 complexes per asymmetric unit | 4 | 4 |
| No. atoms: Peptide/EphA4 | 388/5703 | 392/5670 |
| No. atoms: Water | 176 | 150 |
| No. atoms: Other solvent | 60 | 140 |
| Refinement statistics | | |
| Resolution (Å) | 50.95-2.42 (2.48-2.42) | 40.14-2.41 (2.47-2.41) |
| Reflections | 25901 (1765) | 26512 (1676) |
| R$_{work}$/R$_{free}$ | 0.1706/0.2325 (0.301/0.423) | 0.1731/0.2405 (0.199/0.261) |
| R.m.s. deviation: Bond lengths (Å) | 0.011 | 0.0095 |
| R.m.s. deviation: Bond angles (Å) | 1.468 | 1.416 |
| Ramachandran favored (%)* | 91.8 | 93.1 |
| Ramachandran allowed (%)* | 7.9 | 6.8 |
| MolProbity Score/Percentile* | 2.25/84$^{th}$ | 1.86/96$^{th}$ |

Figure 2:
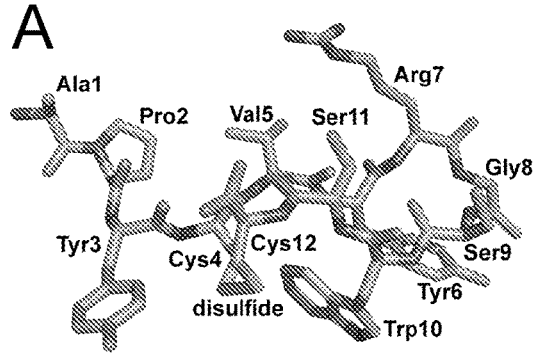
FIG. 2A shows a detailed view of the structure of APY shown in stick representation in orange with oxygens in red, nitrogens in blue and disulfide bond in yellow.
FIG. 2B shows a detailed view of the three intramolecular hydrogen bonds of APY (dotted green lines, with distance in Å shown in black)
FIG. 2C shows a detailed view of APY within the ephrin-binding pocket of EphA4 with the hydrophobic residues interacting with EphA4 shown as spheres and EphA4 shown in surface representation in grey with the DE, GH and JK loops in darker shades of grey.
FIG. 2D shows a detailed view of five hydrogen bonds (dotted green lines, with distances in Å shown in black) between residues in APY (orange) and EphA4 (grey), with only EphA4 residues engaged in hydrogen bonds are shown.
FIG. 2E shows a detailed view of the hydrogen bonds (dotted green lines, with distances in Å shown in black) between $Tyr6_{APY}$ and $Gln71_{EphA4}$ and between $Gln71_{EphA4}$ and $Thr69_{EphA4}$.
Figure 2:
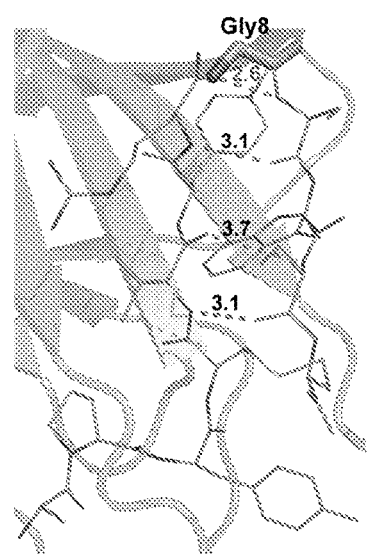
Figure 2:
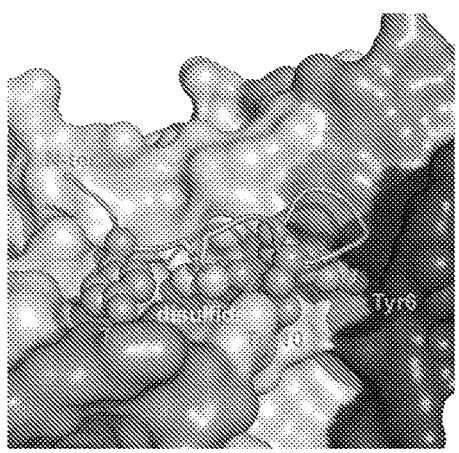
Figure 2:
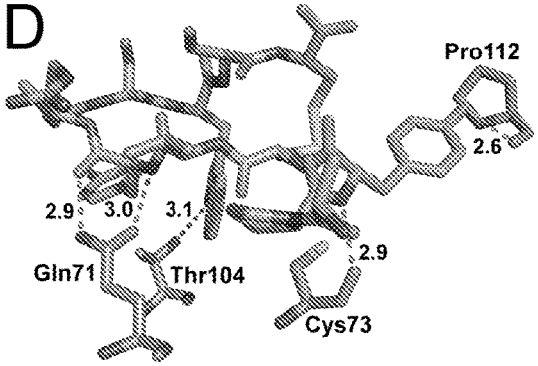
Figure 2:
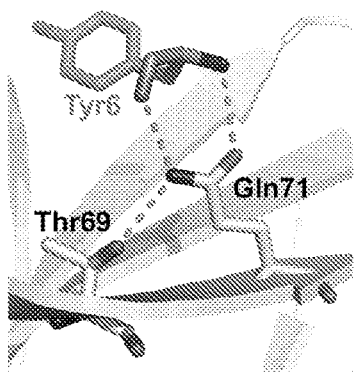

*The βAla residue was omitted from the analysis.

circular portion of the peptide (FIGS. 2A, 2B), with torsion angles in the Ramachandran plot (φ=115.9°; ψ=−17.6° for molecule A) that are only compatible with Gly among the natural amino acids. This enables formation of a "class 1, three-residue β-hairpin" structure that is essential for the correct alignment of the APY residues interacting with EphA4, The β-turn around Gly8 (FIG. 2B, indicated with thicker sticks) shows high strain, as indicated by the short unfavorable N-N distance between the Gly and Ser9 (FIG. 2B, dotted green lime, with distance in Å shown in red). Residues on one side of the peptide, including Tyr3, Tyr6, Trp10 and the disulfide bond, engage in hydrophobic interactions with the ephrin-binding pocket while the opposite side of the bound peptide remains mostly exposed to the solvent (FIG. 2C). APY forms five hydrogen bonds with the EphA4 ligand binding domain (between the backbone NH of $Tyr3_{APY}$ and backbone carbonyl of $Cys73_{EphA4}$; the side chain hydroxyl of $Tyr3_{APY}$ and backbone carbonyl of $Pro112_{EphA4}$; the backbone NH of $Tyr6_{APY}$ and side chain carbonyl of $Gln71_{EphA4}$; the backbone carbonyl of $Tyr6_{APY}$ and side chain NH of $Gln71_{EphA4}$; and the side chain NH of $Trp10_{APY}$ and side chain hydroxyl of $Thr104_{EphA4}$ (FIG. 2D), In addition, the side chain of $Gln71_{EphA4}$ is positioned by a hydrogen bond with the side chain of neighboring $Thr69_{EphA4}$ (FIG. 2E), in agreement with the loss of APY binding when $Thr69_{EphA4}$ is replaced by Ala. The I59A and A193S mutations have also been shown to abolish APY binding, and the structure shows that both of these EphA4 residues also participate in hydrophobic interactions with the peptide. In contrast, replacement of $Thr104_{EphA4}$ with Ala did not decrease APY binding, suggesting that the Ala may compensate for the loss of the hydrogen bond by contributing to the hydrophobic patch that accommodates $Tyr6_{APY}$ and $Trp10_{APY}$.

Besides the interactions with EphA4, three intramolecular hydrogen bonds stabilize the β-hairpin conformation of the peptide (between the backbone NH of Val5 and backbone carbonyl of Ser11; the backbone carbonyl of Val5 and backbone NH of Ser11; and the backbone NH of Arg7 and backbone carbonyl of Ser9 (FIG. 2D). Additional peptide stabilization is provided by an aromatic stack involving $Tyr6_{APY}$ and $Trp10_{APY}$, which packs against the disulfide bond (FIG. 2B). In summary, the crystal structure demonstrates that the APY peptide is an EphA4 competitive antagonist that also induces allosteric effects, with its cyclic scaffold representing an ideal solution for occupying the dynamic ephrin-binding pocket of EphA4.

Example 3

Structure-Guided Optimization of APY Cyclic Peptide Antagonists

Given the key role of the β-hairpin structure of APY bound to EphA4, and the fact that the Gly8 at its apex is the only natural amino acid that can allow formation of this structure, substitution of Gly8 with several unnatural amino acids was explored to determine whether these substitutions might allow for better positioning of the peptide for EphA4 binding while preserving the β-turn structure. In addition, amidation of the APY C-terminus (Cys12) was evaluated to determine whether the formation of an additional hydrogen bond with the backbone carbonyl of $Tyr3_{APY}$, further stabilized the conformation of the peptide. Thus, C-terminally amidated peptides were generated and measured their ability to inhibit ephrin-A5 binding to EphA4 in ELISAs.

To determine peptide $IC_{50}$ values for inhibition of EphA4-ephrin-A5 binding, protein A coated 96-well plates (Pierce/Thermo Scientific) were incubated with 1 μg/mL EphA4 Fc in 80 μl/well TBST (50 mM Tris HCl, 150 mM NaCl (pH 7.5) containing 0.01% Tween-20) for 1 hour at room temperature. The wells were washed 3 times with TBST and incubated for 1.5 hours at room temperature with 0.05 nM ephrin-A5 alkaline phosphatase (AP) and different concentrations of peptides in 40 μl/well TBST. The wells were then washed and bound ephrin-A5 AP was quantified by adding 1 mg/mL p-nitrophenylphosphate substrate (Pierce/Thermo-Scientific) diluted in SEAP buffer (105 mM diethanolamine, 0.5 mM $MgCl_2$, pH 9.8). $OD_{405}$ was measured and the absorbance from wells coated with Fc was subtracted as background.

Figure 3:
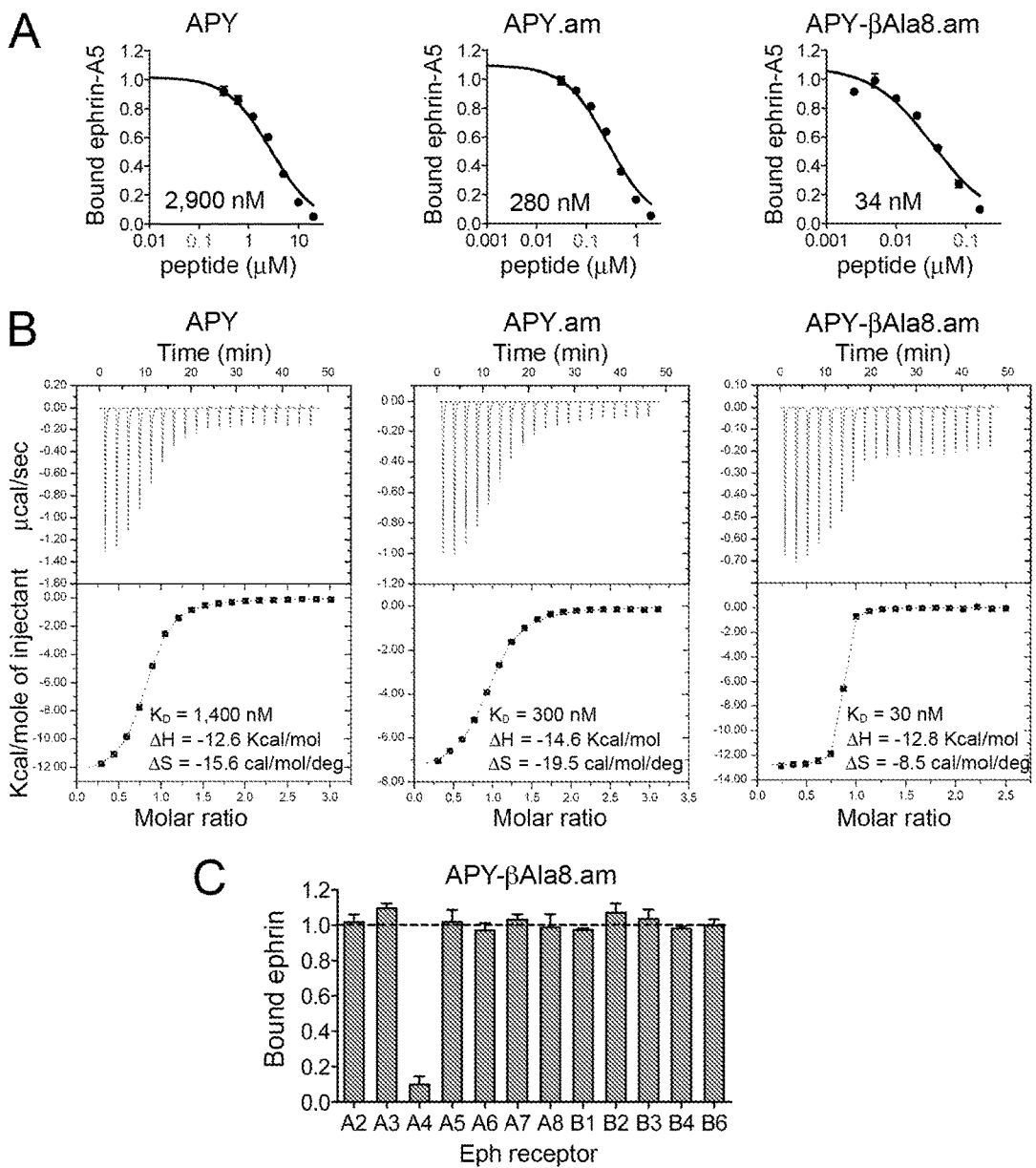
FIG. 3A shows competitive inhibition curves showing inhibition of ephrin-A5 AP binding to immobilized EphA4 Fc by APY in ELISAs, with the 0.1 μM peptide concentration is indicated in red.
FIG. 3B shows isothermal titration calorimetry profiles for peptide binding to EphA4 (upper part of each panel) and plots of the integrated values for the reaction heats [after blank subtraction and normalization to the amount of injected peptide) versus EphA4/peptide molar ratio (lower part of each panel)
FIG. 3C shows Eph receptor selectivity for APY-βAla8.am.

As expected, the C-terminal amidation (leading to APY.am) increased the antagonistic potency of APY (about 10-fold), while replacements of Gly8 had variable effects (FIG. 3A; Table 1). DAla8 did not substantially affect potency, consistent with the fact that D amino acids allow formation of the β-turn. In contrast, replacement of Gly8 with LAla8 carried out for comparison resulted in an about 30-fold loss in potency, confirming the importance of the β-turn conformation. Further constraint of residue 8 through substitution with the achiral aminoisobutyric acid (Aib8) reduced potency by over 10-fold, possibly because of the additional methyl group, which could interfere with EphA4 binding.

A critical observation was that the APY backbone structure appears to be slightly strained. For example, the hydrogen bonds are slightly longer than the ideal 2.9 Å length (FIG. 2B). In addition, the conformation of the β-turn brings the amide groups of Gly8 and Ser9 into close proximity (2.6 Å), likely leading to electrostatic repulsion. To release the strain of the tight 3-residue β-turn at the apex of the peptide, we inserted a methylene spacer into the backbone by replacing Gly8 with βAla (3-aminopropanoic acid). Remarkably, this increased the antagonistic potency of APY.am by about 8-fold, corresponding to an $IC_{50}$ of about 30 nM for APY-βAla8.am (about 85-fold improvement over the original APY cyclic peptide (FIG. 3A; Table 2).

TABLE 2

Potency and Affinity of APY Cyclic Peptides as EphA4 Antagonists

| Peptide | SEQ ID NO: | $IC_{50}$ ± SE (n)$^a$ by ELISA (nM) | $K_D$ by ITC (nM) | Selectivity (μM) |
|---|---|---|---|---|
| APY | 2 | 2,900 ± 300 (9) | 1,400 | >15-fold |
| APY.am | 27 | 280 ± 20 (3) | 300 | nd |
| ac.PY.am | 28 | >10,000 (3) | nd | nd |
| DAla1-PY.am | 29 | 1,100 ± 249 (3) | nd | nd |
| βAla1-PY.am | 30 | 680 ± 130 (3) | nd | nd |

TABLE 2-continued

Potency and Affinity of APY Cyclic Peptides as EphA4 Antagonists

| Peptide | SEQ ID NO: | $IC_{50} \pm SE$ (n)$^a$ by ELISA (nM) | $K_D$ by ITC (nM) | Selectivity (μM) |
|---|---|---|---|---|
| APY-Ala8.am | 31 | 7,700 ± 400 (3) | 2,500 | nd |
| APY-Aib8.am | 32 | 2,600 ± 200 (3) | nd$^b$ | nd |
| APY-DAla8.am | 33 | 280 ± 30 (3) | 250 | nd |
| APY-βAla8.am | 34 | 34 ± 3 (13) | 30 | >120-fold |
| ac.APY-βAla8.am | 35 | 920 ± 60 (3) | nd | nd |
| ALY-βAla8.am | 36 | 62 ± 13 (4) | nd | nd |
| PY-βAla8.am | 37 | 48 ± 9 (6) | nd | nd |
| ac.PY-βAla8.am | 38 | 537 ± 101 (3) | nd | nd |
| KY-βAla8.am | 39 | 260 ± 58 (6) | nd | nd |
| ac.KY-βAla8.am | 40 | 1,161 ± 301 (5) | nd | nd |
| HY-βAla8.am | 41 | 596 ± 127 (3) | nd | nd |
| Y-βAla8.am | 42 | 1,472 ± 342 (4) | nd | nd |
| Ahx1-Y-βAla8.am | 119 | 83 ± 16 (6) | nd | nd |
| Ava1-Y-βAla8.am | 120 | 67 ± 6 (6) | nd | nd |
| γAbu1-Y-βAla8.am | 121 | nd | nd | nd |
| βAla1-Y-βAla8.am | 122 | nd | nd | nd |
| Gly1Y-βAla8.am | 123 | nd | nd | nd |
| Sar1-Y-βAla8.am | 124 | nd | nd | nd |

$^a$n = number of experiments
$^b$nd = not determined
βAla = β-Alanine,
DAla = D-Alanine;
Ahx = Aminohexanoic acid;
Ava = aminopentanoic acid (Valeric acid);
γAbu = γ-aminobutyric acid;
Sar = Sarcosine (N-methylglycine).

Acetylation of the amino-terminal end of APY cyclic peptides appeared to decrease binding affinity for EphA4 (Table 2). For example, acetylation of APY-βAla8.am resulted in an about 30-fold reduction in binding affinity for EphA4. Similar results were obtained with other APY cyclic peptides tested (Table 2).

Complementary determination of dissociation constant ($K_D$) values for peptide binding to the EphA4 ligand binding domain was confirmed using isothermal titration calorimetry (ITC). The EphA4 ligand binding domain and APY cyclic peptides were diluted to obtain a final buffer containing 5% DMSO in 10 mM Hepes (pH 7.6) and 100 mM NaCl. Isothermal Titration calorimetry (ITC) experiments were carried out using an ITC200 calorimeter (Microcal). Two μl aliquots of a 1 mM peptide solution were injected into the cell containing 205 μL EphA4 ligand-binding domain solution at a concentration of 65-95 μM. Experimental data were analyzed using the Origin software package (Microcal). The ITC analysis confirmed that C-terminal amidation and replacement of Gly8 with βAla increase binding affinity, with a $K_D$ of 35 nM for APY-βAla8.am (Table 2). This improvement in affinity makes APY-βAla8.am the most potent EphA4 antagonist developed to date (FIG. 3B).

To assess the Eph receptor selectivity of APY-βAla.am, Eph receptor Fc fusion proteins were immobilized at 1 μg/mL on protein A-coated wells and incubated with 0.05 nM ephrin-A5 AP (for EphA receptors) or ephrin-B2 AP (for Eph B receptors) in the presence or in the absence of the peptide. Ephrin-A5 AP and ephrin-B2 AP for the ELISAs were produced in transiently transfected HEK293T cells according to the method disclosed in Lamberto, et al., *Distinctive Binding of Three Antagonistic Peptides to the Ephrin-Binding Pocket of the EphA4 Receptor*, Biochem J. 445: 47-56 (2012), which is hereby incorporated by reference in its entirety. Bound ephrin-A5 values are normalized to that for bound ephrin-A5 in the absence of peptide and $IC_{50}$ values are indicated under each curve. Importantly, despite the increased binding affinity, the peptide remains highly selective for EphA4. ELISA measuring inhibition of ephrin-A5 AP binding to immobilized EphA Fc receptors and ephrin-B2 AP binding to EphB Fc receptors shows that 3.7 μM APY-βAla8.am selectively inhibits ephrin binding to EphA4 (FIG. 3C). In addition APY-βAla8.am does not inhibit other Eph receptors when used at a concentration of about 100-fold higher than the $IC_{50}$ value for EphA4 (FIG. 3C).

Example 4

Crystal Structure of APY-βAla8.am in Complex with EphA4

Figure 4:
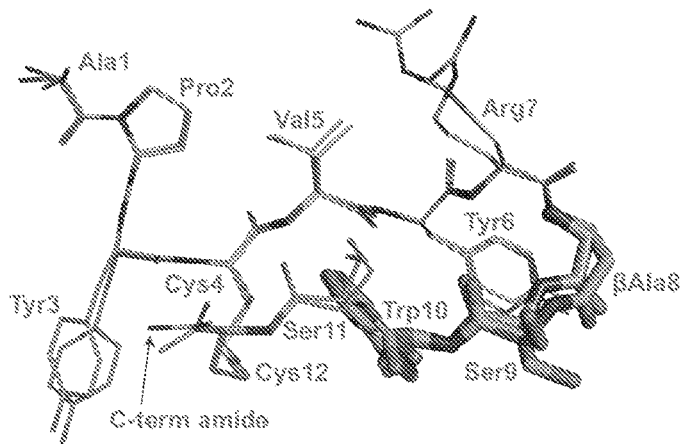
FIG. 4A shows a crystal structure overlay of APY-βAla8.am (green) and APY (orange) revealing marked differences in the β-turn region, particular in the βAla8, Ser9 and Trp10 residues (highlighted by stick representation), with residues labeled for the APY-βAla8.am peptide.
FIG. 4B shows intramolecular hydrogen bonds of APY-βAla8.am.
Figure 4:
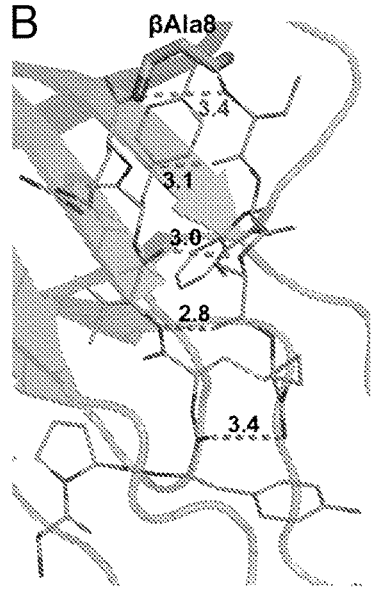

To better understand the molecular details underlying the dramatic increase in potency of APY-βAla8.am further crystallization analysis was performed. The crystallization conditions used for the APY-EphA4 complex yielded initial crystals that were further refined to obtain diffracting crystals that enabled us to solve the structure of APY-βAla8.am-EphA4 complex at a resolution of 2.4 A. (Table 1). Comparison of bound APY-βAla8.am with APY revealed a very similar overall conformation (FIG. 4A). However, overall intramolecular hydrogen bond patterns and conformations are more favorable for APY-βAla8.am than for APY peptide, including the presence of an additional hydrogen bond between the C-terminal amide and Tyr3 of APY-βAla8.am. For example, an additional hydrogen bond links the amidated C terminus of APY-βAla8.am with the backbone carbonyl function of Tyr3 leads to an overall stabilization of the peptide and improved interaction with EphA4 (FIG. 4B). Furthermore, comparison of the four APY-βAla8.am-EphA4 complexes in the crystal asymmetric unit with their counterparts in the APY-EphA4 structure revealed additional features consistent with the optimized binding of APY-βAla8.am. These include a less strained β-turn due to a longer distance between the backbone NH of βAla8 and Ser9 in APY-βAla8.am compared to the corresponding distance between Gly8 and Ser9 in APY (Table 3). Additionally, the intrapeptide hydrogen bond distances are less variable and more favorable in the four APY-βAla8.am molecules than in the APY molecules (Table 3). This is reflected in the increased enthalpic contribution to APY-EphA4 complex formation in ITC experiments (FIG. 3B).

TABLE 3

Peptide hydrogen bond and β-turn N—N distances (Å)

| Bond | APY | | | | APY-βAla8.am | | | |
|---|---|---|---|---|---|---|---|---|
| | A | B | C | D | A | B | C | D |
| Gly8/βAla8 N - Ser9 N | 2.6 | 2.7 | 2.6 | 2.6 | 3.4 | 3.0 | 3.3 | 3.1 |
| Arg7 N - Ser9 O | 3.1 | 3.1 | 3.1 | 3.0 | 3.1 | 2.9 | 3.0 | 2.9 |
| Val5 O - Ser11 N | 3.7 | 2.9 | 3.3 | 3.0 | 3.0 | 3.0 | 3.1 | 3.0 |
| Val5 N - Ser11 O | 3.1 | 3.0 | 3.7 | 3.2 | 2.8 | 3.2 | 3.2 | 3.1 |
| Tyr3 O - C-term N | — | — | — | — | 3.4 | 3.0 | 3.1 | 3.6 |

Example 5

Secondary Phage Display Screens Reveal APY Features Important for EphA4 Binding

To further characterize the role of different APY residues, four secondary phage display libraries were constructed that retained Cys4 and Cys12 (essential for the cyclic conformation of APY) and Gly8 (essential for the β-turn) but had variable residues at several other positions (Table 4).

TABLE 4

Phage Display Libraries

| Name | Sequence | SEQ ID NO: |
|---|---|---|
| APY peptide | APYCVYRGSWSC | 2 |
| Library 1 | APXCVXRGSWSC | 111 |
| Library 2 | [AP(Y/F)CX(Y/F/W/L/C)XGXXXC] | 112 |
| Library 3 | APYCVYXGXWXC | 113 |
| Library 4 | XXXCVYRGSWSC | 114 |

X, is any amino acid.

The secondary phage display libraries were generated by using PAGE-purified oligonucleotides and the M13KE gIII cloning vector according to the recommendations of the manufacturer (New England BioLabs). The following primers were used to generate the libraries: library 1 SEQ ID NO: 115; library 2 SEQ ID NO: 116; library 3 SEQ ID NO: 117; library 4 SEQ ID NO: 118. The libraries were panned on mouse EphA4 ectodomain fused to Fc (EphA4 Fc; R&D Systems) immobilized at 10 μg/mL in Tris-buffered saline (TBS; 50 mM TrisHCl, 150 mM NaCl, pH 7.5) in a protein G-coated well. A well without EphA4 Fc was used as a negative control. Wells were blocked for 1 hour at room temperature with 0.5% milk in TBS and washed in washing buffer (TBS containing 0.5% Tween-20) prior to incubation with phage libraries ($10^7$-$10^8$ plaque forming units) diluted in 100 μl TBS containing 0.1% Tween-20 for 1 hour at room temperature. Unbound phage were washed away with washing buffer and bound phage were eluted with 0.2 M glycine HCl (pH 2.2) for 10 min. The eluates were immediately neutralized with 1 M TrisHCl (pH 9.1).

To measure the titer of the eluted phage, E. coli ER2738 cells grown to about 0.6 $OD_{600}$ in LB containing 10 μg/mL tetracycline were infected for 5 min with different dilutions of the phage eluted from wells coated with EphA4 Fc or from control wells, according to the manufacturer's recommendations (New England BioLabs). Plaques from plates enriched in EphA4-binding phage were amplified according to the manufacturer's recommendations (New England BioLabs) and tested in ELISAs for EphA4 binding. Phage DNA was purified according to the recommendations of the manufacturer (New England BioLabs) and sequenced.

To measure phage binding to EphA4, Ni-NTA HisSorb Strips (Qiagen) were incubated for 1 hour in TBS with 1 μg/mL EphA4 Fc, which has a hexahistidine C-terminal tag, or only with TBS as a control. Wells were then blocked with 0.5% milk diluted in TBS for 1 hour and washed in washing buffer before incubation for 1 hour at room temperature with a 1:200 dilution of phage amplified from a single plaque. Wells were then washed before addition of horseradish peroxidase (HRP)-conjugated α-M13 antibody (GE Healthcare; #27-9421-01). Phage binding was detected with the ABTS substrate dissolved in 50 mM citric acid (pH 4.0). $OD_{405}$ was measured and the absorbance from wells without EphA4 Fc was subtracted as background.

To compare the strength of EphA4 binding of different phage clones, Ni-NT A HisSorb Strips were coated with EphA4 Fc or Fc (Fisher Scientific) as the background. The wells were incubated for 1 hour with a phage concentration corresponding to 1 $OD_{280}$ in 50 μl TBS, 0.1% Tween-20 in the presence of different concentrations of the KYL antagonist peptide or in the absence of KYL. Bound phage was quantified with HRP-conjugated α-M13 antibody.

To investigate whether the critical Tyr3, Tyr6 and Trp10 can be replaced by other amino acids, we isolated EphA4-binding phage from libraries with variable residues at these positions. In line with the peptide-EphA4 structures, sequencing of 22 peptides showed a preference for hydrophobic amino acids at position 3, including Leu (7 peptides), Tyr (5 peptides), Phe/Val (3 peptides each) and Ile/Trp/His (1 peptide each) (Table 5, libraries 1 and 4). To evaluate the approximate relative binding strength of the phage-displayed peptides, KYL peptide antagonist was used to compete phage binding to EphA4 in ELISAs. The results suggest that peptides with Tyr, Phe, Trp, Val, Leu, His and Trp (but not Ile) at position 3 can bind strongly to EphA4 because high KYL concentrations were needed to inhibit phage binding (Table 5, libraries 1 and 4). Moreover, the displayed peptides isolated from libraries with variable positions 6 and/or 10 suggest that only aromatic amino acids are tolerated at position 6 and only Trp at position 10 (Table 5, libraries 1 and 2). This is consistent with the formation of an aromatic stack between the two residues, which is one of the key features of the APY-EphA4 hydrophobic interaction pattern.

TABLE 5

Peptides from Secondary Phage Display Screens

| Library Clone | Number of Clones | Peptide | Phage-EphA4 Binding Inhibition[f] | SEQ ID NO: |
|---|---|---|---|---|
| 1-1 | 1[a] | APYCVWRGSWSC | ++++ | 70 |
| 1-2 | 1 | APVCVWRGSWSC | +++ | 71 |
| 1-3 | 9 | APLCVWRGSWSC | +++ | 72 |

TABLE 5-continued

Peptides from Secondary Phage Display Screens

| Library Clone | Number of Clones | Peptide | Phage-EphA4 Binding Inhibition1[f] | SEQ ID NO: |
|---|---|---|---|---|
| 1-4 | 2[b,c] | APLCVYRGSWSC | +++ | 73 |
| 1-5 | 1 | APICVYRGSWSC | + | 74 |
| 1-6 | 1 | APWCVFRGSWSC | +++ | 75 |
| 1-7 | 1 | APHCVFRGSWSC | +++ | 76 |
| 2-1 | 2 | APYCSYYGQWMC | ++ | 77 |
| 2-2 | 15 | APFCLYTGDWVC | +++ | 78 |
| 2-3 | 6 | APFCSWAGWWTC | + | 79 |
| 3-1 | 1 | APYCVYTGEWLC | ++++ | 80 |
| 3-2 | 2 | APYCVYDGTWIC | +++ | 81 |
| 3-3 | 1 | APYCVYGGTWRC | + | 82 |
| 3-4 | 1 | APYCVYSGTWHC | +++ | 83 |
| 3-5 | 4 | APYCVYNGTWNC | ++++ | 84 |
| 3-6 | 2 | APYCVYDGSWNC | +++ | 85 |
| 3-7 | 2[a] | APYCVYKGSWNC | nd[d] | 86 |
| 3-8 | 1[a] | APYCVYEGLWNC | nd | 87 |
| 3-9 | 1 | APYCVYSGVWNC | ++ | 88 |
| 3-10 | 1 | APYCVYSGWWKC | ++ | 89 |
| 3-11 | 1 | APYCVYSGRWEC | ++ | 90 |
| 3-12 | 1 | APYCVYRGVWEC | ++++ | 91 |
| 3-13 | 1[a] | APYCVYQGLWEC | nd | 92 |
| 3-14 | 1[a] | APYCVYGGLWTC | + | 92 |
| 3-15 | 1[a] | APYCVYAGKWSC | nd | 94 |
| 3-16 | 1 | APYCVYQGYWKC | +++ | 95 |
| 3-17 | 1 | APYCVYNGRWDC | ++ | 96 |
| 3-18 | 1[a] | APYCVYRGHWGC | nd | 97 |
| 3-19 | 1[a] | GPYCVYKGNWWC | ++ | 98 |
| 4-1 | 1 | APYCVYRGSWSC | +++ | 99 |
| 4-2 | 2 | EPYCVYRGSWSC | +++ | 100 |
| 4-3 | 2 | DAYCVYRGSWSC | + | 101 |
| 4-4 | 1 | AAFCVYRGSWSC | + | 102 |
| 4-5 | 1[e] | APLCVYRGSWSC | +++ | 103 |
| 4-6 | 1 | LPLCVYRGSWSC | + | 104 |
| 4-7 | 1 | GPLCVYRGSWSC | ++ | 105 |
| 4-8 | 1 | SALCVYRGSWSC | + | 106 |
| 4-9 | 1 | QALCVYRGSWSC | ++ | 107 |
| 4-10 | 1 | FPVCVYRGSWSC | + | 108 |
| 4-11 | 1 | LPVCVYRGSWSC | + | 109 |
| 4-12 | 1 | YPMCVYRGSWSC | + | 110 |

[a]Not from panning.
[b]Clone with different DNA sequences. The sequence of the APY peptide (isolated from library 4) is boxed.
[c]Same peptide sequence isolated from different libraries.
[d]nd, not determined.
[e]The Ala1 to Gly change was not designed in the library and is thus due to an aberrant oligonucleotide.
[f]The KYL concentration needed to inhibit phage-EphA4 binding.

With regard to the APY N terminus (Ala-Pro), EphA4-binding phage contained a variety of residues at position 1 (Table 4, library 4). At position 2, Pro was most frequent (8/12 peptides) with Ala present in the remaining peptides. However, only phage clones with AlaI/GluI and Pro2 exhibited strong binding to EphA4 (Table 4, library 4). Thus, despite a lack of obviously important contacts in the crystal structure, the identity of all three residues outside the circular portion of APY is important for APY binding activity.

The crystal structures also show that Arg7, Ser9 and Ser1 1 of APY and APY-βAla8.am do not engage in direct interactions with EphA4 residues. Indeed, a wide variety of amino acids can occupy these positions in EphA4-binding phage (Table 4, libraries 2 and 3). Furthermore, approximately half of the phage clones that were randomly chosen from library 3, in which residues 7, 9 and 11 are randomized, bound to EphA4 even though they were not isolated by panning on EphA4. Interestingly, all but one of the non-binding peptides from this library have Pro at one of the randomized positions. Thus, it appears that most amino acids can occupy positions 7, 9 and 11 of the APY scaffold with the exception of Pro, likely due to the disrupting effects of Pro on the conformation of the circular portion of APY. These data indicate that residues forming the solvent-exposed side of APY derivatives bound to EphA4 could be modified without substantial loss of binding affinity, for example for peptide derivatization to improve pharmacokinetic properties.

Example 6

Further Structure-Guided Optimization of APY Cyclic Peptide Antagonists

Based on the findings of the secondary phage display library screens in conjunction with the crystal structure of the original APY cyclic peptide as well as APY-βAla8.am, additional APY cyclic peptides were designed in an effort to increase potency. In addition, because of its susceptibility to cleaved by serum aminopeptidases, Ala 1 was replaced with several different unnatural amino acid in an effort to increase stability. One derivative (APY-d3.am) has the sequence βAPYCVYRβASWSC-am (SEQ ID NO: 47) and has a βAla (3-aminopropanoic acid) replacing both Ala1 and Gly8 and an amidated C terminus. Another derivative (APY-d4.am) has the sequence βAPYCVYRβAEWEC-am (SEQ ID NO: 50) and has a glutamine replacing both Ser9 and Ser1 1 in addition to having a βAla (3-aminopropanoic acid)

replacing both Ala1 and Gly8 and an amidated C terminus. A third derivative (DAla1-PY-βAla8.am) has the sequence D-APYCVYRβASWSC-am (SEQ ID NO: 52) and has a D-Ala replacing Ala1, βAla (3-aminopropanoic acid) replacing Gly8 and an amidated C terminus.

In another set of experiments, the effects of position 7 was evaluated by substituting Arg7 with Lys. One derivative (APY-Lys7-βAla8.am) has the sequence APYCVYKβASWSC-am (SEQ ID NO: 45) and has a Lys replacing Arg7, a βAla (3-aminopropanoic acid) replacing Gly8 and an amidated C terminus. Another derivative (βAla1-PY-Lys7-βAla8.am) has the sequence βAPYCVYKβAEWEC-am (SEQ ID NO: 48) and has a βAla (3-aminopropanoic acid) replacing both Ala1 and Gly8, a Lys replacing Arg7 and an amidated C terminus.

Figure 5:
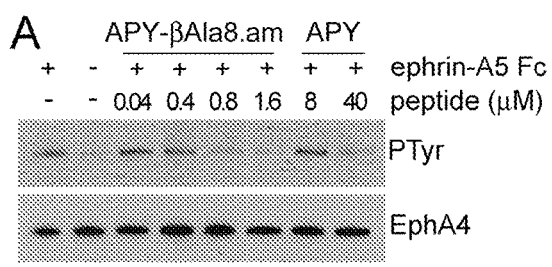
FIG. 5A shows inhibition of ephrin-A5-induced EphA4 tyrosine phosphorylation, with the graph on the right showing quantification of individual EphA4 tyrosine phosphorylation levels from the immunoblots of 2 experiments, normalized to the phosphorylation level in the ephrin-A5/no peptide condition in each experiment.
FIG. 5B shows inhibition of EphA4-dependent growth cone collapse.
FIG. 5C shows that the APY-βAla8.am peptide does not have detectable cytotoxic effects as assessed using the MTT assay.
Figure 5:
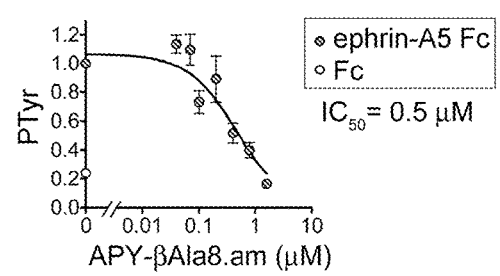
Figure 5:
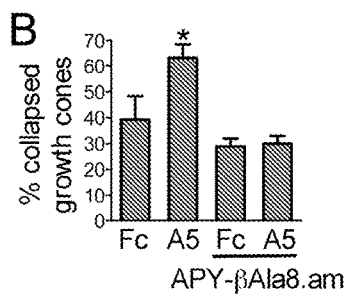
Figure 5:
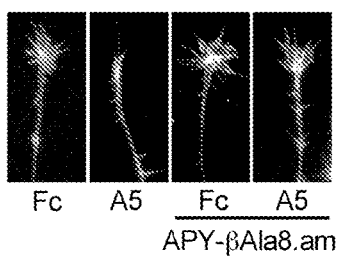
Figure 5:
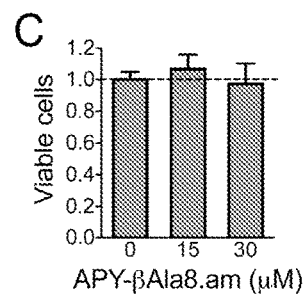

The results indicated that APY-d3 specifically inhibits EphA4-ephrin binding with an $IC_{50}$ value of about 30 nM in ELISA and a $K_D$ measured also about 30 nM by ITC. APY-d4 exhibited a 2-fold better performance over APY-d3, inhibiting EphA4-ephrin binding with an $IC_{50}$ value of about 15 nM in ELISA. All APY cyclic peptides exhibit at least 35-fold more potent than any previously known EphA4 antagonist and at least 50-fold more potent than the original APY cyclic peptide.

that APY-βAla8.am inhibits ephrin-A5-induced EphA4 activation with an $IC_{50}$ value of about 0.3 μM, with almost complete inhibition at 1.6 μM APY-βAla8.am (FIG. 5A). This inhibition is ≥20 fold more potent than KYL or APY (FIG. 5A), Eph4A antagonist peptides previously used in mouse models of nerve regeneration and ALS. Similarly, APY-d3.am also inhibits ephrin-A5-induced EphA4 activation with an $IC_{50}$ value of about 0.24 μM, with almost complete inhibition at 1.0 μM APY-d3.am. This inhibition is ≥50 fold more potent than KYL or APY. These results indicate that APY cyclic peptides disclosed herein are also a potent inhibitor of ephrin-induced EphA4 activation in cells.

Impaired axon sprouting and lack of reinnervation are regarded as part of the pathology underlying neurodegenerative diseases such as ALS, ultimately causing neuronal cell death. Because growth cone collapse is linked to the failure of injured axons to sprout and regenerate, the ability of APY cyclic peptides to inhibit the collapse of neuronal growth cones (enlarged structures at the leading tip of axons) was assessed using used nasal retinal explants, where ephrin-A5-induced collapse depends on EphA4 activation and can be blocked by 5 μM KYL peptide. Explants from embryonic day 6 (E6) chicken nasal retinas were cultured on

TABLE 6

Potency and Affinity of APY Cyclic Peptides as EphA4 Antagonists

| Peptide | SEQ ID NO: | $IC_{50}$ ± SE (n)[a] by ELISA (nM) | $K_D$ by ITC (nM) | Selectivity by ELISA (μM) |
|---|---|---|---|---|
| APY-βAla8.am | 36 | 34 ± 3 (13) | 30 | >120-fold |
| APY-Lys7-βAla8.am | 45 | 68 ± 11 (13) | nd | nd |
| APY-d3.am | 46 | 30 ± 5 (16) | 30 | >300-fold |
| βAla1-PY-Lys7-βAla8.am | 48 | 70 ± 17 (5) | nd | nd |
| APY-d4.am | 50 | 16 ± 2 (4) | nd | >300-fold |
| DAla1-PY-βAla8.am | 52 | 63 ± 13 (6) | 45 | >150-fold |

[a] n = number of experiments

Importantly, despite the increased binding affinity, APY-d3.am, APY-d4.am and APY-DAla1.am remain highly selective for EphA4. ELISA measuring inhibition of ephrin-A5 AP binding to immobilized EphA Fc receptors and ephrin-B2 AP binding to EphB Fc receptors shows that APY-d3.am, APY-d4.am and APY-DAla1.am each selectively inhibits ephrin binding to EphA4 (Table 6). In addition, the APY cyclic peptides disclosed herein do not inhibit other Eph receptors when used at a concentration of about 100-fold higher than the $IC_{50}$ value for EphA4. For example, no appreciable APY cyclic peptide binding was detected for the ephrin receptors EphA2, EphA3, EphA5, EphA6, EphA7, EphA8, EphB1, EphB2, EphB3, EphB4 or EphB6.

Example 7

Submicromolar Amounts of APY Cyclic Peptides Inhibit EphA4 Activation in Cells

To assess the antagonistic potency of APY cyclic peptides disclosed herein in live cells, EphA4 receptor-mediate phosphorylation was determined using a cell culture assay. EphA4 was immunoprecipitated from stably transfected human embryonal kidney (HEK293) cells treated with ephrin-A5 Fc (+) or Fc control (−) in the presence of various concentrations of APY, APY-βAla8.am or APY-d3.am. The immunoprecipitates were probed for phosphotyrosine (PTyr) and reprobed for EphA4. These experiments revealed 35 mm glass-bottom MatTek plates pre-coated overnight with 200 μg/mL poly-D-Lysine in PBS: and then for 3 hours with 20 μg/mL laminin in PBS at 37° C. Explants were cultured overnight in DMEM-F12 containing 0.4% methylcellulose (Sigma-Aldrich), 0.45% glucose, N-2 supplement (Life Technologies), 2 mM L-Glutamine (Life Technologies), 1 mM sodium pyruvate, 0.1% BSA and antibiotics. The culture medium was then replaced with medium without methylcellulose and 3 hours later the retinal explants were incubated with 0.3 μM APY-βAla8.am or 0.15 μM APY-d3.am for 30 min before stimulation with 1 μg/mL preclustered ephrin-A5 Fc or Fc as a control for 30 min in the continued presence of the APY cyclic peptide. Ephrin-A5 Fc was preclustered by incubating it for 30 min on ice with 1/10 polyclonal α-Fc antibody (Jackson Laboratories). The explants were then fixed for 30 min in 3.7% formaldehyde, 4% sucrose in PBS at room temperature, permeabilized for 3 min with 0.1% Triton X-100 in PBS, and filamentous actin was stained with rhodamine-conjugated phalloidin (Life Technologies). Growth cones were photographed under a fluorescence microscope and scored in a blinded manner. A growth cone was scored as collapsed when no lamellipodia or filopodia were present at the tip of the neurite. For APY-βAla8.am, a histogram was generated showing mean percentages of collapsed growth cones (about 70 to 500 per condition in each experiment). Error bars represent standard errors from 3 experiments. *, $P<0.05$ compared to Fc without peptide by one-way ANOVA.

The results indicate that APY-βAla8.am effectively blocked growth cone collapse at a concentration of 0.3 μM (FIG. 5B). This histogram illustrates that control neurites treated only with Fc showed only 40% growth cone collapse while cells treated with Fc and ephrin-A5 exhibited about 65% growth cone collapse, a statistically significance increase in collapse. On the other hand, neurites treated with Fc and APY-βAla8.am showed about 30% growth cone collapse while cells treated with Fc, ephrin-A5, and APY-βAla8.am similarly exhibited only 30% growth cone collapse, a level comparable to the unstimulated neurites. Similarly, APY-d3.am potently inhibits EphA4-dependent neuronal growth cone collapse at a concentration of 0.15 μM. For example, control neurites treated only with Fc showed only 20% growth cone collapse while cells treated with Fc and ephrin-A5 exhibited about 70% growth cone collapse, a statistically significance increase in collapse. On the other hand, neurites treated with Fc and APY-d3.am showed about 30% growth cone collapse while cells treated with Fc, ephrin-A5, and APY-d3.am only exhibited less than 40% growth cone collapse, a level comparable to the unstimulated neurites. The APY cyclic peptides did not detectably affect the morphology of growth cones in the absence of ephrin, consistent with the lack of nonspecific effects or toxicity. These data show that APY cyclic peptides disclosed herein effectively blocked growth cone collapse in the presence of EphA4 receptor signaling.

To evaluate APY cyclic peptide cytotoxicity, MTT (3-(4,5-dimethylthiazol-2-yl)-2,5-diphenyltetrazolium bromide) colorimetric assays were conducted. HT22 mouse hippocampal neurons were grown in DMEM supplemented with 10% FBS, 1 mM sodium pyruvate and antibiotics. Cells were seeded in 96 well plates and incubated for 24 hours with 30 μM APY-βAla8.am or 2.7 μM APY-d3.am (diluted from a stock dissolved in water) or with no peptide as a control. The cells were then incubated for 2 hours in 5 mg/mL MTT (Sigma-Aldrich) in PBS at 37° C. in a $CO_2$ incubator. The resulting formazan crystals were solubilized by addition of 100% DMSO and $OD_{570}$ was measured. This cell viability assay did not reveal significant cytotoxicity in the hippocampal neuron-derived HT22 cell line treated for 24 hours with 30 μM APY-βAla8.am, a concentration about 100-fold higher than that sufficient to inhibit growth cone collapse (FIG. 5C). Similarly, no significant cytotoxicity was observed in hippocampal neuron-derived HT22 cell line treated for 24 hours with 2.7 μM APY-d3.am, a concentration about 100-fold higher than needed to inhibit growth cone collapse. The KYL peptide has been the EphA4 antagonist of choice for promoting neural repair and counteracting neurodegeneration. These data show that APY cyclic peptides disclosed herein are not cytotoxic.

Example 8

Stability of APY Cyclic Peptides in Culture Medium, Plasma and Cerebrospinal Fluid To evaluate the stability of APY cyclic peptides disclosed herein, the ability of these peptides to inhibit EphA4-ephrin-A5 interaction was assessed after different incubation times in mouse plasma or rat cerebrospinal fluid (CSF). In these stability assays, 200 μM of an APY cyclic peptide was incubated at 37° C. in plasma or CSF. Aliquots were collected at different time points and used in ELISA measuring inhibition of EphA4 AP-ephrin-A5 Fc binding. For ELISA, ephrin-A5 Fc was immobilized at 1 μg/mL for 1 hour at room temperature in protein A-coated 96-well plates as described above. Plasma or CSF containing the peptides were incubated in the wells at a 1:20 dilution (corresponding to final concentrations of 10 μM of the APY cyclic peptide in the absence of proteolytic degradation) with 0.05 nM EphA4 AP for 30 minutes at 4° C. These peptide concentrations yield about 80% inhibition of EphA4 AP binding to ephrin-A5 Fc. The amount of bound AP fusion protein was quantified by measuring the absorbance at 280 nm. The optical density obtained from wells coated with Fc and incubated with EphA4 AP and plasma or serum was subtracted as the background. Signals obtained from wells incubated with conditioned plasma or serum not containing an APY cyclic (no peptide) was used to determine the 0% inhibition level (efficacy=0), while signals in the presence of an APY cyclic peptide not incubated in plasma or serum (intact peptide) was used for normalization (efficacy=1).

TABLE 7

| Half-life of APY Cyclic Peptides | | |
|---|---|---|
| Peptide | Half-life ($t_{1/2}$) Plasma | Half-life ($t_{1/2}$) CSF |
| KYL | 11 minutes | nd |
| APY | 16 minutes | nd |
| APY-βAla8.am | 2 hours | 0.5 to 3 hours |
| APY-d3.am | >72 hours | >72 hours |
| DAla1-PY-βAla8.am | >72 hours | >72 hours |

The results indicate that KYL and APY peptides loss their antagonistic activity rapidly, having half-lives of 11 minutes and 16 minutes respectively in mouse serum. APY-βAla8.am showed a 2-8-fold increase in stability, having a half-life of about 2 hours in mouse plasma and about 30 minutes to about 3 hours in rat CSF depending on the conditions. Strikingly, the addition of a non-natural amino acid at position 1 of the APY cyclic peptides disclosed herein significantly increased the half-life of the peptide. For example, APY-d3 and DAla1-PY-βAla8.am both showed a significant increase in stability, having a half-life of about 72 hours in either mouse plasma or rat CSF. These results indicate that the APY cyclic peptide disclosed herein can be modified to significantly increase half-life of its antagonistic activity.

Example 9

Therapeutic Usefulness of APY Cyclic Peptides in ALS

To evaluate the therapeutic effects of APY cyclic peptides disclosed herein on ALS, EphA4 signaling inhibition by APY cyclic peptides was examined using a mouse SOD1*G93A model of ALS. SOD1*G93A transgenic mice express human Cu/Zn superoxide dismutase 1 (SOD1) harboring a single amino acid substitution of glycine to alanine at codon 93. This pathogenic mutation is associated with early-onset familial ALS with hemizygotic SOD1*G93A animals exhibit neuronal degeneration due to progressive accumulation of detergent-resistant SOD-ubiquitin aggregates and aberrant neurofilament accumulations in degenerating motor neurons as well as reactive astroglia and microglia. The neuronal degeneration leads to limb grasping, widespread muscle weakness, atrophy and paralysis in one or more limbs due to loss of motor neurons from the spinal cord due to abnormal axonal transport. Transgenic mice also have an abbreviated life span.

Both SOD1*G93A mice, as well as non-transgenic mice used as age-matched controls, will be administered an APY cyclic peptide, such as APY-βA8.am, APY-d3 or APY-d4, or APY-d3 dimers disclosed herein, into the cerebral ventricles of the brain using a minipump. Behavioral analyses will reveal muscle function of SOD1*G93A mice compared to controls. Muscle and neuromuscular junction pathology of SOD1*G93A mice and controls then will be assayed using standard histological staining and immunohistochemistry using an amyloid beta (Aβ) antibody. These results will show that APY cyclic peptides disclosed herein will delay disease onset and pathogenesis, will decrease motor neuron loss, and/or will extend survival of the mice, thereby demonstrating the therapeutic effects of APY cyclic peptides disclosed herein in inhibiting EphA4 signaling and their usefulness in treating ALS. In addition, these data will confirm the findings obtained with the KYL peptide (a less potent EphA4 peptide antagonist) that inhibition of EphA4 signaling provides therapeutic benefits in Alzheimer's disease.

Example 10

Therapeutic Usefulness of APY Cyclic Peptides in Alzheimer's Disease

To evaluate the therapeutic effects of APY cyclic peptides disclosed herein on Alzheimer's disease, EphA4 signaling inhibition by APY cyclic peptides was examined using an APP/PS1 or other mouse model for Alzheimer's disease, including the TgCRND8 model encoding a double mutant form of amyloid precursor protein 695 (KM670/671NL+ V717F) under the control of the PrP gene promoter. See, e.g., Chrishti, et al., *Early-Onset Amyloid Deposition and Cognitive Deficits in Transgenic Mice Expressing a Double Mutant Form of Amyloid Precursor Protein 695*, J. Biol. Chem 276(24): 21562-21570 (2001), which is hereby incorporated by reference in its entirety. APP/PS1 double transgenic mice express a chimeric mouse/human amyloid precursor protein (Mo/HuAPP695swe) and a mutant human presenilin 1 (PS1-dE9) both directed to CNS neurons. Both pathogenic mutations are associated with early-onset Alzheimer's disease with transgenic mice showing visible β-amyloid plaque deposits in the brains by 6 to 7 months of age resulting in synaptic loss. APP/PS1 mice also exhibit certain behavioral abnormalities such as, impaired reversal learning of a food-rewarded four-arm spatial maze task, cognitive deficits in spatial learning and memory in the Morris water maze, and inhibition of hippocampal CA1 long-term potentiation (LTP). Thus, APP/PS1 mice demonstrate synaptic loss, reduced glutamatergic synaptic transmission and impaired synaptic plasticity in the hippocampus.

Both APP/PS1 mice, as well as non-transgenic mice used as age-matched controls, will be administered an APY cyclic peptide, such as APY-βA8.am, APY-d3 or APY-d4, or APY-d3 dimers disclosed herein, into the brain by intracerebral infusion for about 3 weeks. β-amyloid deposition and neuron loss in the cerebral cortex and hippocampus of APP/PS1 mice and controls then will be assayed using standard histological staining and immunohistochemistry using an amyloid beta (Aβ) antibody. These results will show that APY cyclic peptides disclosed herein will inhibit Aβ toxicity and/or will restore normal synaptic function and/or will restore LTP formation in APPP/PS1 mice, thereby demonstrating the therapeutic effects of APY cyclic peptides disclosed herein in inhibiting EphA4 signaling and their usefulness in treating Alzheimer's disease. In addition, these data will confirm the findings obtained with the KYL peptide (a less potent EphA4 peptide antagonist) that inhibition of EphA4 signaling provides therapeutic benefits in Alzheimer's disease.

Example 11

Therapeutic Usefulness of APY Cyclic Peptides in Stroke

To evaluate the therapeutic effects of APY cyclic peptides disclosed herein on stoke recovery, EphA4 signaling inhibition by APY cyclic peptides was examined using a mouse photothrombosis model for stroke. See, e.g., Lemmens, et al., *Modifying Expression of EphA4 and its Downstream Targets Improves Functional Recovery after Stroke*, Hum. Mol. Genet. 22(11): 2214-2220 (2013), which is hereby incorporated by reference in its entirety. Focal cortical ischemia will be induced by photothrombosis in a wild-type strain of mice aged 3-4 months. Before the induction of photothrombosis, animals will receive training daily for 1 week on an accelerating rotarod treadmill (Ugo Basile), rotating from 4 to 40 r.p.m. over the course of 300 seconds in order to record three motor performance evaluations. The baseline performance will be recorded over six attempts the week after training. Induction of stroke will be evaluated 1 day after the procedure and animals will be excluded if the average and/or maximum performance over three attempts was 75% compared with baseline. Infarct volume will also be calculated using serial coronal sections immune-stained with antibodies against glial fibrillary acidic protein (GFAP) and compared to the contralateral side. Nerve regeneration will be evaluated by immunohistochemistry using antibodies against EphA4 and glial fibrillary acidic protein (GFAP).

Three days after induction of experimental stroke, mice will be divided into a treated group and an untreated group that will be used as age-matched controls. Treated mice will be administered an APY cyclic peptide, such as APY-βA8.am, APY-d3 or APY-d4, or APY-d3 dimers disclosed herein once daily for four weeks. Motor performance evaluations of treated and untreated animals will be conducted on post-stroke days 1, 7, 13, 19, 26, and 34. Infarct volume will also be measured.

These results will show that treatment with a APY cyclic peptide disclosed herein will substantially improve motor function after experimental stroke. Mice treated with an APY cyclic peptide disclosed herein will exhibit on improved rotarod performance relative to control animals (untreated) as well as increased axonal sprouting. These results will demonstrate the therapeutic effects of APY cyclic peptides disclosed herein in inhibiting EphA4 signaling and their usefulness in treating stroke.

Example 12

Therapeutic Usefulness of APY Cyclic Peptides in Nerve Regeneration

To evaluate the therapeutic effects of APY cyclic peptides disclosed herein on nerve regeneration, EphA4 signaling inhibition by APY cyclic peptides was examined using a mouse corticospinal tract injury model for nerve regeneration. Spinal cord injury often leads to permanent incapacity because long axons cannot regenerate in the CNS. Eph receptors inhibit axon extension through an effect on the actin cytoskeleton. Severing of corticospinal axons causes EphA4 to accumulate at high levels in stumps of corticospinal axons, while a cognate ligand, ephrinB2, is upregulated at the lesion site so as to confine the injured axons.

Wild-type mice will be anesthetized and a spinal hemisection surgery will be performed in order to sever corticospinal axons in the T12-L1 region. Animals will be allowed to recover from the surgery and mice showing only complete paralysis will be used. Both hemisectioned mice, as well as un-operated mice used as age-matched controls, will be administered an APY cyclic peptide, such as APY-βA8.am, APY-d3 or APY-d4 disclosed herein, into the cervical spinal cord region by intracerebral infusion. Five weeks after spinal cord lesion, mice will be evaluated for nerve regeneration by using an anterograde tracing technique and immunohistochemistry using antibodies against EphA4 and glial fibrillary acidic protein (GFAP) as well as by using behavioral assessments before and after spinal hemisection like measuring stride length, ability to walk or climb on a grid and/or hindpaw grip strength.

These results will show that treatment with an APY cyclic peptide disclosed herein will substantially improve recovery in hemisectioned animals relative to controls by promoting axon sprouting and/or improving limb function and recovery. Mice treated with an APY cyclic peptide disclosed herein will exhibit axon sprouting, will show a reduction astrocytic gliosis and glial scaring, will demonstrate recovered stride length, the ability to walk on and/or climb a grid, and/or the ability to grasp with the affected hindpaw within 1-3 months of injury. These results will demonstrate the therapeutic effects of APY cyclic peptides disclosed herein in inhibiting EphA4 signaling and their usefulness in promoting nerve regeneration. In addition, these data will confirm the findings obtained with the KYL peptide (a less potent EphA4 peptide antagonist) that inhibition of EphA4 signaling provides therapeutic benefits in neuroregeneration.

Example 13

Therapeutic Treatments Using an APY Cyclic Peptide

A 46 year old male complains of muscle weakness and numbness in his hands and arms. After routine history and physical examination, a physician diagnosis the woman with ALS. The man is treated by oral administration a pharmaceutical composition comprising an APY cyclic peptide disclosed herein taken twice daily. Alternatively, the man is treated by administering the pharmaceutical composition once every three days. The man's condition is monitored and after about one month of treatment the man indicates there is improvement in his health, the numbness is not as severe and some strength has returned to his hands and arms. At a three month check-up, the man indicates that his numbness is gone, he does not suffer from any muscle weakness. This reduction in symptoms in ALS indicates successful treatment with the pharmaceutical composition disclosed herein. In a similar manner, a pharmaceutical composition disclosed herein may be used to treat other neurodegenerative diseases, such as, e.g., an Alexander disease, an Alper's disease, Alzheimer's disease, an ataxia telangiectasia, a Canavan disease, a Cockayne syndrome, a corticobasal degeneration, a Creutzfeldt-Jakob disease, a Guillain-Barre Syndrome a HIV-induced neurodegeneration, a Huntington disease, a Kennedy's disease, a Krabbe disease, a Lewy body dementia, a Machado-Joseph disease, a multiple sclerosis, a Parkinson's disease, a Pelizaeus-Merzbacher disease, a Pick's disease, a primary lateral sclerosis, a Refsum's disease, a Sandhoff disease, a Schilder's disease, a spinal cord injury, a Steele-Richardson-Olszewski disease, a stroke, a tabes dorsalis and/or a traumatic brain injury.

A 69 year old male complains of forgetfulness and not being able to remember certain events or activities. After routine history and physical examination, a physician diagnosis the woman with Alzheimer's disease. The man is treated by oral administration a pharmaceutical composition comprising an APY cyclic peptide disclosed herein taken twice daily. Alternatively, the man is treated by administering the pharmaceutical composition once every three days. The man's condition is monitored and after about one month of treatment the man indicates there is improvement in his health, his forgetfulness is not as severe and he can remember events or activities better. At a three month check-up, the man indicates that his forgetfulness and memory continue to improve. This reduction in symptoms in Alzheimer's disease indicates successful treatment with the pharmaceutical composition disclosed herein. In a similar manner, a pharmaceutical composition disclosed herein may be used to treat other neurodegenerative diseases, such as, e.g., an Alexander disease, an Alper's disease, an amyotrophic lateral sclerosis, an ataxia telangiectasia, a Canavan disease, a Cockayne syndrome, a corticobasal degeneration, a Creutzfeldt-Jakob disease, a Guillain-Barre Syndrome a HIV-induced neurodegeneration, a Huntington disease, a Kennedy's disease, a Krabbe disease, a Lewy body dementia, a Machado-Joseph disease, a multiple sclerosis, a Parkinson's disease, a Pelizaeus-Merzbacher disease, a Pick's disease, a primary lateral sclerosis, a Refsum's disease, a Sandhoff disease, a Schilder's disease, a spinal cord injury, a Steele-Richardson-Olszewski disease, a stroke, a tabes dorsalis and/or a traumatic brain injury.

A 51 year old female complains of hand tremors, eye pain and blurred vision, and fatigue. After routine history and physical examination, a physician diagnosis the woman with multiple sclerosis. The woman is treated by oral administration a pharmaceutical composition comprising an APY cyclic peptide disclosed herein taken once daily. The woman's condition is monitored and after about one week of treatment the woman indicates there is improvement in her health, her eye pain and blurred vision has subsided, her hand tremors are less and some energy has returned. At one and three month check-ups, the woman indicates that her eye pain and blurred vision is gone, she does not suffer from hand tremors, and she is not tired. This reduction in symptoms in multiple sclerosis indicates successful treatment with the pharmaceutical composition disclosed herein. In a similar manner, a pharmaceutical composition disclosed herein may be used to treat other neurodegenerative diseases, such as, e.g., an Alexander disease, an Alper's disease, Alzheimer's disease, an amyotrophic lateral sclerosis, an ataxia telangiectasia, a Canavan disease, a Cockayne syndrome, a corticobasal degeneration, a Creutzfeldt-Jakob disease, a Guillain-Barre Syndrome a HIV-induced neurodegeneration, a Huntington disease, a Kennedy's disease, a Krabbe disease, a Lewy body dementia, a Machado-Joseph disease, a Parkinson's disease, a Pelizaeus-Merzbacher disease, a Pick's disease, a primary lateral sclerosis, a Refsum's disease, a Sandhoff disease, a Schilder's disease, a spinal cord injury, a Steele-Richardson-Olszewski disease, a stroke, a tabes dorsalis and/or a traumatic brain injury.

A 66 year old male complains of severe pain after losing consciousness. A physician determines that the pain is due to central neuropathic pain caused by a stroke. The man is treated by administering a pharmaceutical composition comprising an APY cyclic peptide disclosed herein taken once every other day. Alternatively, the man is treated by administering the pharmaceutical composition once every three days. The man's condition is monitored and after about 7 days of treatment the man indicates that there is a reduction in pain. At one and three month check-ups, the man indicates that he continues to have reduced pain. Tests performed on the man indicate that neuronal regeneration is occurring. This reduction in central neuropathic pain symptoms and/or regenerative growth of neurons indicates successful treatment with the pharmaceutical composition disclosed herein. In a similar manner, a pharmaceutical composition disclosed herein may be used to promote neuroregeneration and/or neuroprotection caused by another condition, disease or disorder, such as hearing loss.

A 49 year old woman was diagnosed by her physician with advanced metastatic breast cancer. The metastatic breast cancer consisted of tumors, including several found in both lungs. The woman is treated by administering a pharmaceutical composition comprising an APY cyclic peptide disclosed herein taken once every third day. Alternatively, the woman is treated by administering the pharmaceutical composition once daily. One month after following this treatment, the patient was administered a CAT scan, which revealed that tumor growth had stopped and the breast cancer did not progress in the patient during this period of treatment. This reduction in tumor growth indicates successful treatment with the pharmaceutical composition disclosed herein. In a similar manner, a pharmaceutical composition disclosed herein may be used to treat a different type of cancer, such as, a glioblastoma, a gastric cancer, a pancreatic cancer, a prostate cancer, a breast cancer, a liver cancer, a leukemia or a Sezary syndrome.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about"; in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. An EphA4 receptor antagonist comprising a cyclic peptide having a length of 12 amino acids and including the sequence $X_1\text{-}X_2\text{-}X_3\text{-}C_4\text{-}X_5\text{-}X_6\text{-}X_7\text{-}\beta A_8\text{-}X_9\text{-}W\text{-}X_{11}\text{-}C_{12}$ (SEQ ID NO: 3), wherein $X_1$ is independently βA, D-A, A, E, G, Q, D, L, S, F, or Y; $X_2$ is independently P, A, G, Ahx, Ava, γAbu, βA or Sar; $X_3$ is independently Y, F, W, V, L, H or I; $X_5$ is independently V or L; $X_6$ is independently Y, F, W or H; $X_7$ is independently any amino acid; $X_9$ is independently any amino acid; and $X_{11}$ is independently any amino acid; wherein $C_4$ and $C_{12}$ form a disulfide bridge; and wherein $C_{12}$ is optionally amidated.

2. The EphA4 receptor antagonist according to claim 1, wherein $X_1$ is independently βA, D-A, A, E, G or Q; $X_2$ is P; $X_3$ is independently Y, F, W, V, L or H; $X_5$ is V; $X_6$ is independently Y, F or W; $X_7$ is independently any amino acid except P; $X_9$ is independently any amino acid except P; and/or $X_{11}$ is independently any amino acid except P.

3. The EphA4 receptor antagonist according to claim 2, wherein $X_3$ is independently Y, F or W.

4. The EphA4 receptor antagonist according to claim 2, wherein $X_7$ is independently R, T, N, D, S, Q, Y, K, A, G or E; $X_9$ is independently S, E, T, V, D, Y, Q, V, W, R, N, L, K or H; and $X_{11}$ is independently S, E, L, N, V, I, H, K, M, D, W, T or G.

5. The EphA4 receptor antagonist according to claim 4, wherein $X_7$ is independently R, T, N, D, S, or Q; $X_9$ is independently S, E, T, V, W, R, L, D, Y; and $X_{11}$ is independently S, E, L, N, T, K, V, I or H.

6. The EphA4 receptor antagonist according to claim 5, wherein $X_7$ is independently R, T, N, D, S, or Q; $X_9$ is independently S, E, T, V, D, Y; and $X_{11}$ is independently S, E, L, N, K, V, I or H.

7. The EphA4 receptor antagonist according to claim 6, wherein $X_7$ is independently R, T, or N; $X_9$ is independently S, E, T or V; and is independently S, E, L or N.

8. The EphA4 receptor antagonist according to claim 1, wherein the sequence comprises $X_1\text{-}P_2\text{-}X_3\text{-}C_4\text{-}X_5\text{-}X_6\text{-}X_7\text{-}\beta A_8\text{-}X_9\text{-}W_{10}\text{-}X_{11}\text{-}C_{12}$ (SEQ ID NO: 6), wherein $C_4$ and $C_{12}$ form a disulfide bridge; and wherein $C_{12}$ is optionally amidated.

9. The EphA4 receptor antagonist according to claim 1, wherein the sequence comprises $X_1\text{-}X_2\text{-}X_3\text{-}C_4\text{-}V_5\text{-}X_6\text{-}X_7\text{-}\beta A_8\text{-}X_9\text{-}W_{10}\text{-}X\text{-}C_{12}$ (SEQ ID NO: 9), wherein $C_4$ and $C_{12}$ form a disulfide bridge; and wherein $C_{12}$ is optionally amidated.

10. The EphA4 receptor antagonist according to claim 1, wherein the sequence comprises $X_1\text{-}P_2\text{-}X_3\text{-}C_4\text{-}V_5\text{-}X_6\text{-}X_7\text{-}\beta A_8\text{-}X_9\text{-}W_{10}\text{-}X_{11}\text{-}C_{12}$ (SEQ ID NO: 12), wherein $C_4$ and $C_{12}$ form a disulfide bridge; and wherein $C_{12}$ is optionally amidated.

11. The EphA4 receptor antagonist according to claim 1, wherein the sequence comprises $X_1\text{-}P_2\text{-}Y_3\text{-}C_4\text{-}V_5\text{-}X_6\text{-}X_7\text{-}\beta A_8\text{-}X_9\text{-}W_{10}\text{-}X_{11}\text{-}C_{12}$ (SEQ ID NO: 15), wherein $C_4$ and $C_{12}$ form a disulfide bridge; and wherein $C_{12}$ is optionally amidated.

12. The EphA4 receptor antagonist according to claim 1, wherein the sequence comprises $X_1\text{-}P_2\text{-}X_3\text{-}C_4\text{-}V_5\text{-}Y_6\text{-}X_7\text{-}\beta A_8\text{-}X_9\text{-}W_{10}\text{-}X_{11}\text{-}C_{12}$ (SEQ ID NO: 18), wherein $X_1$ is independently βA, D-A, A, E, G or Q; $X_3$ is independently Y, F, W, V, L or H; $X_7$ is independently any amino acid except P; $X_9$ is independently any amino acid except P; and $X_{11}$ is independently any amino acid except P; wherein $C_4$ and $C_{12}$ form a disulfide bridge; and wherein $C_{12}$ is optionally amidated.

13. The EphA4 receptor antagonist according to claim 1, wherein the sequence comprises $X_1\text{-}P_2\text{-}Y_3\text{-}C_4\text{-}V_5\text{-}Y_6\text{-}X_7\text{-}\beta A_8\text{-}X_9\text{-}W_{10}\text{-}X_{11}\text{-}C_{12}$ (SEQ ID NO: 21), wherein $X_1$ is independently βA, D-A, A, E, G or Q; $X_7$ is independently any amino acid except P; $X_9$ is independently any amino acid except P; and is independently any amino acid except P; wherein $C_4$ and $C_{12}$ form a disulfide bridge; and wherein $C_{12}$ is optionally amidated.

14. The EphA4 receptor antagonist according to claim 1, wherein the sequence comprises $X_1\text{-}P_2\text{-}Y_3\text{-}C_4\text{-}V_5\text{-}Y_6\text{-}R_7\text{-}\beta A_8\text{-}X_9\text{-}W_{10}\text{-}X_{11}\text{-}C_{12}$ (SEQ ID NO: 24), wherein $X_1$ is independently βA, D-A, A, E, G or Q; $X_9$ is independently any amino acid except P; and is independently any amino acid except P; wherein $C_4$ and $C_{12}$ form a disulfide bridge; and wherein $C_{12}$ is optionally amidated.

15. The EphA4 receptor antagonist according to claim 1, wherein $C_{12}$ is amidated.

16. The EphA4 receptor antagonist according to claim 1, wherein the sequence is APYCVYRβASWSC (SEQ ID NO: 35), APYCVYRβASWSC-am (SEQ ID NO: 36), APYCVYKβASWSC-am (SEQ ID NO: 45), βAPYCVYRβASWSC (SEQ ID NO: 46), βAPYCVYRβASWSC-am (SEQ ID NO: 47), βAPYCVYKβASWSC-am (SEQ ID NO: 48), βAPYCVYRβAEWEC (SEQ ID NO: 49), βAPYCVYRβAEWEC-am (SEQ ID NO: 50), D-APYCVYRβASWSC (SEQ ID NO: 51), D-APYCVYRβASWSC-am (SEQ ID NO: 52), APYCVWRβASWSC (SEQ ID NO: 53), APYCVYTβAEWLC (SEQ ID NO: 54), APYCVYNβATWNC (SEQ ID NO: 55), APYCVYRβAVWEC (SEQ ID NO: 56), APVCVWRβASWSC (SEQ ID NO: 57), APLCVWRβASWSC (SEQ ID NO: 58), APLCVYRβASWSC (SEQ ID NO: 59), APWCVFRβASWSC (SEQ ID NO: 60), APHCVFRβASWSC (SEQ ID NO: 61), APFCLYTβADWVC (SEQ ID NO: 62), APYCVYDβATWIC (SEQ ID NO: 63), APYCVYSβATWHC (SEQ ID NO: 64), APYCVYDβASWNC (SEQ ID NO: 65), APYCVYQβAYWKC (SEQ ID NO: 66), APYCVYRβASWSC (SEQ ID NO: 67), EPYCVYRβASWSC (SEQ ID NO: 68), APLCVYRβASWSC (SEQ ID NO: 69), Ahx-YCVYRβASWSC-am (SEQ ID NO: 119), Ava-YCVYRβASWSC-am (SEQ ID NO: 120), γAbu-YCVYRβASWSC-am (SEQ ID NO: 121), βA-YCVYRβASWSC-am (SEQ ID NO: 122), GYCVYRβASWSC-am (SEQ ID NO: 123) or Sar1-YCVYRβASWSC-am (SEQ ID NO: 124).

17. A pharmaceutical composition comprising one or more EphA4 receptor antagonist according to claim 1.

18. The pharmaceutical composition according to claim 17, wherein the one or more EphA4 receptor antagonist are each present in an amount of between about 100 ng to about 1,000 μg.

19. The pharmaceutical composition according to claim 17, wherein the pharmaceutical composition further comprises one or more pharmaceutical acceptable carriers.

20. A method of treating an EphA4-based disease, disorder or pathology, the method comprising administering an EphA4 receptor antagonist as defined in claim 1 or a pharmaceutical composition as defined in claim 17 to an individual in need thereof, wherein administration reduces one or more symptoms associated with the EphA4-based disease, disorder or pathology.

\* \* \* \* \*

```
                         SEQUENCE LISTING

<160> NUMBER OF SEQ ID NOS: 124

<210> SEQ ID NO 1
    <211> LENGTH: 12
    <212> TYPE: PRT
    <213> ORGANISM: Artificial Sequence
    <220> FEATURE:
    <223> OTHER INFORMATION: EphA4 receptor pepide antagonist

<400> SEQUENCE: 1

Lys Tyr Leu Pro Tyr Trp Pro Val Leu Ser Ser Leu
    1               5                   10

<210> SEQ ID NO 2
    <211> LENGTH: 12
    <212> TYPE: PRT
    <213> ORGANISM: Artificial Sequence
    <220> FEATURE:
    <223> OTHER INFORMATION: EphA4 receptor cyclic peptide antagonist

<400> SEQUENCE: 2

Ala Pro Tyr Cys Val Tyr Arg Gly Ser Trp Ser Cys
    1               5                   10

<210> SEQ ID NO 3
    <211> LENGTH: 12
    <212> TYPE: PRT
    <213> ORGANISM: Artificial Seqeunce
    <220> FEATURE:
    <223> OTHER INFORMATION: Consensus sequence for EphA4 receptor cyclic
          peptide antagonist
    <220> FEATURE:
    <221> NAME/KEY: VARIANT
    <222> LOCATION: (1)..(1)
    <223> OTHER INFORMATION: X is bAla, DAla, Ala, Glu, Gly, Gln, Asp, Leu,
          Ser, Phe, or Tyr
    <220> FEATURE:
    <221> NAME/KEY: VARIANT
    <222> LOCATION: (2)..(2)
    <223> OTHER INFORMATION: X is Pro or Ala
    <220> FEATURE:
    <221> NAME/KEY: VARIANT
    <222> LOCATION: (3)..(3)
    <223> OTHER INFORMATION: X is Tyr, Phe, Trp, Val, Leu, His or Ile
    <220> FEATURE:
    <221> NAME/KEY: VARIANT
    <222> LOCATION: (5)..(5)
    <223> OTHER INFORMATION: X is Val or Leu
    <220> FEATURE:
    <221> NAME/KEY: VARIANT
    <222> LOCATION: (6)..(6)
    <223> OTHER INFORMATION: X is Tyr, Phe, Trp or His
```

```
<220> FEATURE:
<221> NAME/KEY: VARIANT
<222> LOCATION: (7)..(7)
<223> OTHER INFORMATION: X is any amino acid
<220> FEATURE:
<221> NAME/KEY: MOD_RES
<222> LOCATION: (8)..(8)
<223> OTHER INFORMATION: X is bAla
<220> FEATURE:
<221> NAME/KEY: VARIANT
<222> LOCATION: (9)..(9)
<223> OTHER INFORMATION: X is any amino acid
<220> FEATURE:
<221> NAME/KEY: VARIANT
<222> LOCATION: (11)..(11)
<223> OTHER INFORMATION: X is any amino acid

<400> SEQUENCE: 3

Xaa Xaa Xaa Cys Xaa Xaa Xaa Xaa Xaa Trp Xaa Cys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Consensus sequence for EphA4 receptor cyclic
      peptide antagonist
<220> FEATURE:
<221> NAME/KEY: VARIANT
<222> LOCATION: (1)..(1)
<223> OTHER INFORMATION: X is Pro or Ala
<220> FEATURE:
<221> NAME/KEY: VARIANT
<222> LOCATION: (2)..(2)
<223> OTHER INFORMATION: X is Tyr, Phe, Trp, Val, Leu, His or Ile
<220> FEATURE:
<221> NAME/KEY: VARIANT
<222> LOCATION: (4)..(4)
<223> OTHER INFORMATION: X is Val or Leu
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: X is any amino acid
<220> FEATURE:
<221> NAME/KEY: MOD_RES
<222> LOCATION: (7)..(7)
<223> OTHER INFORMATION: X is bAla
<220> FEATURE:
<221> NAME/KEY: VARIANT
<222> LOCATION: (8)..(8)
<223> OTHER INFORMATION: X is any amino acid
<220> FEATURE:
<221> NAME/KEY: VARIANT
<222> LOCATION: (10)..(10)
<223> OTHER INFORMATION: X is any amino acid

<400> SEQUENCE: 4

Xaa Xaa Cys Xaa Xaa Xaa Xaa Xaa Trp Xaa Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Consensus sequence for EphA4 receptor cyclic
      peptide antagonist
<220> FEATURE:
<221> NAME/KEY: VARIANT
<222> LOCATION: (1)..(1)
```

```
<223> OTHER INFORMATION: X is Tyr, Phe, Trp, Val, Leu, His or Ile
<220> FEATURE:
<221> NAME/KEY: VARIANT
<222> LOCATION: (3)..(3)
<223> OTHER INFORMATION: X is Val or Leu
<220> FEATURE:
<221> NAME/KEY: VARIANT
<222> LOCATION: (4)..(4)
<223> OTHER INFORMATION: X is Tyr, Phe, Trp or His
<220> FEATURE:
<221> NAME/KEY: VARIANT
<222> LOCATION: (5)..(5)
<223> OTHER INFORMATION: X is any amino acid
<220> FEATURE:
<221> NAME/KEY: MOD_RES
<222> LOCATION: (6)..(6)
<223> OTHER INFORMATION: X is bAla
<220> FEATURE:
<221> NAME/KEY: VARIANT
<222> LOCATION: (7)..(7)
<223> OTHER INFORMATION: X is any amino acid
<220> FEATURE:
<221> NAME/KEY: VARIANT
<222> LOCATION: (9)..(9)
<223> OTHER INFORMATION: X is any amino acid

<400> SEQUENCE: 5

Xaa Cys Xaa Xaa Xaa Xaa Xaa Trp Xaa Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Consensus sequence for EphA4 receptor cyclic
      peptide antagonist
<220> FEATURE:
<221> NAME/KEY: VARIANT
<222> LOCATION: (1)..(1)
<223> OTHER INFORMATION: X is bAla, DAla, Ala, Glu, Gly or Gln
<220> FEATURE:
<221> NAME/KEY: VARIANT
<222> LOCATION: (3)..(3)
<223> OTHER INFORMATION: X is Tyr, Phe, Trp, Val, Leu or His
<220> FEATURE:
<221> NAME/KEY: VARIANT
<222> LOCATION: (5)..(5)
<223> OTHER INFORMATION: X is Val or Leu
<220> FEATURE:
<221> NAME/KEY: VARIANT
<222> LOCATION: (6)..(6)
<223> OTHER INFORMATION: X is Tyr, Phe, Trp or His
<220> FEATURE:
<221> NAME/KEY: VARIANT
<222> LOCATION: (7)..(7)
<223> OTHER INFORMATION: X is any amino acid except Pro
<220> FEATURE:
<221> NAME/KEY: MOD_RES
<222> LOCATION: (8)..(8)
<223> OTHER INFORMATION: X is bAla
<220> FEATURE:
<221> NAME/KEY: VARIANT
<222> LOCATION: (9)..(9)
<223> OTHER INFORMATION: X is any amino acid except Pro
<220> FEATURE:
<221> NAME/KEY: VARIANT
<222> LOCATION: (11)..(11)
<223> OTHER INFORMATION: X is any amino acid except Pro

<400> SEQUENCE: 6

Xaa Pro Xaa Cys Xaa Xaa Xaa Xaa Xaa Trp Xaa Cys
1               5                   10

<210> SEQ ID NO 7
```

```
<211> LENGTH: 11
<212> TYPE: PRT
<213> ORGANISM: Artificial Sequence
<220> FEATURE:
<223> OTHER INFORMATION: Consensus sequence for EphA4 receptor cyclic
      peptide antagonist
<220> FEATURE:
<221> NAME/KEY: VARIANT
<222> LOCATION: (2)..(2)
<223> OTHER INFORMATION: X is Tyr, Phe, Trp, Val, Leu or His
<220> FEATURE:
<221> NAME/KEY: VARIANT
<222> LOCATION: (4)..(4)
<223> OTHER INFORMATION: X is Val or Leu
<220> FEATURE:
<221> NAME/KEY: VARIANT
<222> LOCATION: (5)..(5)
<223> OTHER INFORMATION: X is Tyr, Phe, Trp or His
<220> FEATURE:
<221> NAME/KEY: VARIANT
<222> LOCATION: (6)..(6)
<223> OTHER INFORMATION: X is any amino acid except Pro
<220> FEATURE:
<221> NAME/KEY: MOD_RES
<222> LOCATION: (7)..(7)
<223> OTHER INFORMATION: X is bAla
<220> FEATURE:
<221> NAME/KEY: VARIANT
<222> LOCATION: (8)..(8)
<223> OTHER INFORMATION: X is any amino acid except Pro
<220> FEATURE:
<221> NAME/KEY: VARIANT
<222> LOCATION: (10)..(10)
<223> OTHER INFORMATION: X is any amino acid except Pro

<400> SEQUENCE: 7

Pro Xaa Cys Xaa Xaa Xaa Xaa Xaa Trp Xaa Cys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Consensus sequence for EphA4 receptor cyclic
      peptide antagonist
<220> FEATURE:
<221> NAME/KEY: VARIANT
<222> LOCATION: (1)..(1)
<223> OTHER INFORMATION: X is Tyr, Phe, Trp, Val, Leu or His
<220> FEATURE:
<221> NAME/KEY: VARIANT
<222> LOCATION: (3)..(3)
<223> OTHER INFORMATION: X is Val or Leu
<220> FEATURE:
<221> NAME/KEY: VARIANT
<222> LOCATION: (4)..(4)
<223> OTHER INFORMATION: X is Tyr, Phe, Trp or His
<220> FEATURE:
<221> NAME/KEY: VARIANT
<222> LOCATION: (5)..(5)
<223> OTHER INFORMATION: X is any amino acid except Pro
<220> FEATURE:
<221> NAME/KEY: MOD_RES
<222> LOCATION: (6)..(6)
<223> OTHER INFORMATION: X is bAla
<220> FEATURE:
<221> NAME/KEY: VARIANT
<222> LOCATION: (7)..(7)
<223> OTHER INFORMATION: X is any amino acid except Pro
<220> FEATURE:
<221> NAME/KEY: VARIANT
<222> LOCATION: (9)..(9)
<223> OTHER INFORMATION: X is any amino acid except Pro

<400> SEQUENCE: 8
```

Xaa Cys Xaa Xaa Xaa Xaa Xaa Trp Xaa Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Consensus sequence for EphA4 receptor cyclic
      peptide antagonist
<220> FEATURE:
<221> NAME/KEY: VARIANT
<222> LOCATION: (1)..(1)
<223> OTHER INFORMATION: X is bAla, DAla, Ala, Glu, Gly or Gln
<220> FEATURE:
<221> NAME/KEY: VARIANT
<222> LOCATION: (2)..(2)
<223> OTHER INFORMATION: X is Pro or Ala
<220> FEATURE:
<221> NAME/KEY: VARIANT
<222> LOCATION: (3)..(3)
<223> OTHER INFORMATION: X is Tyr, Phe, Trp, Val, Leu or His
<220> FEATURE:
<221> NAME/KEY: VARIANT
<222> LOCATION: (6)..(6)
<223> OTHER INFORMATION: X is Tyr, Phe, Trp or His
<220> FEATURE:
<221> NAME/KEY: VARIANT
<222> LOCATION: (7)..(7)
<223> OTHER INFORMATION: X is any amino acid except Pro
<220> FEATURE:
<221> NAME/KEY: MOD_RES
<222> LOCATION: (8)..(8)
<223> OTHER INFORMATION: X is bAla
<220> FEATURE:
<221> NAME/KEY: VARIANT
<222> LOCATION: (9)..(9)
<223> OTHER INFORMATION: X is any amino acid except Pro
<220> FEATURE:
<221> NAME/KEY: VARIANT
<222> LOCATION: (11)..(11)
<223> OTHER INFORMATION: X is any amino acid except Pro

<400> SEQUENCE: 9

Xaa Xaa Xaa Cys Val Xaa Xaa Xaa Xaa Trp Xaa Cys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Consensus sequence for EphA4 receptor
      antagonist cyclic peptide
<220> FEATURE:
<221> NAME/KEY: VARIANT
<222> LOCATION: (1)..(1)
<223> OTHER INFORMATION: X is Pro or Ala
<220> FEATURE:
<221> NAME/KEY: VARIANT
<222> LOCATION: (2)..(2)
<223> OTHER INFORMATION: X is Tyr, Phe, Trp, Val, Leu or His
<220> FEATURE:
<221> NAME/KEY: VARIANT
<222> LOCATION: (5)..(5)
<223> OTHER INFORMATION: X is Tyr, Phe, Trp or His
<220> FEATURE:
<221> NAME/KEY: VARIANT
<222> LOCATION: (6)..(6)
<223> OTHER INFORMATION: X is any amino acid except Pro
<220> FEATURE:
<221> NAME/KEY: MOD_RES
<222> LOCATION: (7)..(7)
<223> OTHER INFORMATION: X is bAla
<220> FEATURE:
<221> NAME/KEY: VARIANT

```
<222> LOCATION: (8)..(8)
<223> OTHER INFORMATION: X is any amino acid except Pro
<220> FEATURE:
<221> NAME/KEY: VARIANT
<222> LOCATION: (10)..(10)
<223> OTHER INFORMATION: X is any amino acid except Pro

<400> SEQUENCE: 10

Xaa Xaa Cys Val Xaa Xaa Xaa Xaa Trp Xaa Cys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Consensus sequence for EphA4 receptor
      antagonist cyclic peptide
<220> FEATURE:
<221> NAME/KEY: VARIANT
<222> LOCATION: (1)..(1)
<223> OTHER INFORMATION: X is Tyr, Phe, Trp, Val, Leu or His
<220> FEATURE:
<221> NAME/KEY: VARIANT
<222> LOCATION: (4)..(4)
<223> OTHER INFORMATION: X is Tyr, Phe, Trp or His
<220> FEATURE:
<221> NAME/KEY: VARIANT
<222> LOCATION: (5)..(5)
<223> OTHER INFORMATION: X is any amino acid except Pro
<220> FEATURE:
<221> NAME/KEY: MOD_RES
<222> LOCATION: (6)..(6)
<223> OTHER INFORMATION: X is bAla
<220> FEATURE:
<221> NAME/KEY: VARIANT
<222> LOCATION: (7)..(7)
<223> OTHER INFORMATION: X is any amino acid except Pro
<220> FEATURE:
<221> NAME/KEY: VARIANT
<222> LOCATION: (9)..(9)
<223> OTHER INFORMATION: X is any amino acid except Pro

<400> SEQUENCE: 11

Xaa Cys Val Xaa Xaa Xaa Xaa Trp Xaa Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Consensus sequence for EphA4 receptor cyclic
      peptide antagonist
<220> FEATURE:
<221> NAME/KEY: VARIANT
<222> LOCATION: (1)..(1)
<223> OTHER INFORMATION: X is bAla, DAla, Ala, Glu, Gly or Gln
<220> FEATURE:
<221> NAME/KEY: VARIANT
<222> LOCATION: (3)..(3)
<223> OTHER INFORMATION: X is Tyr, Phe, Trp, Val, Leu or His
<220> FEATURE:
<221> NAME/KEY: VARIANT
<222> LOCATION: (6)..(6)
<223> OTHER INFORMATION: X is Tyr, Phe, Trp or His
<220> FEATURE:
<221> NAME/KEY: VARIANT
<222> LOCATION: (7)..(7)
<223> OTHER INFORMATION: X is any amino acid except Pro
<220> FEATURE:
<221> NAME/KEY: MOD_RES
<222> LOCATION: (8)..(8)
<223> OTHER INFORMATION: X is bAla
<220> FEATURE:
```

```
<221> NAME/KEY: VARIANT
<222> LOCATION: (9)..(9)
<223> OTHER INFORMATION: X is any amino acid except Pro
<220> FEATURE:
<221> NAME/KEY: VARIANT
<222> LOCATION: (11)..(11)
<223> OTHER INFORMATION: X is any amino acid except Pro

<400> SEQUENCE: 12

Xaa Pro Xaa Cys Val Xaa Xaa Xaa Xaa Trp Xaa Cys
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Consensus sequence for EphA4 receptor
      antagonist cyclic peptide
<220> FEATURE:
<221> NAME/KEY: VARIANT
<222> LOCATION: (2)..(2)
<223> OTHER INFORMATION: X is Tyr, Phe, Trp, Val, Leu or His
<220> FEATURE:
<221> NAME/KEY: VARIANT
<222> LOCATION: (5)..(5)
<223> OTHER INFORMATION: X is Tyr, Phe, Trp or His
<220> FEATURE:
<221> NAME/KEY: VARIANT
<222> LOCATION: (6)..(6)
<223> OTHER INFORMATION: X is any amino acid except Pro
<220> FEATURE:
<221> NAME/KEY: MOD_RES
<222> LOCATION: (7)..(7)
<223> OTHER INFORMATION: X is bAla
<220> FEATURE:
<221> NAME/KEY: VARIANT
<222> LOCATION: (8)..(8)
<223> OTHER INFORMATION: X is any amino acid except Pro
<220> FEATURE:
<221> NAME/KEY: VARIANT
<222> LOCATION: (10)..(10)
<223> OTHER INFORMATION: X is any amino acid except Pro

<400> SEQUENCE: 13

Pro Xaa Cys Val Xaa Xaa Xaa Xaa Trp Xaa Cys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Consensus sequence for EphA4 receptor
      antagonist cyclic peptide
<220> FEATURE:
<221> NAME/KEY: VARIANT
<222> LOCATION: (1)..(1)
<223> OTHER INFORMATION: X is Tyr, Phe, Trp, Val, Leu or His
<220> FEATURE:
<221> NAME/KEY: VARIANT
<222> LOCATION: (4)..(4)
<223> OTHER INFORMATION: X is Tyr, Phe, Trp or His
<220> FEATURE:
<221> NAME/KEY: VARIANT
<222> LOCATION: (5)..(5)
<223> OTHER INFORMATION: X is any amino acid except Pro
<220> FEATURE:
<221> NAME/KEY: MOD_RES
<222> LOCATION: (6)..(6)
<223> OTHER INFORMATION: X is bAla
<220> FEATURE:
<221> NAME/KEY: VARIANT
<222> LOCATION: (7)..(7)
<223> OTHER INFORMATION: X is any amino acid except Pro
```

-continued

```
<220> FEATURE:
<221> NAME/KEY: VARIANT
<222> LOCATION: (9)..(9)
<223> OTHER INFORMATION: X is any amino acid except Pro

<400> SEQUENCE: 14

Xaa Cys Val Xaa Xaa Xaa Xaa Trp Xaa Cys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Consensus sequence for EphA4 receptor cyclic
      peptide antagonist
<220> FEATURE:
<221> NAME/KEY: VARIANT
<222> LOCATION: (1)..(1)
<223> OTHER INFORMATION: X is bAla, DAla, Ala, Glu, Gly or Gln
<220> FEATURE:
<221> NAME/KEY: VARIANT
<222> LOCATION: (6)..(6)
<223> OTHER INFORMATION: X is Tyr, Phe, Trp or His
<220> FEATURE:
<221> NAME/KEY: VARIANT
<222> LOCATION: (7)..(7)
<223> OTHER INFORMATION: X is any amino acid except Pro
<220> FEATURE:
<221> NAME/KEY: MOD_RES
<222> LOCATION: (8)..(8)
<223> OTHER INFORMATION: X is bAla
<220> FEATURE:
<221> NAME/KEY: VARIANT
<222> LOCATION: (9)..(9)
<223> OTHER INFORMATION: X is any amino acid except Pro
<220> FEATURE:
<221> NAME/KEY: VARIANT
<222> LOCATION: (11)..(11)
<223> OTHER INFORMATION: X is any amino acid except Pro

<400> SEQUENCE: 15

Xaa Pro Tyr Cys Val Xaa Xaa Xaa Xaa Trp Xaa Cys
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Consensus sequence for EphA4 receptor
      antagonist cyclic peptide
<220> FEATURE:
<221> NAME/KEY: VARIANT
<222> LOCATION: (5)..(5)
<223> OTHER INFORMATION: X is Tyr, Phe, Trp or His
<220> FEATURE:
<221> NAME/KEY: VARIANT
<222> LOCATION: (6)..(6)
<223> OTHER INFORMATION: X is any amino acid except Pro
<220> FEATURE:
<221> NAME/KEY: MOD_RES
<222> LOCATION: (7)..(7)
<223> OTHER INFORMATION: X is bAla
<220> FEATURE:
<221> NAME/KEY: VARIANT
<222> LOCATION: (8)..(8)
<223> OTHER INFORMATION: X is any amino acid except Pro
<220> FEATURE:
<221> NAME/KEY: VARIANT
<222> LOCATION: (10)..(10)
<223> OTHER INFORMATION: X is any amino acid except Pro

<400> SEQUENCE: 16
```

-continued

```
Pro Tyr Cys Val Xaa Xaa Xaa Xaa Trp Xaa Cys
1               5                   10
```

<210> SEQ ID NO 17
<211> LENGTH: 10
<212> TYPE: PRT
<213> ORGANISM: Artificial Sequence
<220> FEATURE:
<223> OTHER INFORMATION: Consensus sequence for EphA4 receptor
      antagonist c

```
<213> ORGANISM: Artificial Sequence
<220> FEATURE:
<223> OTHER INFORMATION: Consensus sequence for EphA4 receptor
      antagonist c

```
<223> OTHER INFORMATION: X is any amino acid except Pro
<220> FEATURE:
<221> NAME/KEY: MOD_RES
<222> LOCATION: (8)..(8)
<223> OTHER INFORMATION: X is bAla
<220> FEATURE:
<221> NAME/KEY: VARIANT
<222> LOCATION: (9)..(9)
<223> OTHER INFORMATION: X is any amino acid except Pro
<220> FEATURE:
<221> NAME/KEY: VARIANT
<222> LOCATION: (11)..(11)
<223> OTHER INFORMATION: X is any amino acid except Pro

<400> SEQUENCE: 21

Xaa Pro Tyr Cys Val Tyr Xaa Xaa Xaa Trp Xaa Cys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Consensus sequence for EphA4 receptor
      antagonist cyclic peptide
<220> FEATURE:
<221> NAME/KEY: VARIANT
<222> LOCATION: (6)..(6)
<223> OTHER INFORMATION: X is any amino acid except Pro
<220> FEATURE:
<221> NAME/KEY: MOD_RES
<222> LOCATION: (7)..(7)
<223> OTHER INFORMATION: X is bAla
<220> FEATURE:
<221> NAME/KEY: VARIANT
<222> LOCATION: (8)..(8)
<223> OTHER INFORMATION: X is any amino acid except Pro
<220> FEATURE:
<221> NAME/KEY: VARIANT
<222> LOCATION: (10)..(10)
<223> OTHER INFORMATION: X is any amino acid except Pro

<400> SEQUENCE: 22

Pro Tyr Cys Val Tyr Xaa Xaa Xaa Trp Xaa Cys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Consensus sequence for EphA4 receptor
      antagonist cyclic peptide
<220> FEATURE:
<221> NAME/KEY: VARIANT
<222> LOCATION: (5)..(5)
<223> OTHER INFORMATION: X is any amino acid except Pro
<220> FEATURE:
<221> NAME/KEY: MOD_RES
<222> LOCATION: (6)..(6)
<223> OTHER INFORMATION: X is bAla
<220> FEATURE:
<221> NAME/KEY: VARIANT
<222> LOCATION: (7)..(7)
<223> OTHER INFORMATION: X is any amino acid except Pro
<220> FEATURE:
<221> NAME/KEY: VARIANT
<222> LOCATION: (9)..(9)
<223> OTHER INFORMATION: X is any amino acid except Pro

<400> SEQUENCE: 23

Tyr Cys Val Tyr Xaa Xaa Xaa Trp Xaa Cys
1               5                   10
```

```
<210> SEQ ID NO 24
<211> LENGTH: 12
<212> TYPE: PRT
<213> ORGANISM: Artificial Sequence
<220> FEATURE:
<223> OTHER INFORMATION: Consensus sequence for EphA4 receptor cyclic
      peptide antagonist
<220> FEATURE:
<221> NAME/KEY: VARIANT
<222> LOCATION: (1)..(1)
<223> OTHER INFORMATION: X is bAla, DAla, Ala, Glu, Gly or Gln
<220> FEATURE:
<221> NAME/KEY: MOD_RES
<222> LOCATION: (8)..(8)
<223> OTHER INFORMATION: X is bAla
<220> FEATURE:
<221> NAME/KEY: VARIANT
<222> LOCATION: (9)..(9)
<223> OTHER INFORMATION: X is any amino acid except Pro
<220> FEATURE:
<221> NAME/KEY: VARIANT
<222> LOCATION: (11)..(11)
<223> OTHER INFORMATION: X is any amino acid except Pro

<400> SEQUENCE: 24

Xaa Pro Tyr Cys Val Tyr Arg Xaa Xaa Trp Xaa Cys
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Consensus sequence for EphA4 receptor
      antagonist cyclic peptide
<220> FEATURE:
<221> NAME/KEY: MOD_RES
<222> LOCATION: (7)..(7)
<223> OTHER INFORMATION: bAla
<220> FEATURE:
<221> NAME/KEY: VARIANT
<222> LOCATION: (8)..(8)
<223> OTHER INFORMATION: X is any amino acid except Pro
<220> FEATURE:
<221> NAME/KEY: VARIANT
<222> LOCATION: (10)..(10)
<223> OTHER INFORMATION: X is any amino acid except Pro

<400> SEQUENCE: 25

Pro Tyr Cys Val Tyr Arg Xaa Xaa Trp Xaa Cys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Consensus sequence for EphA4 receptor
      antagonist cyclic peptide
<220> FEATURE:
<221> NAME/KEY: MOD_RES
<222> LOCATION: (6)..(6)
<223> OTHER INFORMATION: X is bAla
<220> FEATURE:
<221> NAME/KEY: VARIANT
<222> LOCATION: (7)..(7)
<223> OTHER INFORMATION: X is any amino acid except Pro
<220> FEATURE:
<221> NAME/KEY: VARIANT
<222> LOCATION: (9)..(9)
<223> OTHER INFORMATION: X is any amino acid except Pro

<400> SEQUENCE: 26
```

Tyr Cys Val Tyr Arg Xaa Xaa Trp Xaa Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (12)..(12)
<223> OTHER INFORMATION: AMIDATION

<400> SEQUENCE: 27

Ala Pro Tyr Cys Val Tyr Arg Gly Ser Trp Ser Cys
1               5                   10

<210> SEQ ID NO 28
<211> LENGTH: 11
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (11)..(11)
<223> OTHER INFORMATION: AMIDATION

<400> SEQUENCE: 28

Pro Tyr Cys Val Tyr Arg Gly Ser Trp Ser Cys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: VARIANT
<222> LOCATION: (1)..(1)
<223> OTHER INFORMATION: X is DAla
<220> FEATURE:
<221> NAME/KEY: MOD_RES
<222> LOCATION: (12)..(12)
<223> OTHER INFORMATION: AMIDATION

<400> SEQUENCE: 29

Xaa Pro Tyr Cys Val Tyr Arg Gly Ser Trp Ser Cys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: VARIANT
<222> LOCATION: (1)..(1)
<223> OTHER INFORMATION: X is bAla
<220> FEATURE:
<221> NAME/KEY: MOD_RES
<222> LOCATION: (12)..(12)
<223> OTHER INFORMATION: AMIDATION

<400> SEQUENCE: 30

```
Xaa Pro Tyr Cys Val Tyr Arg Gly Ser Trp Ser Cys
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (12)..(12)
<223> OTHER INFORMATION: AMIDATION

<400> SEQUENCE: 31

```
Ala Pro Tyr Cys Val Tyr Arg Ala Ser Trp Ser Cys
1               5                   10
```

<210> SEQ ID NO 32
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is Aib
<220> FEATURE:
<221> NAME/KEY: MOD_RES
<222> LOCATION: (12)..(12)
<223> OTHER INFORMATION: AMIDATION

<400> SEQUENCE: 32

```
Ala Pro Tyr Cys Val Tyr Arg Xaa Ser Trp Ser Cys
1               5                   10
```

<210> SEQ ID NO 33
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is DAla

<400> SEQUENCE: 33

```
Ala Pro Tyr Cys Val Tyr Arg Xaa Ser Trp Ser Cys
1               5                   10
```

<210> SEQ ID NO 34
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is D-Ala
<220> FEATURE:
<221> NAME/KEY: MOD_RES
<222> LOCATION: (12)..(12)
<223> OTHER INFORMATION: AMIDATION

<400> SEQUENCE: 34

```
Ala Pro Tyr Cys Val Tyr Arg Xaa Ser Trp Ser Cys
1               5                   10
```

<210> SEQ ID NO 35
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 35

Ala Pro Tyr Cys Val Tyr Arg Xaa Ser Trp Ser Cys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla
<220> FEATURE:
<221> NAME/KEY: MOD_RES
<222> LOCATION: (12)..(12)
<223> OTHER INFORMATION: AMIDATION

<400> SEQUENCE: 36

Ala Pro Tyr Cys Val Tyr Arg Xaa Ser Trp Ser Cys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (8)..(8)
<223> OTHER INFORMATION: X is bAla
<220> FEATURE:
<221> NAME/KEY: MOD_RES
<222> LOCATION: (12)..(12)
<223> OTHER INFORMATION: AMIDATION

<400> SEQUENCE: 37

Ala Pro Tyr Cys Val Tyr Arg Xaa Ser Trp Ser Cys
1               5                   10

<210> SEQ ID NO 38
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: VARIANT
<222> LOCATION: (8)..(8)
<223> OTHER INFORMATION: X is bALA
<220> FEATURE:
<221> NAME/KEY: MOD_RES
<222> LOCATION: (12)..(12)
<223> OTHER INFORMATION: AMIDATION

```
<400> SEQUENCE: 38

Ala Leu Tyr Cys Val Tyr Arg Xaa Ser Trp Ser Cys
1               5                   10

<210> SEQ ID NO 39
<211> LENGTH: 11
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: VARIANT
<222> LOCATION: (7)..(7)
<223> OTHER INFORMATION: X is bAla
<220> FEATURE:
<221> NAME/KEY: MOD_RES
<222> LOCATION: (11)..(11)
<223> OTHER INFORMATION: AMIDATION

<400> SEQUENCE: 39

Pro Tyr Cys Val Tyr Arg Xaa Ser Trp Ser Cys
1               5                   10

<210> SEQ ID NO 40
<211> LENGTH: 11
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (7)..(7)
<223> OTHER INFORMATION: X is bAla
<220> FEATURE:
<221> NAME/KEY: MOD_RES
<222> LOCATION: (11)..(11)
<223> OTHER INFORMATION: AMIDATION

<400> SEQUENCE: 40

Pro Tyr Cys Val Tyr Arg Xaa Ser Trp Ser Cys
1               5                   10

<210> SEQ ID NO 41
<211> LENGTH: 11
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: VARIANT
<222> LOCATION: (7)..(7)
<223> OTHER INFORMATION: X is bAla
<220> FEATURE:
<221> NAME/KEY: MOD_RES
<222> LOCATION: (11)..(11)
<223> OTHER INFORMATION: AMIDATION

<400> SEQUENCE: 41

Lys Tyr Cys Val Tyr Arg Xaa Ser Trp Ser Cys
1               5                   10

<210> SEQ ID NO 42
<211> LENGTH: 11
<212> TYPE: PRT
<213> ORGANISM: Artificial Sequence
<220> FEATURE:
```

-continued

```
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (7)..(7)
<223> OTHER INFORMATION: X is bAla
<220> FEATURE:
<221> NAME/KEY: MOD_RES
<222> LOCATION: (11)..(11)
<223> OTHER INFORMATION: AMIDATION

<400> SEQUENCE: 42

Lys Tyr Cys Val Tyr Arg Xaa Ser Trp Ser Cys
1               5                   10

<210> SEQ ID NO 43
<211> LENGTH: 11
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: VARIANT
<222> LOCATION: (7)..(7)
<223> OTHER INFORMATION: X is bAla
<220> FEATURE:
<221> NAME/KEY: MOD_RES
<222> LOCATION: (11)..(11)
<223> OTHER INFORMATION: AMIDATION

<400> SEQUENCE: 43

His Tyr Cys Val Tyr Arg Xaa Ser Trp Ser Cys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: VARIANT
<222> LOCATION: (6)..(6)
<223> OTHER INFORMATION: X is bAla
<220> FEATURE:
<221> NAME/KEY: MOD_RES
<222> LOCATION: (10)..(10)
<223> OTHER INFORMATION: AMIDATION

<400> SEQUENCE: 44

Tyr Cys Val Tyr Arg Xaa Ser Trp Ser Cys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: VARIANT
<222> LOCATION: (8)..(8)
<223> OTHER INFORMATION: X is bAla

<400> SEQUENCE: 45

Ala Pro Tyr Cys Val Tyr Lys Xaa Ser Trp Ser Cys
1               5                   10
```

```
<210> SEQ ID NO 46
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: X is bAla
<220> FEATURE:
<221> NAME/KEY: MOD_RES
<222> LOCATION: (8)..(8)
<223> OTHER INFORMATION: X is bAla

<400> SEQUENCE: 46

Xaa Pro Tyr Cys Val Tyr Arg Xaa Ser Trp Ser Cys
 1               5                  10

<210> SEQ ID NO 47
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: X is bAla
<220> FEATURE:
<221> NAME/KEY: MOD_RES
<222> LOCATION: (8)..(8)
<223> OTHER INFORMATION: X is bAla
<220> FEATURE:
<221> NAME/KEY: MOD_RES
<222> LOCATION: (12)..(12)
<223> OTHER INFORMATION: AMIDATION

<400> SEQUENCE: 47

Xaa Pro Tyr Cys Val Tyr Arg Xaa Ser Trp Ser Cys
 1               5                  10

<210> SEQ ID NO 48
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: VARIANT
<222> LOCATION: (1)..(1)
<223> OTHER INFORMATION: X is bAla
<220> FEATURE:
<221> NAME/KEY: VARIANT
<222> LOCATION: (8)..(8)
<223> OTHER INFORMATION: X is bAla

<400> SEQUENCE: 48

Xaa Pro Tyr Cys Val Tyr Arg Xaa Ser Trp Ser Cys
 1               5                  10

<210> SEQ ID NO 49
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: X is bAla
<220> FEATURE:
<221> NAME/KEY: MOD_RES
```

```
<222> LOCATION: (8)..(8)
<223> OTHER INFORMATION: X is bAla

<400> SEQUENCE: 49

Xaa Pro Tyr Cys Val Tyr Arg Xaa Glu Trp Glu Cys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: X is bAla
<220> FEATURE:
<221> NAME/KEY: MOD_RES
<222> LOCATION: (8)..(8)
<223> OTHER INFORMATION: X is bAla
<220> FEATURE:
<221> NAME/KEY: MOD_RES
<222> LOCATION: (12)..(12)
<223> OTHER INFORMATION: AMIDATION

<400> SEQUENCE: 50

Xaa Pro Tyr Cys Val Tyr Arg Xaa Glu Trp Glu Cys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: X is D-Ala
<220> FEATURE:
<221> NAME/KEY: MOD_RES
<222> LOCATION: (8)..(8)
<223> OTHER INFORMATION: X is bAla

<400> SEQUENCE: 51

Xaa Pro Tyr Cys Val Tyr Arg Xaa Ser Trp Ser Cys
1               5                   10

<210> SEQ ID NO 52
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: X is D-Ala
<220> FEATURE:
<221> NAME/KEY: MOD_RES
<222> LOCATION: (8)..(8)
<223> OTHER INFORMATION: X is bAla
<220> FEATURE:
<221> NAME/KEY: MOD_RES
<222> LOCATION: (12)..(12)
<223> OTHER INFORMATION: AMIDATION

<400> SEQUENCE: 52

Xaa Pro Tyr Cys Val Tyr Arg Xaa Ser Trp Ser Cys
1               5                   10
```

```
<210> SEQ ID NO 53
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 53

Ala Pro Tyr Cys Val Trp Arg Xaa Ser Trp Ser Cys
1               5                   10

<210> SEQ ID NO 54
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 54

Ala Pro Tyr Cys Val Tyr Thr Xaa Glu Trp Leu Cys
1               5                   10

<210> SEQ ID NO 55
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 55

Ala Pro Tyr Cys Val Tyr Asn Xaa Thr Trp Asn Cys
1               5                   10

<210> SEQ ID NO 56
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 56

Ala Pro Tyr Cys Val Tyr Arg Xaa Val Trp Glu Cys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla
```

<400> SEQUENCE: 57

Ala Pro Val Cys Val Trp Arg Xaa Ser Trp Ser Cys
1               5                   10

<210> SEQ ID NO 58
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 58

Ala Pro Leu Cys Val Trp Arg Xaa Ser Trp Ser Cys
1               5                   10

<210> SEQ ID NO 59
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 59

Ala Pro Leu Cys Val Tyr Arg Xaa Ser Trp Ser Cys
1               5                   10

<210> SEQ ID NO 60
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 60

Ala Pro Trp Cys Val Phe Arg Xaa Ser Trp Ser Cys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 61

Ala Pro His Cys Val Phe Arg Xaa Ser Trp Ser Cys
1               5                   10

<210> SEQ ID NO 62
<211> LENGTH: 12
<212> TYPE: PRT
<213> ORGANISM: Artificial Sequence

```
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 62

Ala Pro Phe Cys Leu Tyr Thr Xaa Asp Trp Val Cys
1               5                   10

<210> SEQ ID NO 63
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 63

Ala Pro Tyr Cys Val Tyr Asp Xaa Thr Trp Ile Cys
1               5                   10

<210> SEQ ID NO 64
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 64

Ala Pro Tyr Cys Val Tyr Ser Xaa Thr Trp His Cys
1               5                   10

<210> SEQ ID NO 65
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 65

Ala Pro Tyr Cys Val Tyr Asp Xaa Ser Trp Asn Cys
1               5                   10

<210> SEQ ID NO 66
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 66

Ala Pro Tyr Cys Val Tyr Gln Xaa Tyr Trp Lys Cys
1               5                   10
```

<210> SEQ ID NO 67
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 67

Ala Pro Tyr Cys Val Tyr Arg Xaa Ser Trp Ser Cys
1               5                   10

<210> SEQ ID NO 68
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 68

Glu Pro Tyr Cys Val Tyr Arg Xaa Ser Trp Ser Cys
1               5                   10

<210> SEQ ID NO 69
<211> LENGTH: 12
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (8)..(8)
<223> OTHER INFORMATION: X is bAla

<400> SEQUENCE: 69

Ala Pro Leu Cys Val Tyr Arg Xaa Ser Trp Ser Cys
1               5                   10

<210> SEQ ID NO 70
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 70

Ala Pro Tyr Cys Val Trp Arg Gly Ser Trp Ser Cys
1               5                   10

<210> SEQ ID NO 71
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 71

Ala Pro Val Cys Val Trp Arg Gly Ser Trp Ser Cys
1               5                   10

```
<210> SEQ ID NO 72
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 72

Ala Pro Leu Cys Val Trp Arg Gly Ser Trp Ser Cys
1               5                   10

<210> SEQ ID NO 73
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 73

Ala Pro Leu Cys Val Tyr Arg Gly Ser Trp Ser Cys
1               5                   10

<210> SEQ ID NO 74
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 74

Ala Pro Ile Cys Val Tyr Arg Gly Ser Trp Ser Cys
1               5                   10

<210> SEQ ID NO 75
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 75

Ala Pro Trp Cys Val Phe Arg Gly Ser Trp Ser Cys
1               5                   10

<210> SEQ ID NO 76
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 76

Ala Pro His Cys Val Phe Arg Gly Ser Trp Ser Cys
1               5                   10

<210> SEQ ID NO 77
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 77

Ala Pro Tyr Cys Ser Tyr Tyr Gly Gln Trp Met Cys
1               5                   10

<210> SEQ ID NO 78
```

```
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 78

Ala Pro Phe Cys Leu Tyr Thr Gly Asp Trp Val Cys
1               5                   10

<210> SEQ ID NO 79
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 79

Ala Pro Phe Cys Ser Trp Ala Gly Trp Trp Thr Cys
1               5                   10

<210> SEQ ID NO 80
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 80

Ala Pro Tyr Cys Val Tyr Thr Gly Glu Trp Leu Cys
1               5                   10

<210> SEQ ID NO 81
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 81

Ala Pro Tyr Cys Val Tyr Asp Gly Thr Trp Ile Cys
1               5                   10

<210> SEQ ID NO 82
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 82

Ala Pro Tyr Cys Val Tyr Gly Gly Thr Trp Arg Cys
1               5                   10

<210> SEQ ID NO 83
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 83

Ala Pro Tyr Cys Val Tyr Ser Gly Thr Trp His Cys
1               5                   10

<210> SEQ ID NO 84
<211> LENGTH: 12
```

```
<212> TYPE: PRT
<213> ORGANISM: Artificial Sequence
<220> FEATURE:
<223> OTHER INFORMATION: EphA4 receptor cyclic peptide antagonist

<400> SEQUENCE: 84

Ala Pro Tyr Cys Val Tyr Asn Gly Thr Trp Asn Cys
1               5                   10

<210> SEQ ID NO 85
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 85

Ala Pro Tyr Cys Val Tyr Asp Gly Ser Trp Asn Cys
1               5                   10

<210> SEQ ID NO 86
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 86

Ala Pro Tyr Cys Val Tyr Lys Gly Ser Trp Asn Cys
1               5                   10

<210> SEQ ID NO 87
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 87

Ala Pro Tyr Cys Val Tyr Glu Gly Leu Trp Asn Cys
1               5                   10

<210> SEQ ID NO 88
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 88

Ala Pro Tyr Cys Val Tyr Ser Gly Val Trp Asn Cys
1               5                   10

<210> SEQ ID NO 89
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 89

Ala Pro Tyr Cys Val Tyr Ser Gly Trp Trp Lys Cys
1               5                   10

<210> SEQ ID NO 90
<211> LENGTH: 12
<212> TYPE: PRT
```

-continued

```
<213> ORGANISM: Artificial Sequence
<220> FEATURE:
<223> OTHER INFORMATION: EphA4 receptor cyclic peptide antagonist

<400> SEQUENCE: 90

Ala Pro Tyr Cys Val Tyr Ser Gly Arg Trp Glu Cys
1               5                   10

<210> SEQ ID NO 91
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 91

Ala Pro Tyr Cys Val Tyr Arg Gly Val Trp Glu Cys
1               5                   10

<210> SEQ ID NO 92
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 92

Ala Pro Tyr Cys Val Tyr Gln Gly Leu Trp Glu Cys
1               5                   10

<210> SEQ ID NO 93
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 93

Ala Pro Tyr Cys Val Tyr Gly Gly Leu Trp Thr Cys
1               5                   10

<210> SEQ ID NO 94
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 94

Ala Pro Tyr Cys Val Tyr Ala Gly Lys Trp Ser Cys
1               5                   10

<210> SEQ ID NO 95
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 95

Ala Pro Tyr Cys Val Tyr Gln Gly Tyr Trp Lys Cys
1               5                   10

<210> SEQ ID NO 96
<211> LENGTH: 12
<212> TYPE: PRT
<213> ORGANISM: Artificial Sequence
```

```
<220> FEATURE:
<223> OTHER INFORMATION: EphA4 receptor cyclic peptide antagonist

<400> SEQUENCE: 96

Ala Pro Tyr Cys Val Tyr Asn Gly Arg Trp Asp Cys
1               5                   10

<210> SEQ ID NO 97
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 97

Ala Pro Tyr Cys Val Tyr Arg Gly His Trp Gly Cys
1               5                   10

<210> SEQ ID NO 98
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 98

Gly Pro Tyr Cys Val Tyr Lys Gly Asn Trp Trp Cys
1               5                   10

<210> SEQ ID NO 99
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 99

Ala Pro Tyr Cys Val Tyr Arg Gly Ser Trp Ser Cys
1               5                   10

<210> SEQ ID NO 100
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 100

Glu Pro Tyr Cys Val Tyr Arg Gly Ser Trp Ser Cys
1               5                   10

<210> SEQ ID NO 101
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 101

Asp Ala Tyr Cys Val Tyr Arg Gly Ser Trp Ser Cys
1               5                   10

<210> SEQ ID NO 102
<211> LENGTH: 12
<212> TYPE: PRT
<213> ORGANISM: Artificial Sequence
<220> FEATURE:
```

```
<223> OTHER INFORMATION: EphA4 receptor cyclic peptide antagonist

<400> SEQUENCE: 102

Ala Ala Phe Cys Val Tyr Arg Gly Ser Trp Ser Cys
1               5                   10

<210> SEQ ID NO 103
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 103

Ala Pro Leu Cys Val Tyr Arg Gly Ser Trp Ser Cys
1               5                   10

<210> SEQ ID NO 104
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 104

Leu Pro Leu Cys Val Tyr Arg Gly Ser Trp Ser Cys
1               5                   10

<210> SEQ ID NO 105
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 105

Gly Pro Leu Cys Val Tyr Arg Gly Ser Trp Ser Cys
1               5                   10

<210> SEQ ID NO 106
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 106

Ser Ala Leu Cys Val Tyr Arg Gly Ser Trp Ser Cys
1               5                   10

<210> SEQ ID NO 107
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 107

Gln Ala Leu Cys Val Tyr Arg Gly Ser Trp Ser Cys
1               5                   10

<210> SEQ ID NO 108
<211> LENGTH: 12
<212> TYPE: PRT
<213> ORGANISM: Artificial Sequence
<220> FEATURE:
<223> OTHER INFORMATION: EphA4 receptor cyclic peptide antagonist
```

<400> SEQUENCE: 108

Phe Pro Val Cys Val Tyr Arg Gly Ser Trp Ser Cys
1               5                   10

<210> SEQ ID NO 109
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 109

Leu Pro Val Cys Val Tyr Arg Gly Ser Trp Ser Cys
1               5                   10

<210> SEQ ID NO 110
<211> LENGTH: 12
<212> TYPE: PRT
<213> ORGANISM: Artificial Sequence
<220> FEATURE:
<223> OTHER INFORMATION: EphA4 receptor cyclic peptide antagonist

<400> SEQUENCE: 110

Tyr Pro Met Cys Val Tyr Arg Gly Ser Trp Ser Cys
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Library 1 amino acid sequence for phage display
      screen
<220> FEATURE:
<221> NAME/KEY: VARIANT
<222> LOCATION: (3)..(3)
<223> OTHER INFORMATION: X is any amino acid
<220> FEATURE:
<221> NAME/KEY: VARIANT
<222> LOCATION: (6)..(6)
<223> OTHER INFORMATION: X is any amino acid

<400> SEQUENCE: 111

Ala Pro Xaa Cys Val Xaa Arg Gly Ser Trp Ser Cys
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Library 2 amino acid sequence for phage display
      screen
<220> FEATURE:
<221> NAME/KEY: VARIANT
<222> LOCATION: (3)..(3)
<223> OTHER INFORMATION: X is Tyr ot Phe
<220> FEATURE:
<221> NAME/KEY: VARIANT
<222> LOCATION: (5)..(5)
<223> OTHER INFORMATION: X is any amino acid
<220> FEATURE:
<221> NAME/KEY: VARIANT
<222> LOCATION: (6)..(6)
<223> OTHER INFORMATION: X is Tyr, Phe, Trp, Leu or Cys
<220> FEATURE:
<221> NAME/KEY: VARIANT
<222> LOCATION: (7)..(7)
<223> OTHER INFORMATION: X is any amino acid
<220> FEATURE:

-continued

```
<221> NAME/KEY: VARIANT
<222> LOCATION: (9)..(9)
<223> OTHER INFORMATION: X is any amino acid
<220> FEATURE:
<221> NAME/KEY: VARIANT
<222> LOCATION: (10)..(10)
<223> OTHER INFORMATION: X is any amino acid
<220> FEATURE:
<221> NAME/KEY: VARIANT
<222> LOCATION: (11)..(11)
<223> OTHER INFORMATION: X is any amino acid

<400> SEQUENCE: 112

Ala Pro Xaa Cys Xaa Xaa Xaa Gly Xaa Xaa Xaa Cys
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Library 3 amino acid sequence for phage display
      screen
<220> FEATURE:
<221> NAME/KEY: VARIANT
<222> LOCATION: (7)..(7)
<223> OTHER INFORMATION: X is any amino acid
<220> FEATURE:
<221> NAME/KEY: VARIANT
<222> LOCATION: (9)..(9)
<223> OTHER INFORMATION: X is any amino acid
<220> FEATURE:
<221> NAME/KEY: VARIANT
<222> LOCATION: (11)..(11)
<223> OTHER INFORMATION: X is any amino acid

<400> SEQUENCE: 113

Ala Pro Tyr Cys Val Tyr Xaa Gly Xaa Trp Xaa Cys
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Library 4 amino acid sequence for phage display
      screen
<220> FEATURE:
<221> NAME/KEY: VARIANT
<222> LOCATION: (1)..(1)
<223> OTHER INFORMATION: X is any amino acid
<220> FEATURE:
<221> NAME/KEY: VARIANT
<222> LOCATION: (2)..(2)
<223> OTHER INFORMATION: X is any amino acid
<220> FEATURE:
<221> NAME/KEY: VARIANT
<222> LOCATION: (3)..(3)
<223> OTHER INFORMATION: X is any amino acid

<400> SEQUENCE: 114

Xaa Xaa Xaa Cys Val Tyr Arg Gly Ser Trp Ser Cys
1               5                   10

<210> SEQ ID NO 115
<211> LENGTH: 85
<212> TYPE: DNA
<213> ORGANISM: Artificial Sequence
<220> FEATURE:
<223> OTHER INFORMATION: Library 1 oligonucliotide primer sequence for
      phage display screen
<220> FEATURE:
<221> NAME/KEY: misc_feature
```

<222> LOCATION: (43)..(44)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 115
catgtttcgg ccgatcctcc tccacacgac caagaacccc tmnncacaca mnncggagca      60
gagtgagaat agaaaggtac ccggg      85

<210> SEQ ID NO 116
<211> LENGTH: 85
<212> TYPE: DNA
<213> ORGANISM: Artificial Sequence
<220> FEATURE:
<223> OTHER INFORMATION: Library 2 oligonucliotide primer sequence for
      phage display screen
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 116
catgtttcgg ccgatcctcc tccacamnnm nnmnnaccmn nmhamnnaca awacggagca      60
gagtgagaat agaaaggtac ccggg      85

<210> SEQ ID NO 117
<211> LENGTH: 85
<212> TYPE: DNA
<213> ORGANISM: Artificial Sequence
<220> FEATURE:
<223> OTHER INFORMATION: Library 3 oligonucliotide primer sequence for
      phage display screen
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 117
catgtttcgg ccgatcctcc tccacamnnc camnnaccmn natacacaca atacggagca      60
gagtgagaat agaaaggtac ccggg      85

<210> SEQ ID NO 118
<211> LENGTH: 85
<212> TYPE: DNA

```
<213> ORGANISM: Artificial Sequence
<220> FEATURE:
<223> OTHER INFORMATION: Library 4 oligonucliotide primer sequence for
      phage display screen
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 118
catgtttcgg ccgatcctcc tccacacgac caagaacccc tatacacaca mnnmnnmnna     60
gagtgagaat agaaaggtac ccggg                                           85

<210> SEQ ID NO 119
<211> LENGTH: 11
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: X is Ahx
<220> FEATURE:
<221> NAME/KEY: MOD_RES
<222> LOCATION: (7)..(7)
<223> OTHER INFORMATION: X is bAla
<220> FEATURE:
<221> NAME/KEY: MOD_RES
<222> LOCATION: (11)..(11)
<223> OTHER INFORMATION: AMIDATION

<400> SEQUENCE: 119

Xaa Tyr Cys Val Tyr Arg Xaa Ser Trp Ser Cys
1               5                   10

<210> SEQ ID NO 120
<211> LENGTH: 11
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: X is Ava
<220> FEATURE:
<221> NAME/KEY: MOD_RES
<222> LOCATION: (7)..(7)
<223> OTHER INFORMATION: X is bAla
<220> FEATURE:
<221> NAME/KEY: MOD_RES
<222> LOCATION: (11)..(11)
<223> OTHER INFORMATION: AMIDATION

<400> SEQUENCE: 120

Xaa Tyr Cys Val Tyr Arg Xaa Ser Trp Ser Cys
1               5                   10

<210> SEQ ID NO 121
<211> LENGTH: 11
<212> TYPE: PRT
<213> ORGANISM: Artificial Sequence
<220> FEATURE:
```

```
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: X is gammaAbu
<220> FEATURE:
<221> NAME/KEY: MOD_RES
<222> LOCATION: (7)..(7)
<223> OTHER INFORMATION: X is bAla
<220> FEATURE:
<221> NAME/KEY: MOD_RES
<222> LOCATION: (11)..(11)
<223> OTHER INFORMATION: AMIDATION

<400> SEQUENCE: 121

Xaa Tyr Cys Val Tyr Arg Xaa Ser Trp Ser Cys
1               5                   10

<210> SEQ ID NO 122
<211> LENGTH: 11
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: X is bAla
<220> FEATURE:
<221> NAME/KEY: MOD_RES
<222> LOCATION: (7)..(7)
<223> OTHER INFORMATION: X is bAla
<220> FEATURE:
<221> NAME/KEY: MOD_RES
<222> LOCATION: (11)..(11)
<223> OTHER INFORMATION: AMIDATION

<400> SEQUENCE: 122

Xaa Tyr Cys Val Tyr Arg Xaa Ser Trp Ser Cys
1               5                   10

<210> SEQ ID NO 123
<211> LENGTH: 11
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (7)..(7)
<223> OTHER INFORMATION: X is bAla
<220> FEATURE:
<221> NAME/KEY: MOD_RES
<222> LOCATION: (11)..(11)
<223> OTHER INFORMATION: AMIDATION

<400> SEQUENCE: 123

Gly Tyr Cys Val Tyr Arg Xaa Ser Trp Ser Cys
1               5                   10

<210> SEQ ID NO 124
<211> LENGTH: 11
<212> TYPE: PRT
<213> ORGANISM: Artificial Sequence
<220> FEATURE:
<223> OTHER INFORMATION: EphA4 receptor cyclic peptide antagonist
<220> FEATURE:
<221> NAME/KEY: MOD_RES
<222> LOCATION: (1)..(1)
<223> OTHER INFORMATION: X is Sar
<220> FEATURE:
<221> NAME/KEY: MOD_RES
<222> LOCATION: (7)..(7)
```

```
<223> OTHER INFORMATION: X is bAla
<220> FEATURE:
<221> NAME/KEY: MOD_RES
<222> LOCATION: (11)..(11)
<223> OTHER INFORMATION: AMIDATION

<400> SEQUENCE: 124

Xaa Tyr Cys Val Tyr Arg Xaa Ser Trp Ser Cys
1               5                   10
```